(12) United States Patent
Asher et al.

(10) Patent No.: US 12,364,498 B2
(45) Date of Patent: Jul. 22, 2025

(54) SURGICAL INSTRUMENT WITH SELECTIVELY ACTUATED GAP-SETTING FEATURES FOR END EFFECTOR

(71) Applicant: Cilag GmbH International, Zug (CH)

(72) Inventors: Ryan M. Asher, Cincinnati, OH (US); Brian D. Black, Loveland, OH (US); John E. Brady, Liberty Township, OH (US); Joseph Dennis, Cincinnati, OH (US); Geni M. Giannotti, Allendale, NJ (US); Bryce L. Heitman, Newton, IA (US); Timothy S. Holland, Madison, WI (US); Joseph E. Hollo, Liberty Township, OH (US); Andrew Kolpitcke, Centerville, OH (US); Amy M. Krumm, Cincinnati, OH (US); Jason R. Lesko, Cincinnati, OH (US); Matthew C. Miller, Cincinnati, OH (US); David A. Monroe, Milford, OH (US); Ion V. Nicolaescu, Carpentersville, IL (US); Rafael J. Ruiz Ortiz, Mason, OH (US); Matthew S. Schneider, Blue Ash, OH (US); Richard C. Smith, Milford, OH (US); Shawn C. Snyder, Greendale, IN (US); Sarah A. Worthington, Cincinnati, OH (US); Monica L. Rivard, Cincinnati, OH (US); Fajian Zhang, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/612,507

(22) Filed: Mar. 21, 2024

(65) Prior Publication Data
US 2024/0341792 A1    Oct. 17, 2024

Related U.S. Application Data

(63) Continuation of application No. 17/128,534, filed on Dec. 21, 2020, now Pat. No. 11,963,691, which is a
(Continued)

(51) Int. Cl.
*A61B 17/28* (2006.01)
*A61B 17/00* (2006.01)
(Continued)

(52) U.S. Cl.
CPC ...... *A61B 17/2804* (2013.01); *A61B 18/1442* (2013.01); *A61B 2017/00106* (2013.01);
(Continued)

(58) Field of Classification Search
CPC .... A61B 17/320068; A61B 17/320092; A61B 2017/230072; A61B 2017/320074;
(Continued)

(56) References Cited

U.S. PATENT DOCUMENTS 5,322,055 A  6/1994  Davison et al.
5,766,167 A  6/1998  Eggers et al.
(Continued)

FOREIGN PATENT DOCUMENTS

CN  1325333 A  12/2001
CN  1714762 A   1/2006
(Continued)

OTHER PUBLICATIONS

U.S. Appl. No. 17/128,534 published as: U.S. Pat. No. 11,963,691 Aug. 23, 2024 Asher et al.
(Continued)

*Primary Examiner* — Todd J Scherbel
(74) *Attorney, Agent, or Firm* — Frost Brown Todd LLP

(57) ABSTRACT

A surgical instrument, has an end effector that includes an ultrasonic blade, and a clamp arm that moves relative to the
(Continued)

ultrasonic blade from an opened position toward an intermediate position and a closed position. The clamp arm is offset from the ultrasonic blade to define a predetermined gap in the intermediate position between the opened position and the closed position. A clamp arm actuator connects to the clamp arm and moves from an opened configuration to a closed configuration to direct the clamp arm from the opened position toward the intermediate position and the closed position. A spacer connects with the clamp arm to inhibit movement of the clamp arm from the intermediate position toward the closed position for maintaining the predetermined gap between the clamp arm and the ultrasonic blade.

18 Claims, 68 Drawing Sheets

Related U.S. Application Data continuation of application No. 15/798,720, filed on Oct. 31, 2017, now Pat. No. 11,116,532.

(60) Provisional application No. 62/519,482, filed on Jun. 14, 2017, provisional application No. 62/508,720, filed on May 19, 2017, provisional application No. 62/422,698, filed on Nov. 16, 2016.

(51) Int. Cl.
| | |
|---|---|
| *A61B 18/14* | (2006.01) |
| *A61B 17/32* | (2006.01) |
| *A61B 18/00* | (2006.01) |
| *A61B 18/12* | (2006.01) |
| *A61B 90/00* | (2016.01) |

(52) U.S. Cl.
CPC ............... *A61B 2017/00367* (2013.01); *A61B 2017/00424* (2013.01); *A61B 2017/0046* (2013.01); *A61B 2017/00477* (2013.01); *A61B 2017/00876* (2013.01); *A61B 2017/2825* (2013.01); *A61B 2017/2845* (2013.01); *A61B 2017/320074* (2017.08); *A61B 2017/320082* (2017.08); *A61B 2017/320084* (2013.01); *A61B 2017/320088* (2013.01); *A61B 2017/320093* (2017.08); *A61B 2017/320094* (2017.08); *A61B 2017/320095* (2017.08); *A61B 2018/0063* (2013.01); *A61B 2018/00642* (2013.01); *A61B 2018/00666* (2013.01); *A61B 2018/00672* (2013.01); *A61B 2018/00755* (2013.01); *A61B 2018/00875* (2013.01); *A61B 2018/00916* (2013.01); *A61B 2018/0094* (2013.01); *A61B 2018/00958* (2013.01); *A61B 2018/00994* (2013.01); *A61B 18/1206* (2013.01); *A61B 2090/034* (2016.02); *A61B 2090/065* (2016.02); *A61B 2090/0811* (2016.02); *A61B 2090/0813* (2016.02)

(58) Field of Classification Search
CPC ........ A61B 2017/320094; A61B 17/28; A61B 17/2804; A61B 17/2812; A61B 17/2816; A61B 17/2833; A61B 17/2841; A61B 17/2845; A61B 17/285; A61B 2017/2901; A61B 2017/2909; A61B 18/1442; A61B 18/1445; A61B 18/1447; A61B 18/1452
See application file for complete search history.

(56) References Cited

U.S. PATENT DOCUMENTS

| | | | |
|---|---|---|---|
| 5,873,873 | A | 2/1999 | Smith et al. |
| 5,935,144 | A | 8/1999 | Estabrook |
| 5,980,510 | A | 11/1999 | Tsonton et al. |
| 6,129,735 | A | 10/2000 | Okada et al. |
| 6,139,561 | A | 10/2000 | Shibata et al. |
| 6,325,811 | B1 | 12/2001 | Messerly |
| 6,773,444 | B2 | 8/2004 | Messerly |
| 6,783,524 | B2 | 8/2004 | Anderson et al. |
| 7,563,269 | B2 | 7/2009 | Hashiguchi |
| 8,048,074 | B2 | 11/2011 | Masuda |
| 8,461,744 | B2 | 6/2013 | Wiener et al. |
| 8,591,536 | B2 | 11/2013 | Robertson |
| 8,623,027 | B2 | 1/2014 | Price et al. |
| 8,768,435 | B2 | 7/2014 | Andrus et al. |
| 8,905,935 | B2 | 12/2014 | Akagane |
| 8,926,610 | B2 | 1/2015 | Hafner et al. |
| 8,986,302 | B2 | 3/2015 | Aldridge et al. |
| 9,023,071 | B2 | 5/2015 | Miller et al. |
| 9,050,120 | B2 | 6/2015 | Swarup et al. |
| 9,072,523 | B2 | 7/2015 | Houser et al. |
| 9,084,878 | B2 | 7/2015 | Kawaguchi et al. |
| 9,095,367 | B2 | 8/2015 | Olsen et al. |
| 9,326,787 | B2 | 5/2016 | Sanai et al. |
| 9,351,753 | B2 | 5/2016 | Balanev et al. |
| 9,381,058 | B2 | 7/2016 | Houser et al. |
| 9,393,037 | B2 | 7/2016 | Olson et al. |
| 9,510,891 | B2 | 12/2016 | Allen, IV et al. |
| 9,566,084 | B2 | 2/2017 | Katsumata |
| 9,572,622 | B2 | 2/2017 | Shelton, IV et al. |
| 9,901,360 | B2 | 2/2018 | Neurohr et al. |
| 9,949,785 | B2 | 4/2018 | Price et al. |
| 10,543,383 | B2 | 1/2020 | Kase |
| 10,568,682 | B2 | 2/2020 | Dycus et al. |
| 10,736,648 | B2 | 8/2020 | Denzinger et al. |
| 11,039,848 | B2 | 6/2021 | Asher et al. |
| 11,116,531 | B2 | 9/2021 | Asher et al. |
| 11,116,532 | B2 | 9/2021 | Asher et al. |
| 11,602,364 | B2 | 3/2023 | Asher et al. |
| 11,666,353 | B2 | 6/2023 | Denzinger et al. |
| 2001/0029390 | A1 | 10/2001 | Fogarty et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2010/0331873 | A1 | 12/2010 | Dannaher et al. |
| 2012/0116265 | A1 | 5/2012 | Houser et al. |
| 2012/0203143 | A1 | 8/2012 | Sanai et al. |
| 2013/0103065 | A1 | 4/2013 | Timm et al. |
| 2013/0303949 | A1 | 11/2013 | Kawaguchi et al. |
| 2014/0135804 | A1 | 5/2014 | Weisenburgh, II et al. |
| 2014/0221994 | A1 | 8/2014 | Reschke |
| 2015/0080924 | A1 | 3/2015 | Stulen et al. |
| 2015/0080925 | A1 | 3/2015 | Schulte et al. |
| 2015/0088126 | A1 | 3/2015 | Duffin et al. |
| 2015/0142031 | A1 | 5/2015 | Faller et al. |
| 2015/0148835 | A1 | 5/2015 | Faller et al. |
| 2015/0250531 | A1 | 9/2015 | Dycus et al. |
| 2015/0265305 | A1 | 9/2015 | Stulen et al. |
| 2016/0030076 | A1 | 2/2016 | Faller et al. |
| 2016/0058492 | A1 | 3/2016 | Yates et al. |
| 2016/0175001 | A1 | 6/2016 | Hibner et al. |
| 2017/0105754 | A1 | 4/2017 | Boudreaux et al. |
| 2017/0105755 | A1 | 4/2017 | Boudreaux et al. |
| 2017/0105788 | A1 | 4/2017 | Boudreaux |
| 2018/0256245 | A1 | 9/2018 | Price et al. |
| 2020/0375619 | A1 | 12/2020 | Denzinger et al. |

FOREIGN PATENT DOCUMENTS

| | | |
|---|---|---|
| CN | 102665575 A | 9/2012 |
| CN | 103027719 A | 4/2013 |
| CN | 103379871 A | 10/2013 |
| CN | 203988246 U | 12/2014 |
| CN | 104540461 A | 4/2015 |
| CN | 105142550 A | 12/2015 |

(56) References Cited

FOREIGN PATENT DOCUMENTS

| | | |
|---|---|---|
| CN | 105792763 A | 7/2016 |
| CN | 105939679 A | 9/2016 |
| EP | 0316816 A1 | 5/1989 |
| JP | 2000-197640 A | 7/2000 |
| JP | 2004-033565 A | 2/2004 |
| JP | 2004-313542 A | 11/2004 |
| JP | 2005-176905 A | 7/2005 |
| JP | 2005-253674 A | 9/2005 |
| JP | 2006-288431 A | 10/2006 |
| JP | 2013-545536 A | 12/2013 |
| JP | 2016-504153 A | 2/2016 |
| WO | WO 2011/008672 A2 | 1/2011 |
| WO | WO 2013/062103 A1 | 4/2015 |
| WO | WO 2016/015233 A1 | 2/2016 |

OTHER PUBLICATIONS

Brazilian Examination Report dated Jan. 24, 2022 for Application No. BR 112019009930-1, 4 pgs.
Chinese Search Report dated Apr. 22, 2022 for Application No. CN 201780082585.8, 2 pgs.
Chinese Search Report dated Apr. 22, 2022 for Application No. CN 201780083110.0, 1 pg.
Chinese Search Report dated Apr. 25, 2022 for Application No. CN 201780083479.1, 1 pg.
Chinese Search Report dated Apr. 22, 2022 for Application No. CN 201780083505.0, 2 pgs.
Chinese Search Report dated Apr. 22, 2022 for Application No. CN 201780083514.X, 1 pg.
European Examination Report dated Jun. 5, 2020 for Application No. 17812121.6, 4 pages.
European Communication dated Jan. 20, 2021 for Application No. 17812121.6, 3 pages.
European Examination Report dated Jun. 5, 2020 for Application No. 17851837.9, 3 pages.
European Examination Report dated Jun. 5, 2020 for Application No. 17811769.3, 3 pages.
European Search Report, Extended, and Written Opinion dated Aug. 7, 2020 for Application No. 20163273.4, 7 pages.
European Search Report, Extended, and Written Opinion dated Jan. 20, 2022 for Application No. 21189412.6, 8 pgs.
Indian Office Action dated Jun. 30, 2021, for Application No. 201917019250, 5 pages.
Indian Office Action dated Jun. 30, 2021, for Application No. 201917019251, 6 pages.
Indian Office Action dated Jun. 25, 2021, for Application No. 201917019429, 5 pages.
Indian Office Action dated Jul. 23, 2021, for Application No. 201917019428, 6 pages.
Indian Office Action dated Jul. 12, 2021, for Application No. 201917019253, 6 pgs.
International Search Report and Written Opinion dated Jan. 30, 2018 for International Application No. PCT/US2017/061995, 11 pages.
International Search Report and Written Opinion dated Jun. 20, 2018 for International Application No. PCT/US2017/062010, 16 pages.
International Search Report and Written Opinion dated Apr. 13, 2018 for International Application No. PCT/US2017/062016, 17 pages.
International Search Report and Written Opinion dated Feb. 1, 2018 for International Application No. PCT/US2017/062023, 13 pages.
International Search Report and Written Opinion dated Apr. 3, 2018 for International Application No. PCT/US2017/062025, 18 pages.
Japanese Office Action, Notification of Reasons for Refusal dated Sep. 27, 2021, for Application No. 2019-547241, 10 pages.
Japanese Office Action, Notification of Reasons for Refusal dated Oct. 5, 2021, for Application No. 2019-547242, 10 pages.
Japanese Office Action, Notification of Reasons for Refusal dated Oct. 5, 2021, for Application No. 2019-547243, 7 pages.
Japanese Office Action, Notification of Reasons for Refusal dated Oct. 5, 2021, for Application No. 2019-547244, 8 pages.
Japanese Office Action, Notification of Reasons for Refusal dated Oct. 5, 2021, for Application No. 2019-547245, 7 pages.
U.S. Appl. No. 61/410,603, filed Nov. 5, 2010.
U.S. Appl. No. 62/363,411, filed Jul. 18, 2016.
U.S. Appl. No. 62/422,698, filed Nov. 16, 2016.
U.S. Appl. No. 62/508,720, filed May 19, 2017.
U.S. Appl. No. 62/519,482, filed Jun. 14, 2017.

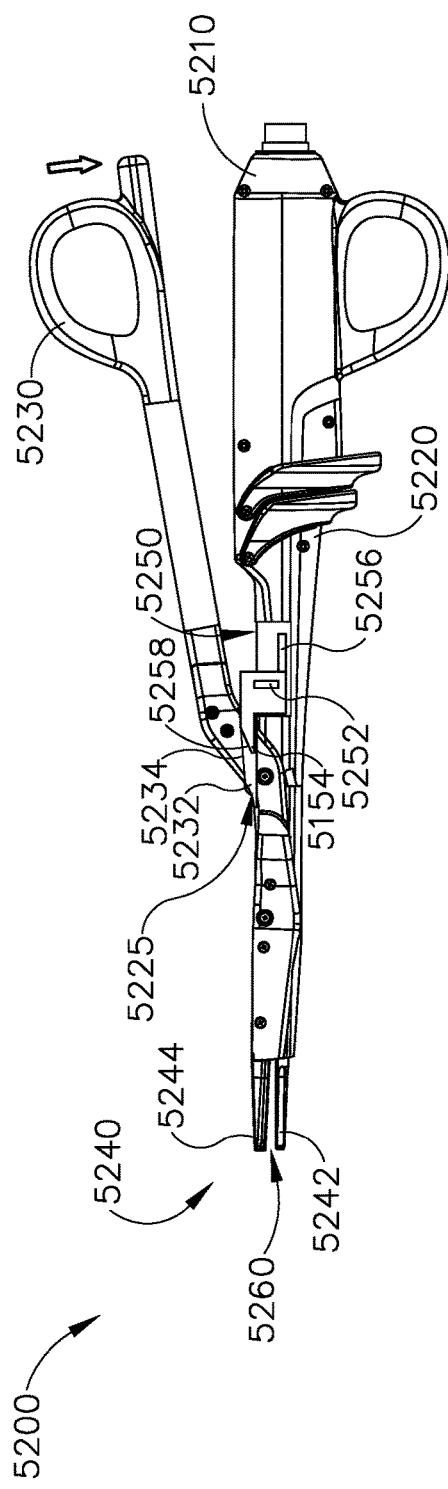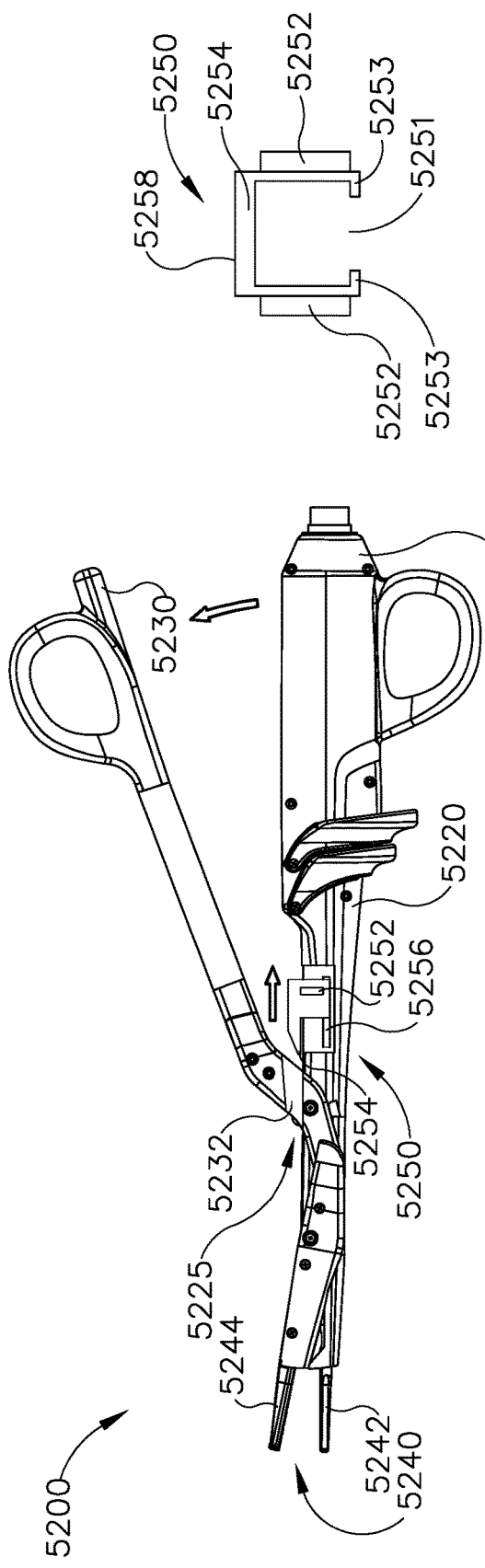

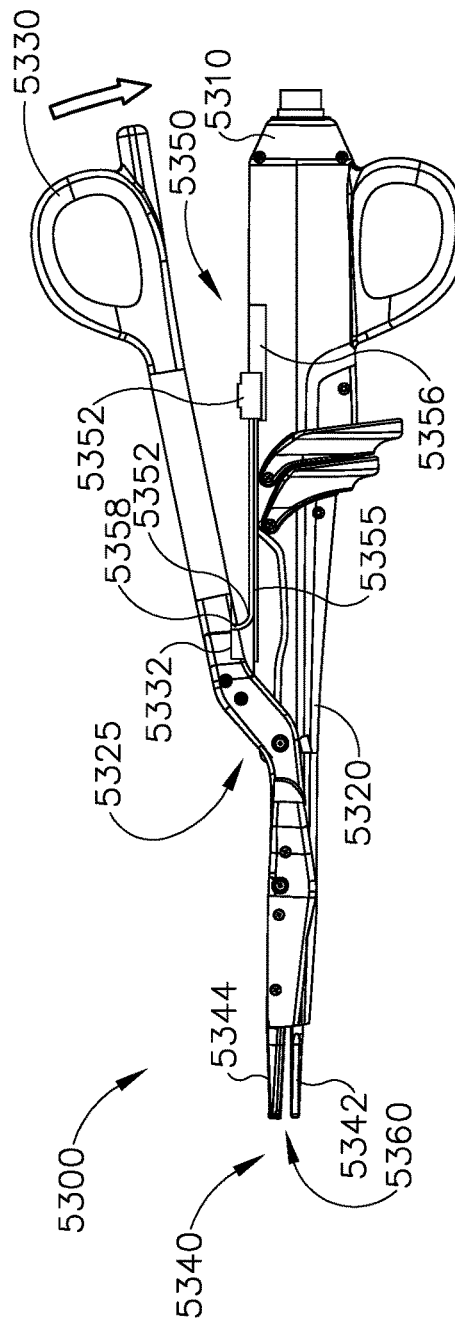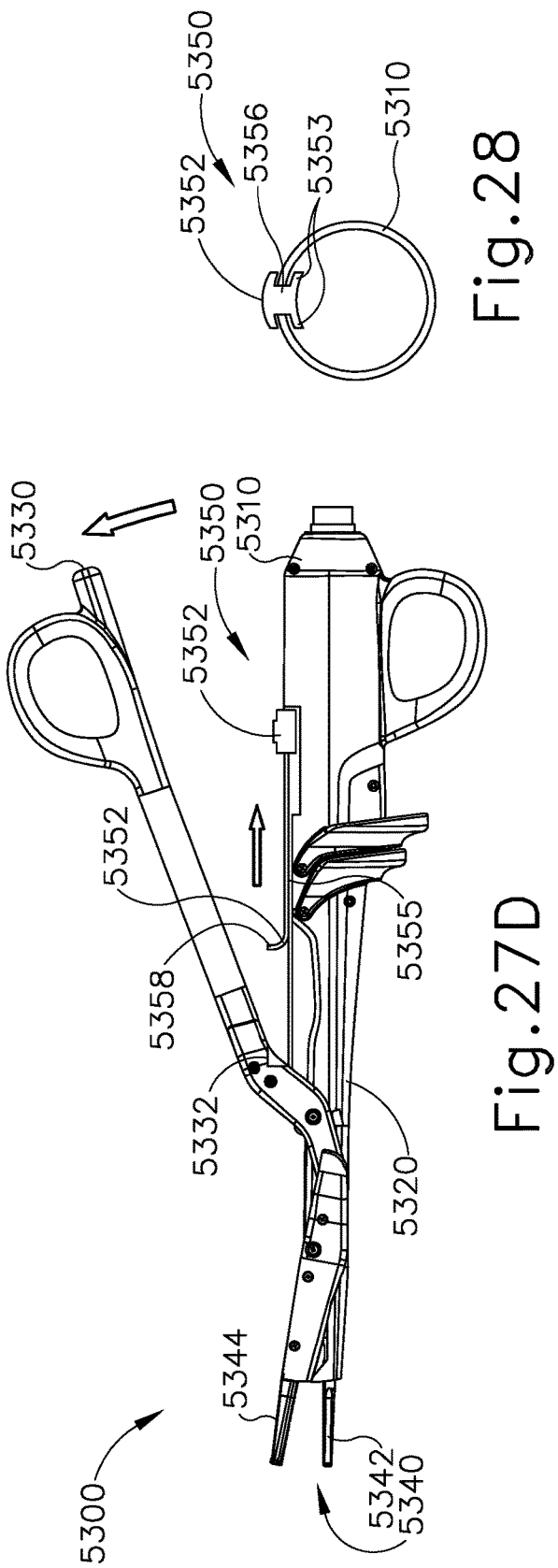

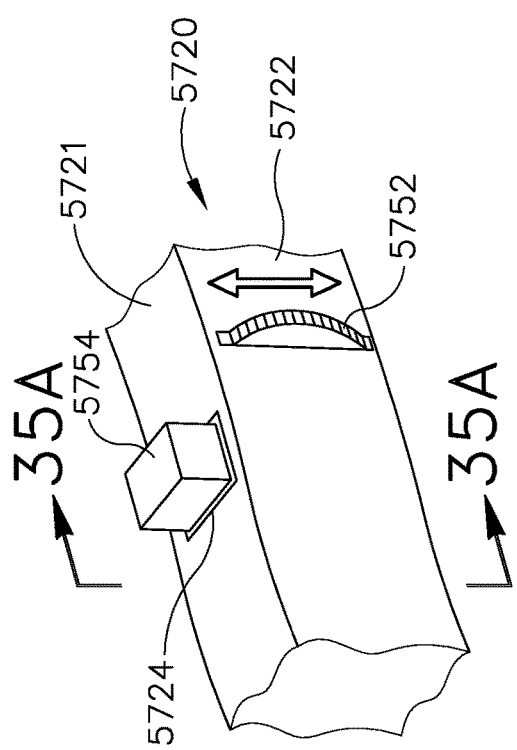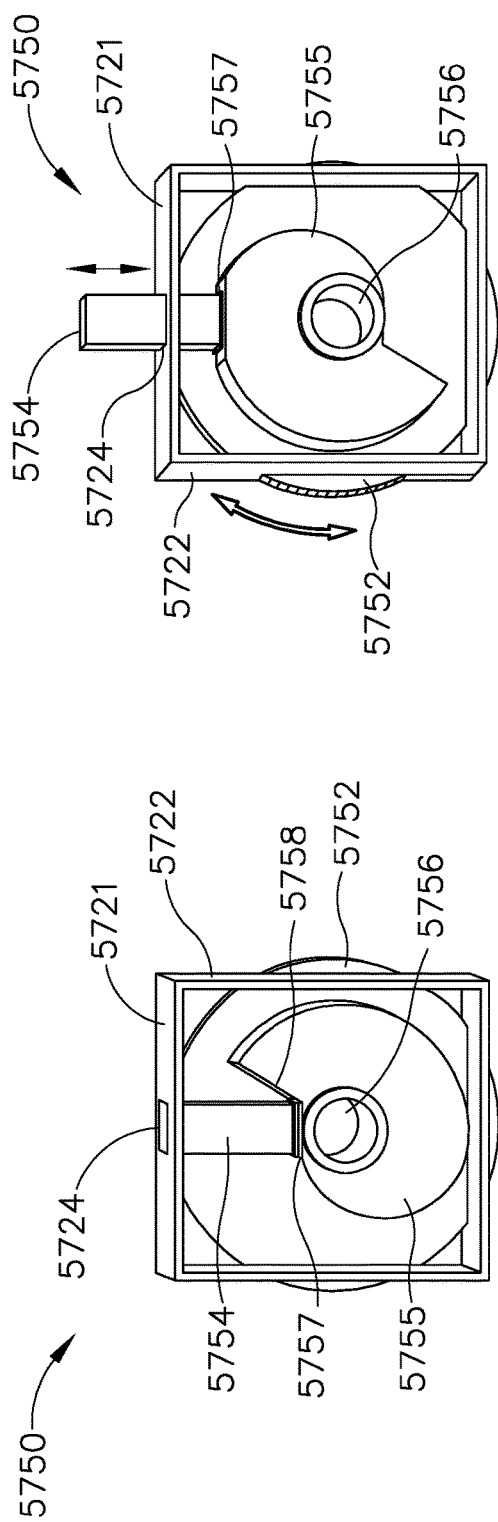

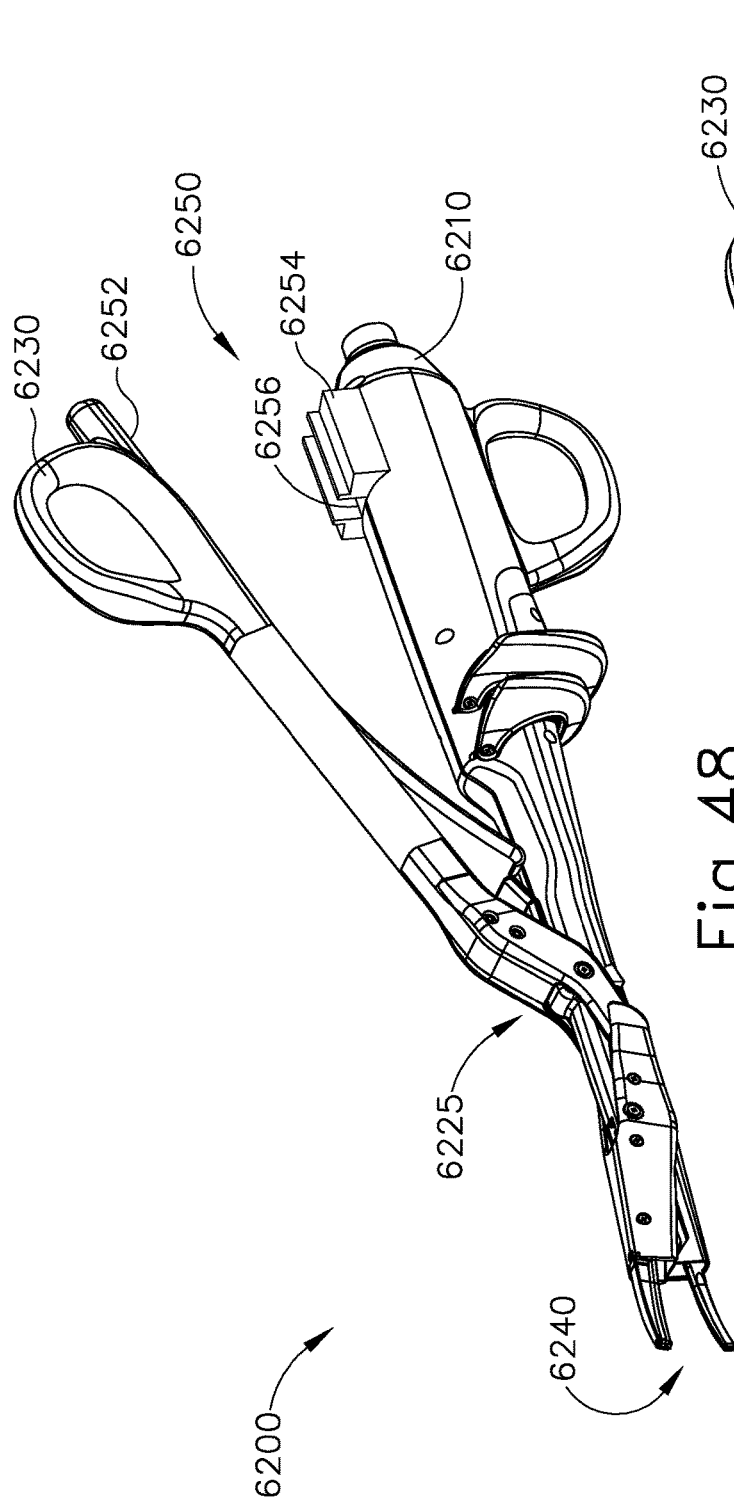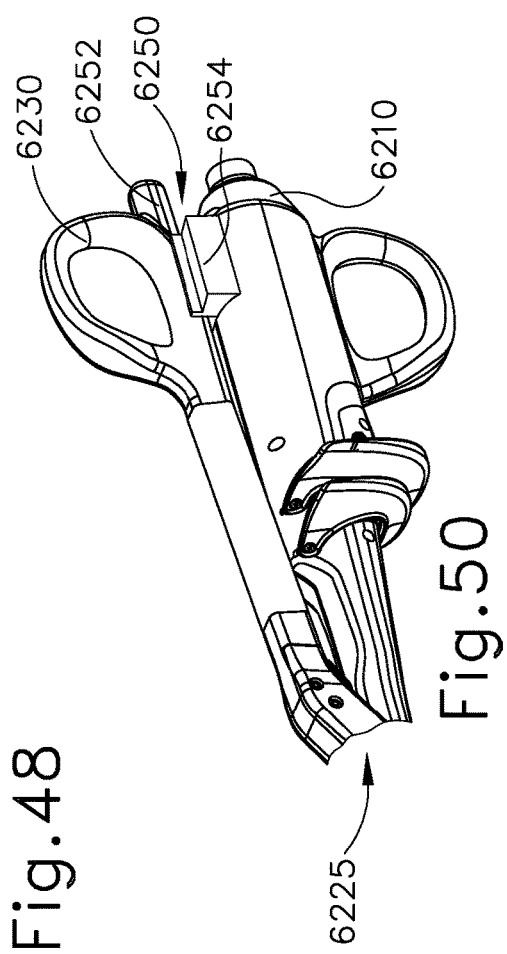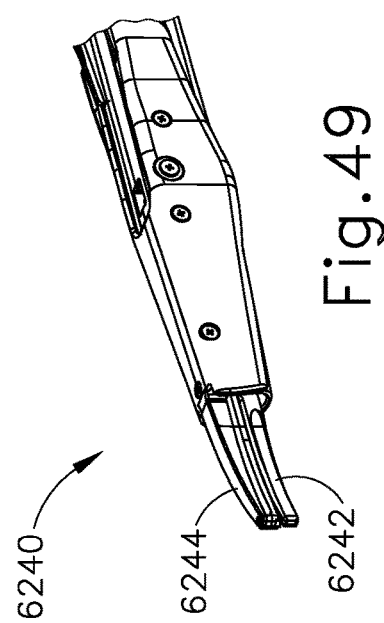
Fig.48
Fig.49
Fig.50

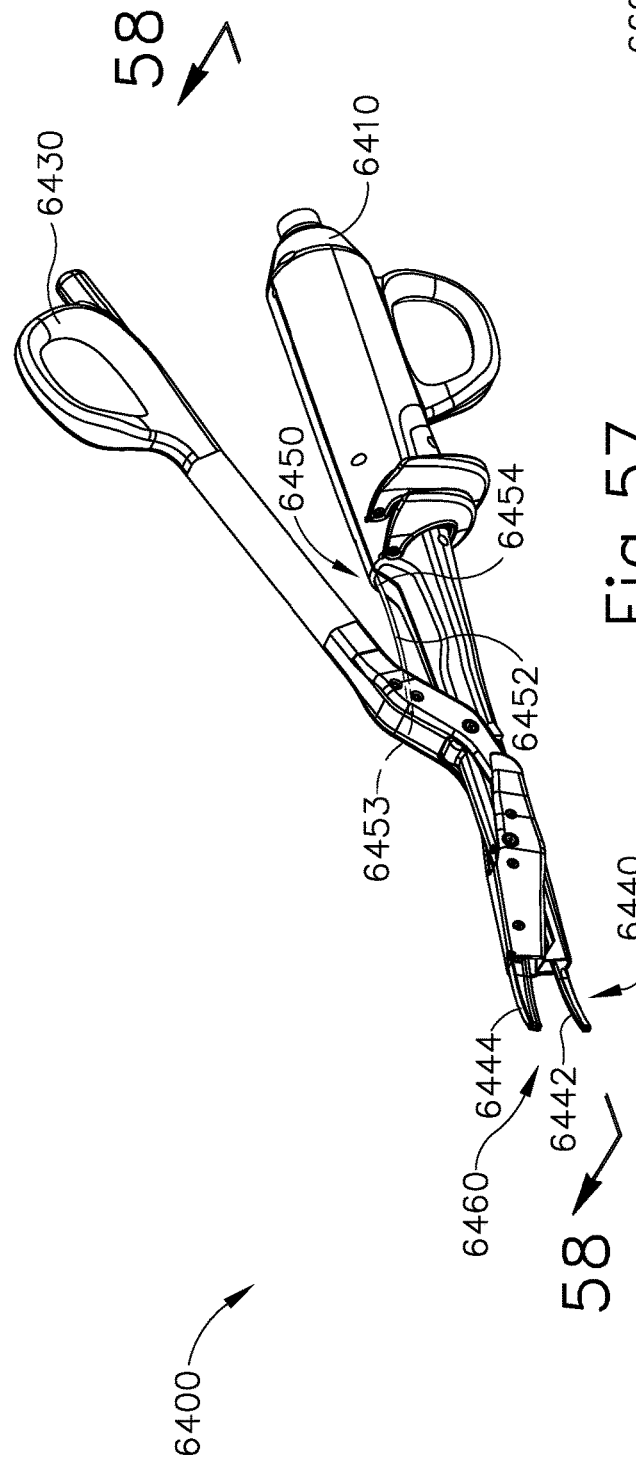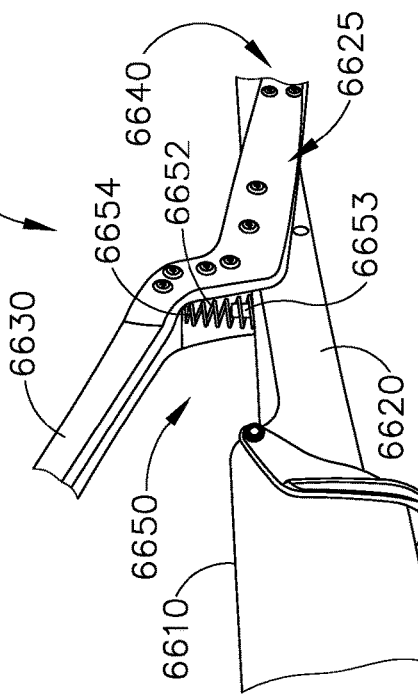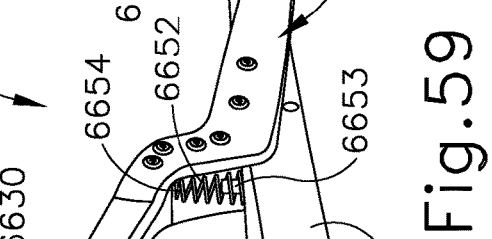

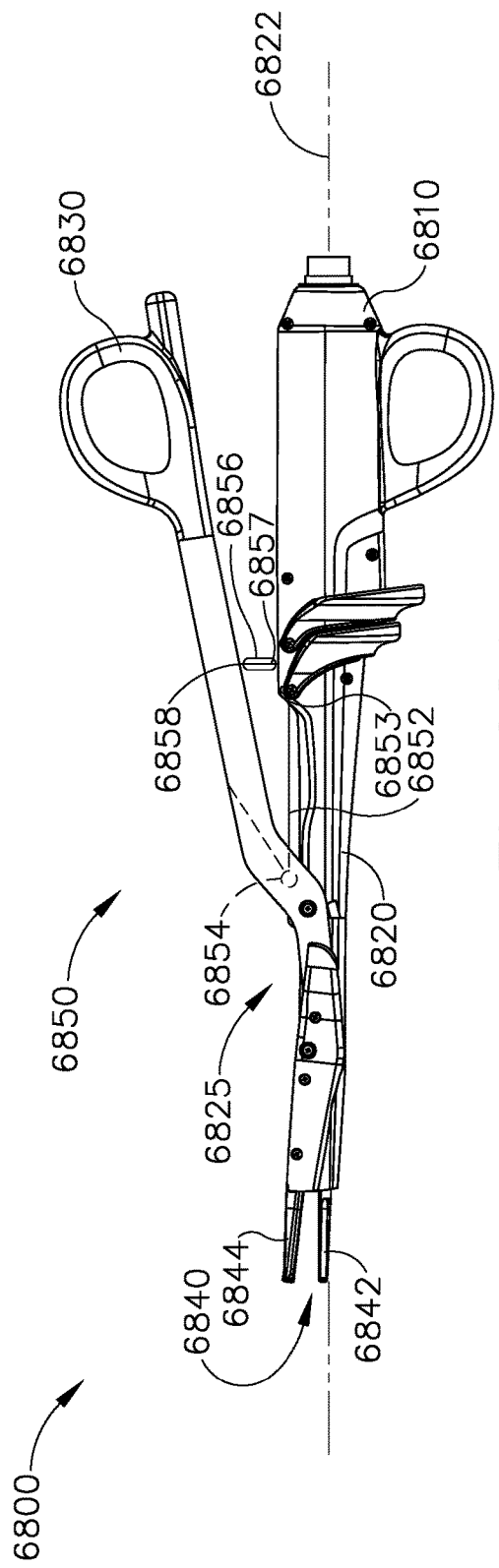
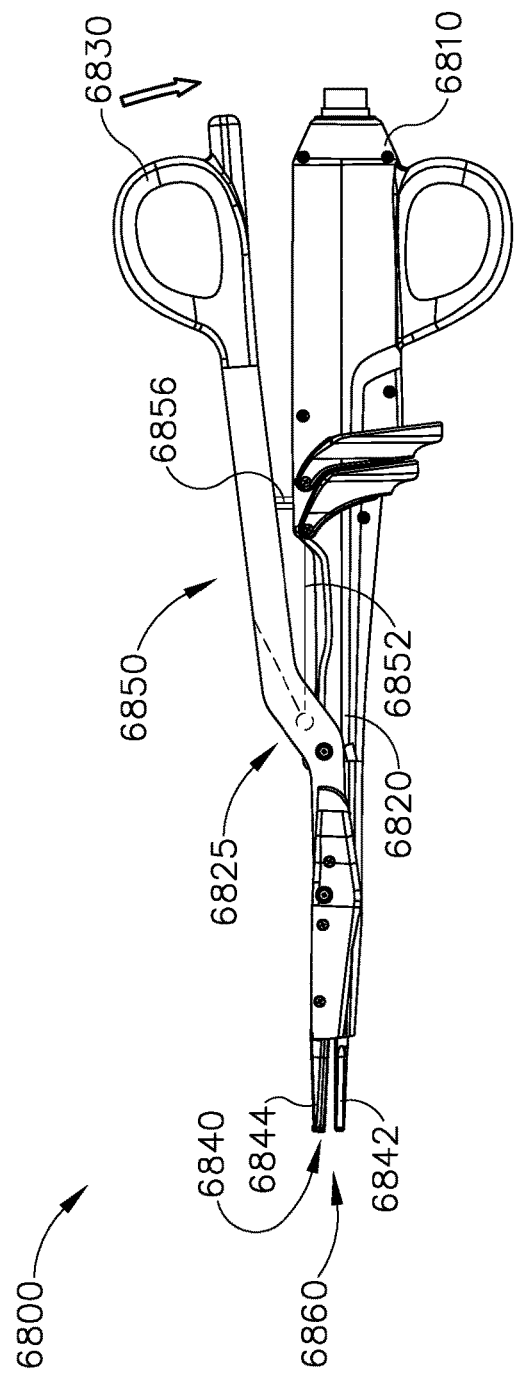

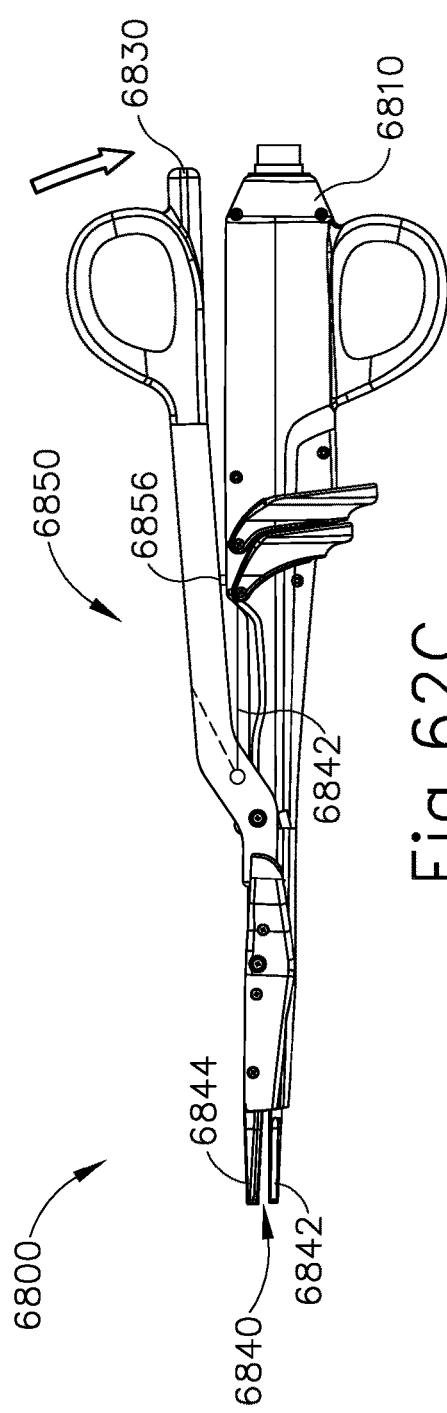
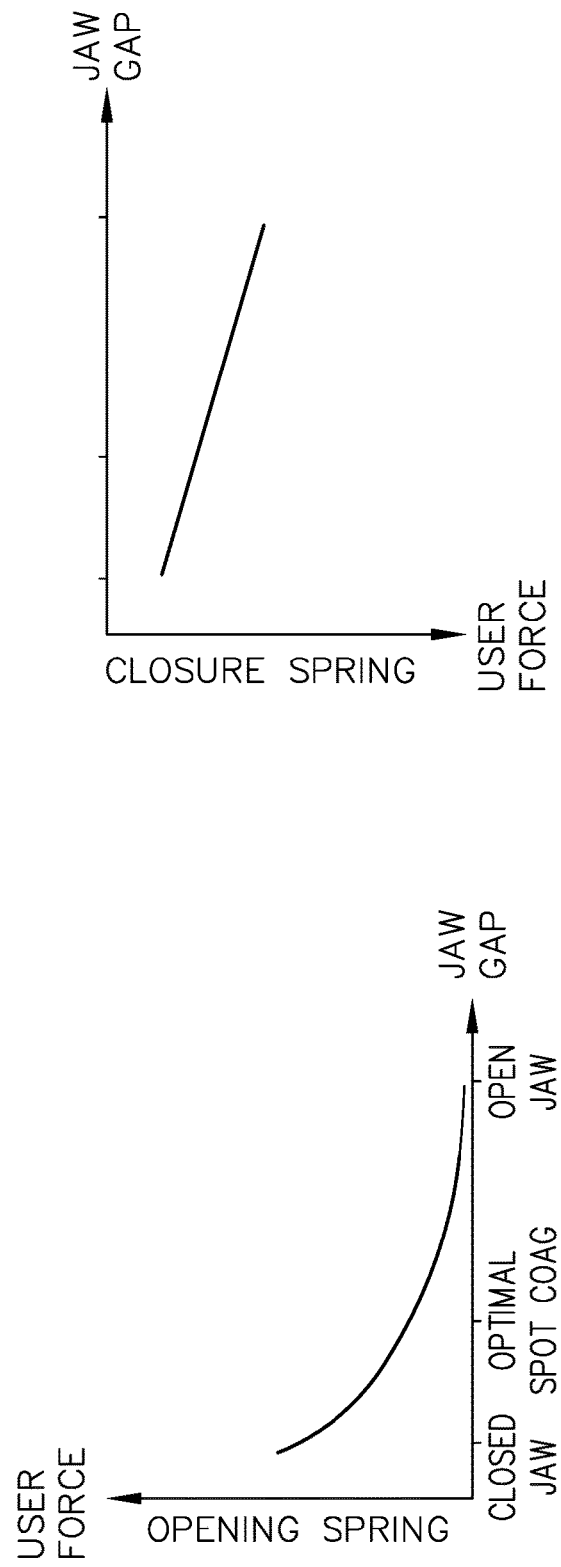
Fig.62C
Fig.63
Fig.64

SURGICAL INSTRUMENT WITH SELECTIVELY ACTUATED GAP-SETTING FEATURES FOR END EFFECTOR

PRIORITY

This application is a continuation of U.S. patent application Ser. No. 17/128,534, entitled "Surgical Instrument with Selectively Actuated Gap-Setting Features for End Effector," filed Dec. 21, 2020, published as U.S. Pub. No. 2021/0137544 on May 13, 2021, and issued as U.S. Pat. No. 11,963,691 on Apr. 23, 2024, which is a continuation of U.S. patent application Ser. No. 15/798,720, entitled "Surgical Instrument with Selectively Actuated Gap-Setting Features for End Effector," filed Oct. 31, 2017 and issued as U.S. Pat. No. 11,116,532 on Sep. 14, 2021, the disclosure of which is incorporated by reference herein, which claims priority to: (1) U.S. Provisional Patent Application Ser. No. 62/422,698, filed Nov. 16, 2016, entitled "Ultrasonic Surgical Shears with Contained Compound Lever Clamp Arm Actuator," the disclosure of which is incorporated by reference herein; (2) U.S. Provisional Patent Application Ser. No. 62/508,720, filed May 19, 2017, entitled "Ultrasonic and Electrosurgical Instrument with Replaceable End Effector Features," the disclosure of which is incorporated by reference herein; and (3) U.S. Provisional Patent Application Ser. No. 62/519,482, filed Jun. 14, 2017, entitled "Ultrasonic and Electrosurgical Instrument with Removable Features," the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVER Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,023,071, entitled "Ultrasonic Device for Fingertip Control," issued May 5, 2015, the disclosure of which is incorporated by reference herein; and U.S. Pat. No. 8,461,744, entitled "Rotating Transducer Mount for Ultrasonic Surgical Instruments," issued Jun. 11, 2013, the disclosure of which is incorporated by reference herein; and U.S. Pat. No. 8,591,536, entitled "Ultrasonic Surgical Instrument Blades," issued Nov. 26, 2013, the disclosure of which is incorporated by reference herein.

Some of ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, entitled "Surgical Instruments with Articulating Shafts," issued Jul. 19, 2016, the disclosure of which is incorporated by reference herein; and U.S. Pat. No. 9,095,367, entitled "Flexible Harmonic Waveguides/Blades for Surgical Instruments," issued Aug. 4, 2015 the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 25C depicts a side elevational view of the surgical instrument of FIG. 25A, with the slidable spacer in the actuated position and the end effector in an intermediate position;

FIG. 25D depicts a side elevational view of the surgical instrument of FIG. 25A, with the slidable spacer returned to the unactuated position and the blocker distal to the clamp arm actuator, with the end effector extended back to the open position;

FIG. 26 depicts a front elevational view of the slidable spacer of FIG. 25A;

FIG. 27C depicts a side elevational view of the surgical instrument of FIG. 27A, with the slidable spacer in the actuated position and the end effector in an intermediate position;

FIG. 27D depicts a side elevational view of the surgical instrument of FIG. 27A, with the slidable spacer returned to the unactuated position and the blocker extending proximally to a clamp arm actuator, with the end effector extended back to the open position;

FIG. 28 depicts a front elevational view of the slidable spacer of FIG. 27A;

FIG. 34 depicts a perspective view of the rotatable spacer of FIG. 33A, with the rotatable spacer in the actuated position;

FIG. 35A depicts a cross-sectional view taken along line 35A-35A of FIG. 34, with the rotatable spacer in the unactuated position;

FIG. 35B depicts a cross-sectional view taken along line 35A-35A of FIG. 34, with the rotatable spacer in the actuated position;

FIG. 48 depicts a perspective view of a fourteenth exemplary surgical instrument including an exemplary alternative static spacer and an end effector, with the static spacer in an unactuated position and the end effector in an open position;

FIG. 49 depicts a partial perspective view of the surgical instrument of FIG. 48, with the end effector in a closed position;

FIG. 50 depicts a partial perspective view of the surgical instrument of FIG. 48, with the static spacer in the unactuated position and a clamp arm actuator received within a blocker;

FIG. 57 depicts a perspective view of a sixteenth exemplary surgical instrument including an exemplary biasing urging mechanism and an end effector, with the biasing urging mechanism positioned between a clamp arm actuator and a handle body, with the end effector in an open position;

FIG. 58 depicts a cross-sectional view of the surgical instrument of FIG. 57 taken along section line 58-58 of FIG. 57 showing another exemplary biasing urging mechanism and an end effector, with the biasing urging mechanism positioned along the end effector and the end effector in an intermediate position;

FIG. 59 depicts an enlarged perspective view of a seventeenth exemplary surgical instrument with yet another exemplary biasing urging mechanism;

FIG. 62A depicts a side elevational view of a nineteenth exemplary surgical instrument including an exemplary dual urging mechanism and an end effector, with the dual urging mechanism in an unactuated position and including two springs, with the end effector in an open position;

FIG. 62B depicts a side elevational view of the surgical instrument of FIG. 62A, with the dual urging mechanism in an actuated position and the end effector in an intermediate position;

FIG. 62C depicts a side elevational view of the surgical instrument of FIG. 62A, with the dual urging mechanism in the unactuated position and the end effector in a closed position;

FIG. 63 is a diagrammatical view of the relationship between an opening spring of the dual urging mechanism of FIG. 62A and the end effector;

FIG. 64 is a diagrammatical view of the relationship between a closing spring of the dual urging mechanism of FIG. 62A and the end effector.

Figure 1A:
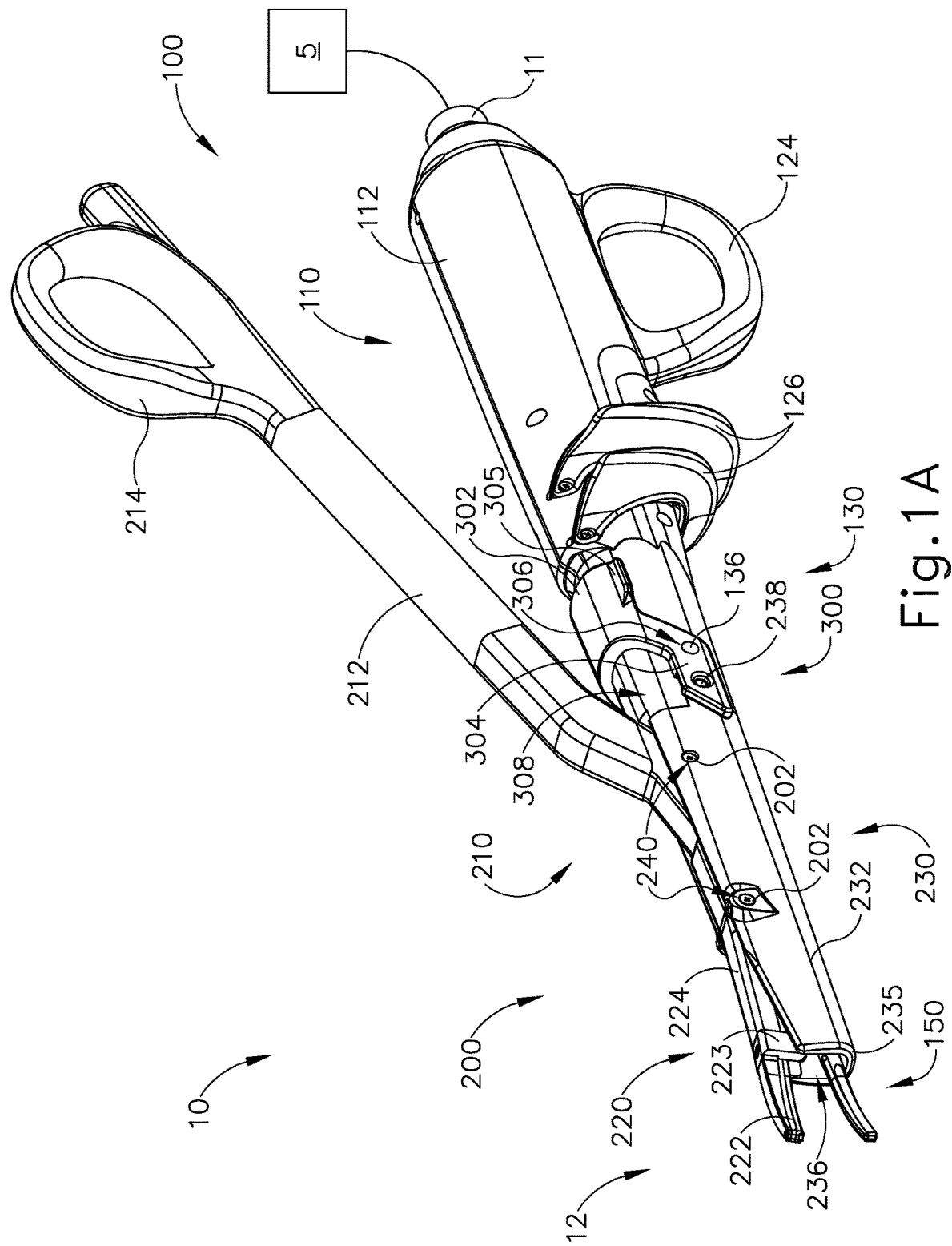
FIG. 1A depicts a perspective view of a first exemplary surgical instrument, with an end effector of the instrument in an open configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," and "top" are relative terms to provide additional clarity to the figure descriptions provided below. The terms "upper," "lower," "lateral," "transverse," "bottom," and "top" are thus not intended to unnecessarily limit the invention described herein.

I. First Exemplary Ultrasonic Surgical Instrument for Open Surgical Procedures

FIGS. 1A-2 and FIGS. 13A-13C illustrate a first exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. Nos. 8,623,027; 9,023,071; 8,461,744; 9,381,058; U.S. Pub. No. 2012/0116265, now abandoned; U.S. Pat. Nos. 9,393,037; 9,095,367; U.S. Pat. App. No. 61/410,603; and/or U.S. Pub. No. 2015/0080924, issued as U.S. Pat. No. 10,172,363 on Jan. 8, 2019. The disclosures of each of the foregoing patents, publications, and applications are incorporated by reference herein. In addition, or in the alternative, at least part of instrument (10) may be constructed and operable in accordance with at least some of the teachings of U.S. Pub. No. 2017/0105755, entitled "Surgical Instrument with Dual Mode End Effector and Compound Lever with Detents," published Apr. 20, 2017, issued as U.S. Pat. No. 11,020,200 the disclosure of which is incorporated by reference herein; and/or U.S. Pat. App. No. 62/363,411, entitled "Surgical Instrument with Dual Mode End Effector," filed Jul. 18, 2016, the disclosure of which is incorporated by reference herein.

As described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACER Ultrasonic Shears, the HARMONIC WAVER Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

Figure 1B:
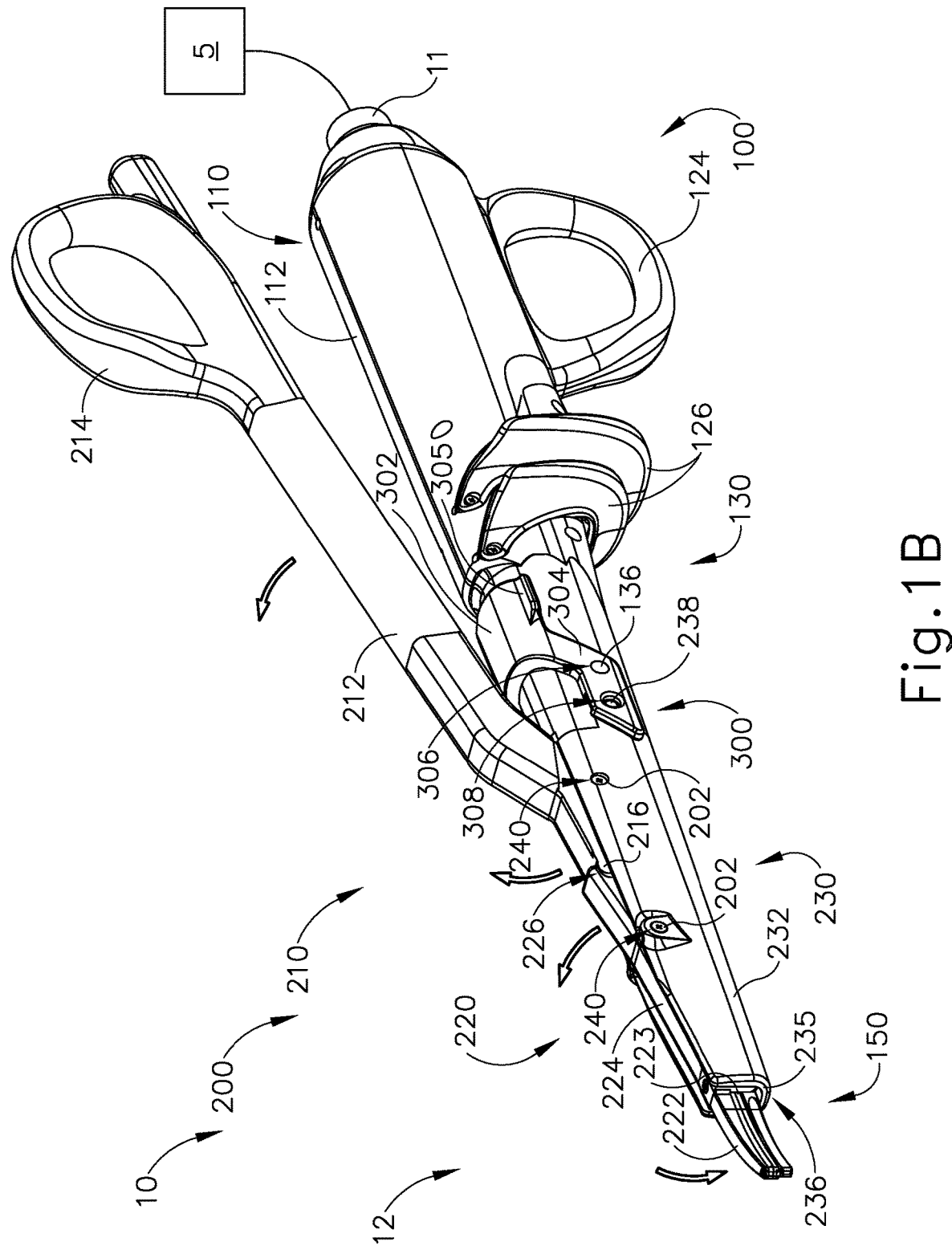
FIG. 1B depicts a perspective view of the instrument of FIG. 1A, with the end effector in a closed configuration.
Figure 2:
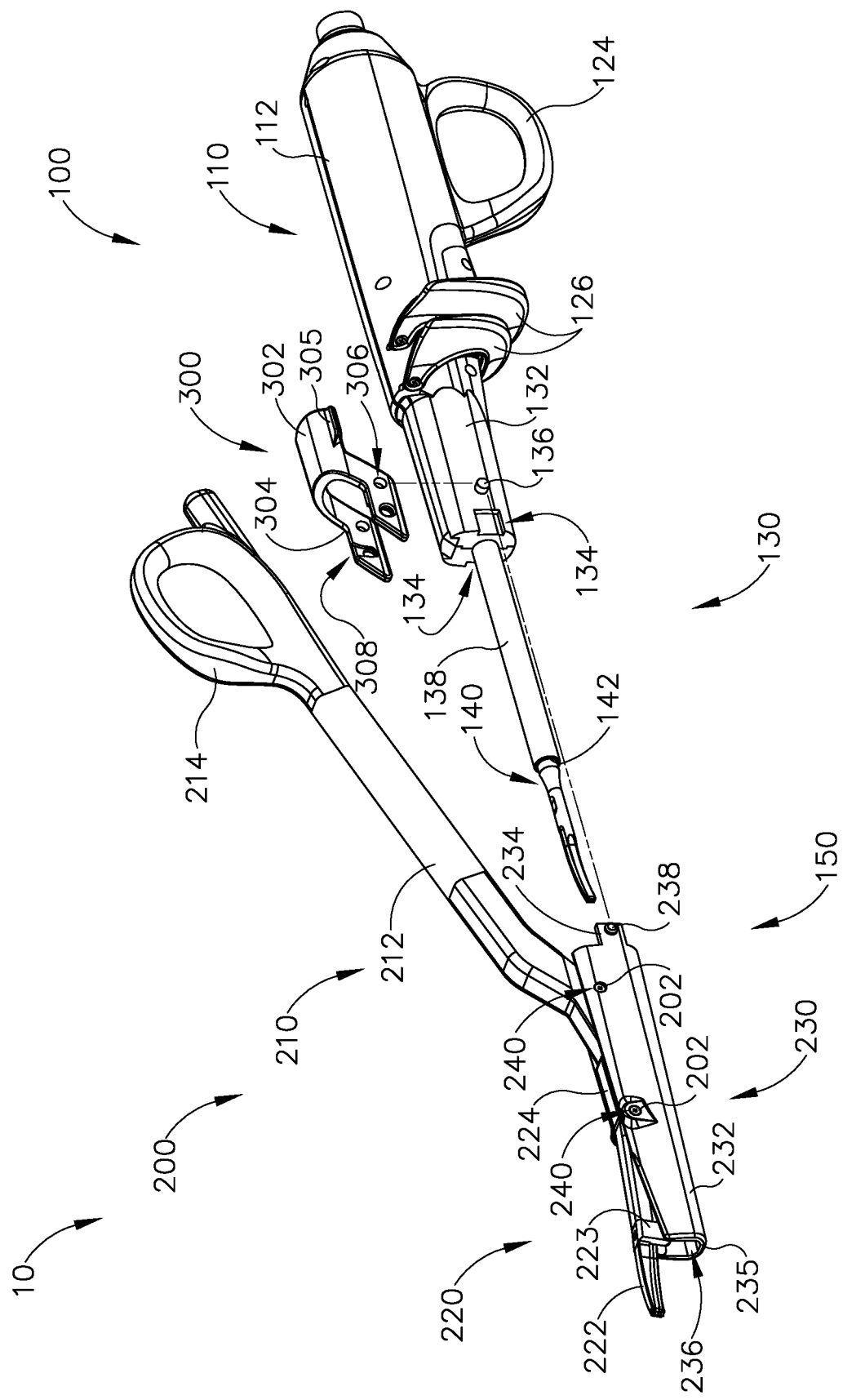
FIG. 2 depicts an exploded perspective view of the instrument of FIG. 1A.
Figure 3:
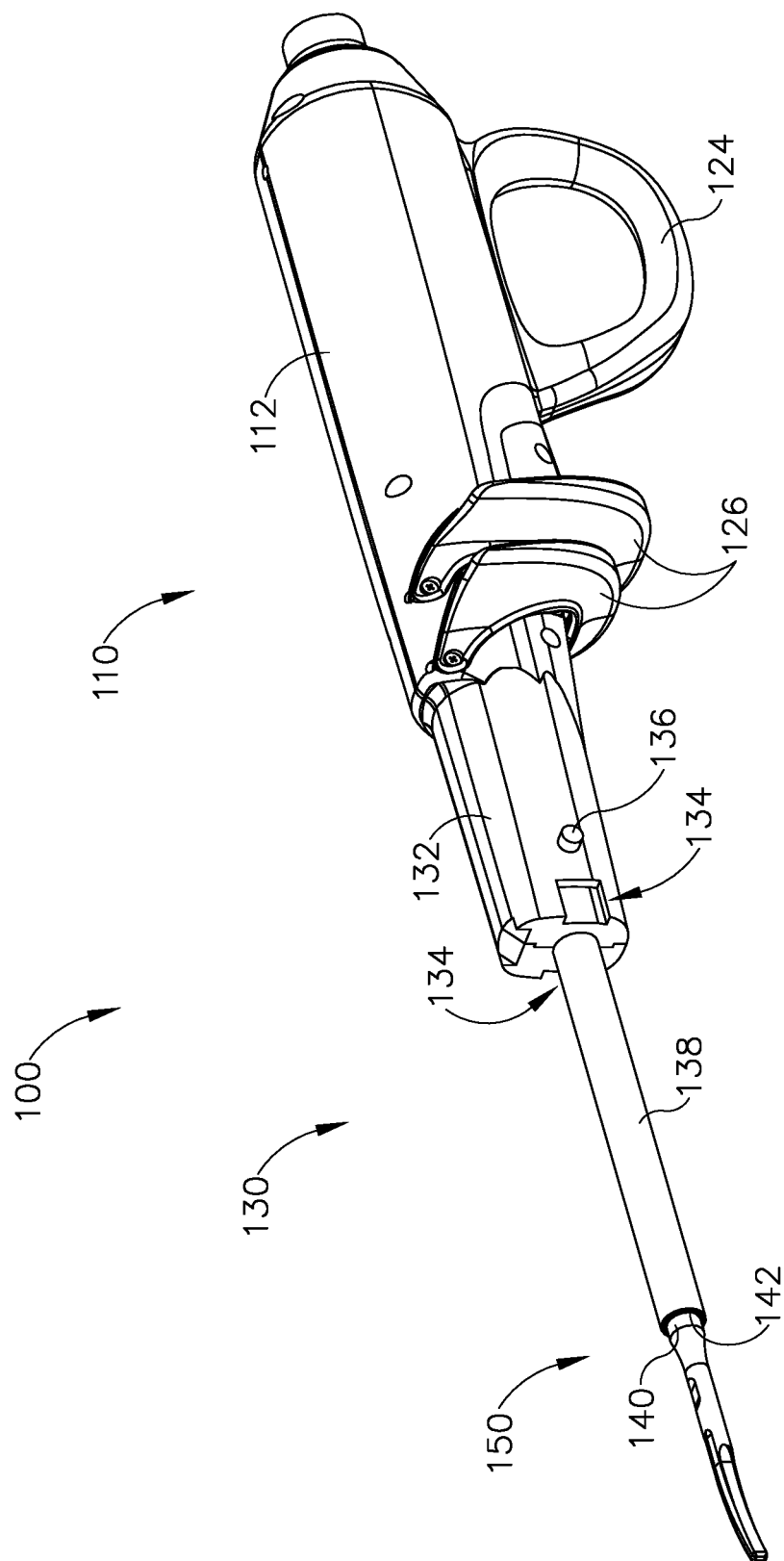
FIG. 3 depicts a perspective view of a first modular assembly of the instrument of FIG. 1A.

Instrument (10) in the present example includes a first modular assembly (100), a second modular assembly (200), and a coupling member (300). As will be described in greater detail below, coupling member (300) may selectively attach first modular assembly (100) with second modular assembly (200) in order to form instrument (10) with an end effector (12). As best seen in FIGS. 1A-1B, end effector (12) comprises an ultrasonic blade (150) and a clamp pad (222) of a clamp pad assembly (220).

Figure 16A:
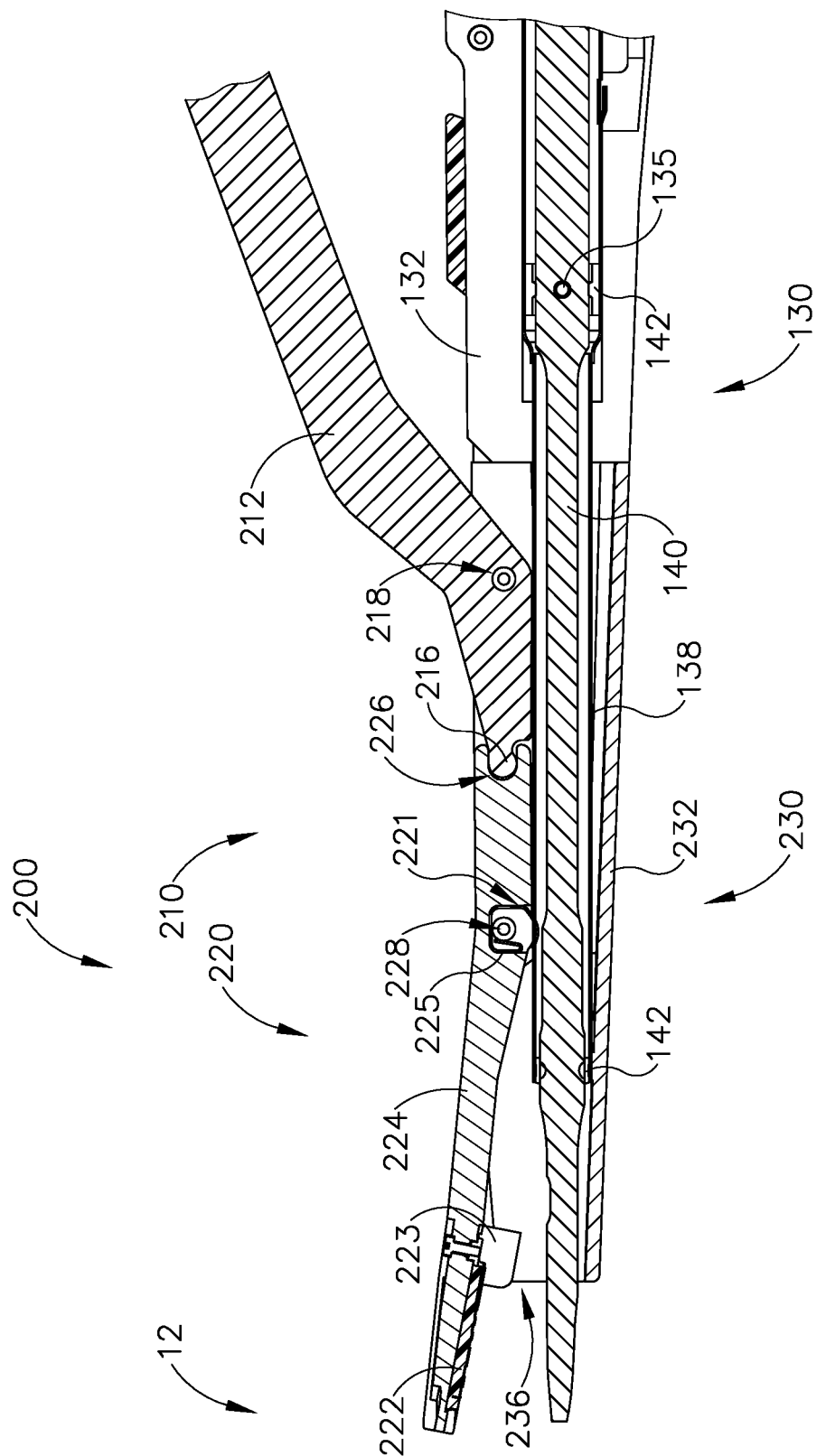
FIG. 16A depicts a cross-sectional side view of the second modular assembly of FIG. 8 coupled with the shaft assembly of FIG. 5, where the end effector is in an open configuration.
Figure 16B:
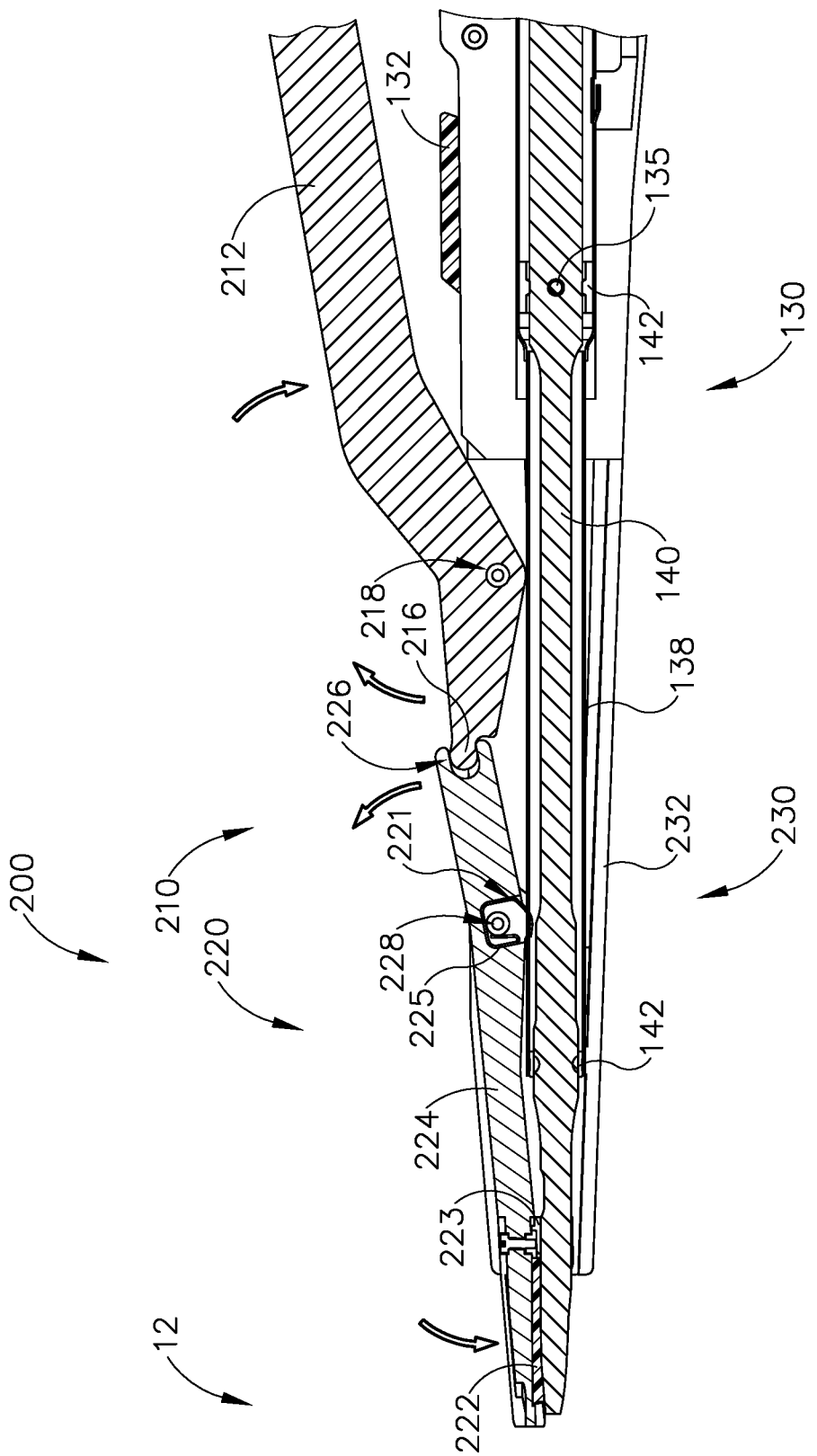
FIG. 16B depicts a cross-sectional side view of the second modular assembly of FIG. 8 coupled with the shaft assembly of FIG. 5, where the end effector is in a closed configuration.

Additionally, as will be described in greater detail below, selected portions of second modular assembly (200) may actuate relative to first modular assembly (100), when properly attached with each other, in order to actuate end effector (12) from an open configuration (FIGS. 1A and 16A), to a closed configuration (FIGS. 1B and 16B). The ability to selectively attach and detach second modular assembly (200) with first modular assembly (100) may provide additional benefits of reusability of either modular assembly (100, 200). For instance, different kinds of first modular assemblies (100) may be used with second modular assembly (200) to provide different kinds of surgical instruments. Similarly, different kinds of second modular assemblies (200) may be used with first modular assembly (100) to provide different kinds of surgical instruments. Additionally, moving components of second modular assembly (200) may be housed within static components of second modular assembly (200), which may provide additional advantages, some of which are described below while others will be apparent to one having ordinary skill in the art in view of the teachings herein.

First modular assembly (100) includes a handle assembly (110), a shaft assembly (130) extending distally from handle assembly (110), and an ultrasonic blade (150) extending distally from shaft assembly (130). Handle assembly (110) includes a body (112), a finger grip ring (124), a pair of buttons (126) distal to finger grip ring (124), and an ultrasonic transducer assembly (30) housed within body (112).

Shaft assembly (130) includes a proximal outer sheath (132) extending distally from body (112), a tube (138) extending distally from proximal outer sheath (132), and a waveguide (140) extending within and through both proximal outer sheath (132) and tube (138). Proximal outer sheath (132) includes a pair of protrusions (136). Additionally, proximal outer sheath (132) defines a pair of recesses (134). As will be described in greater detail below, recesses (134) are dimensioned to mate with a portion of distal outer sheath (230) while protrusions (136) are configured to pivotally couple proximal outer sheath (132) with coupling member (300). Both recesses (134) and protrusions (136) may help couple first modular assembly (100) with coupling member (300).

Proximal outer sheath (132) may be fixed relative to body (112), while tube (138) may be fixed relative to proximal outer sheath (132). As will be described in greater detail below, waveguide (140) may attach to transducer assembly (30) and be supported by portions proximal outer sheath (132) and tube (138). Ultrasonic blade (150) may be unitarily connected to waveguide (140), and also extend distally from waveguide (140). As will be described in greater detail below, waveguide (140) is operable to connect to ultrasonic transducer assembly (30) in order to provide acoustic communication between ultrasonic blade (150) and transducer assembly (30).

Figure 4:
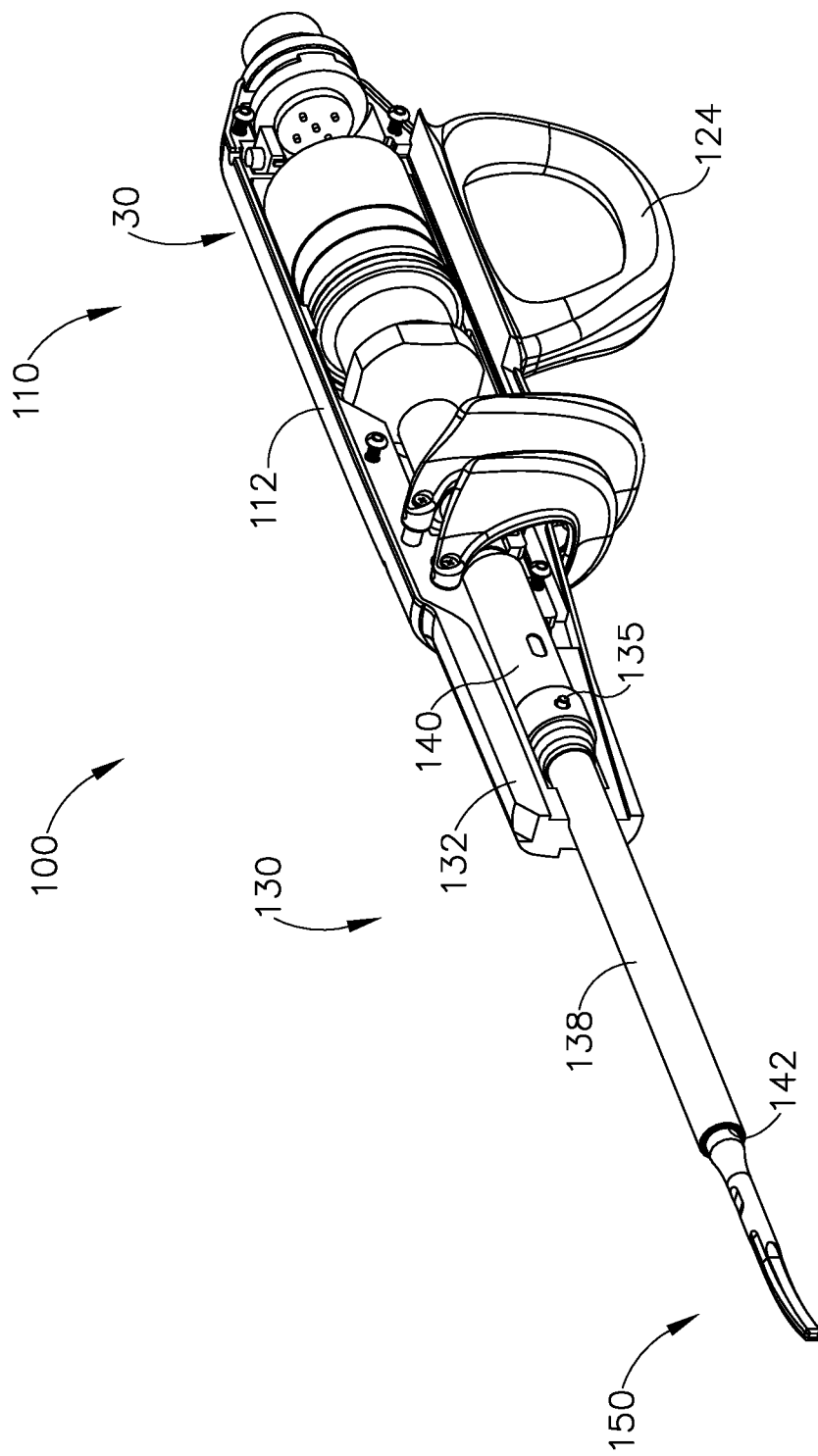
FIG. 4 depicts a perspective view of the first modular assembly of FIG. 3, with selected portions purposefully omitted for clarity.
Figure 5:
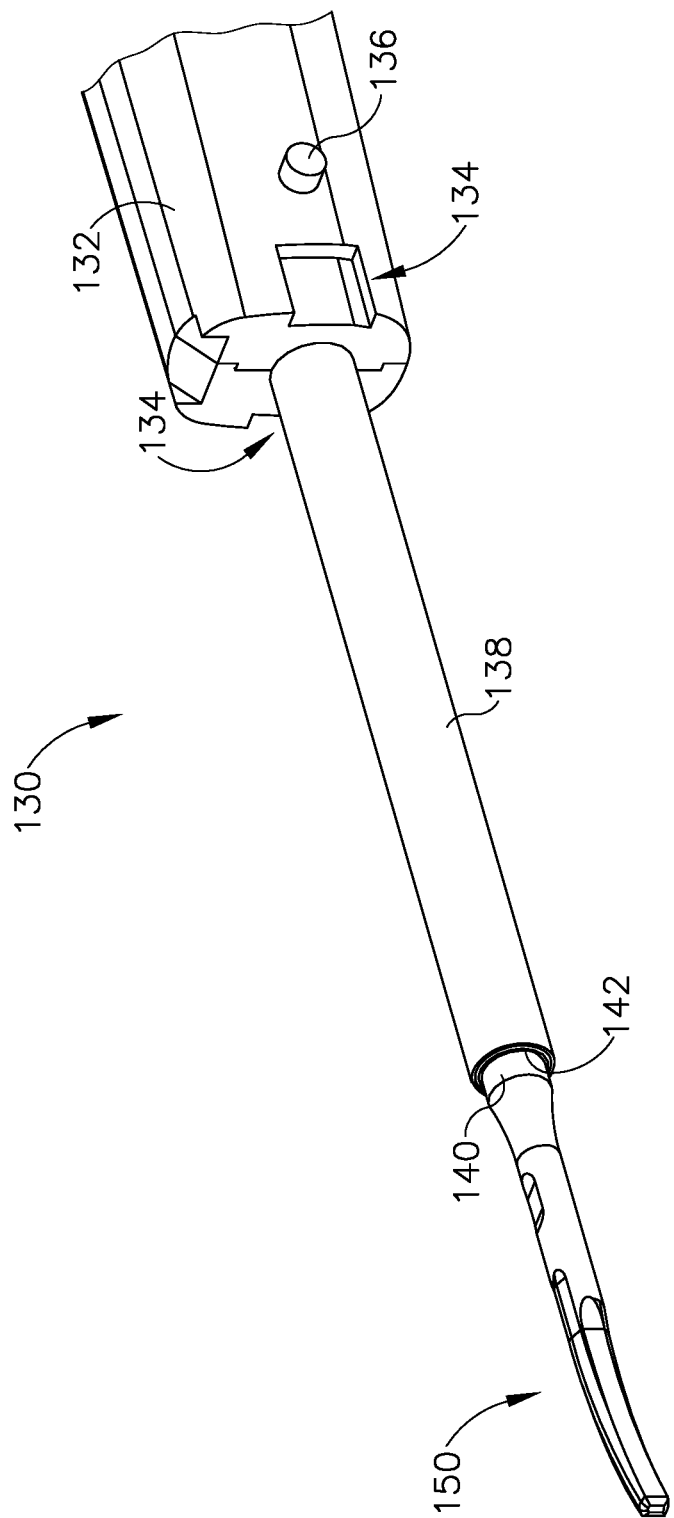
FIG. 5 depicts a perspective view of a shaft assembly and a blade assembly of the first modular assembly of FIG. 3.
Figure 6:
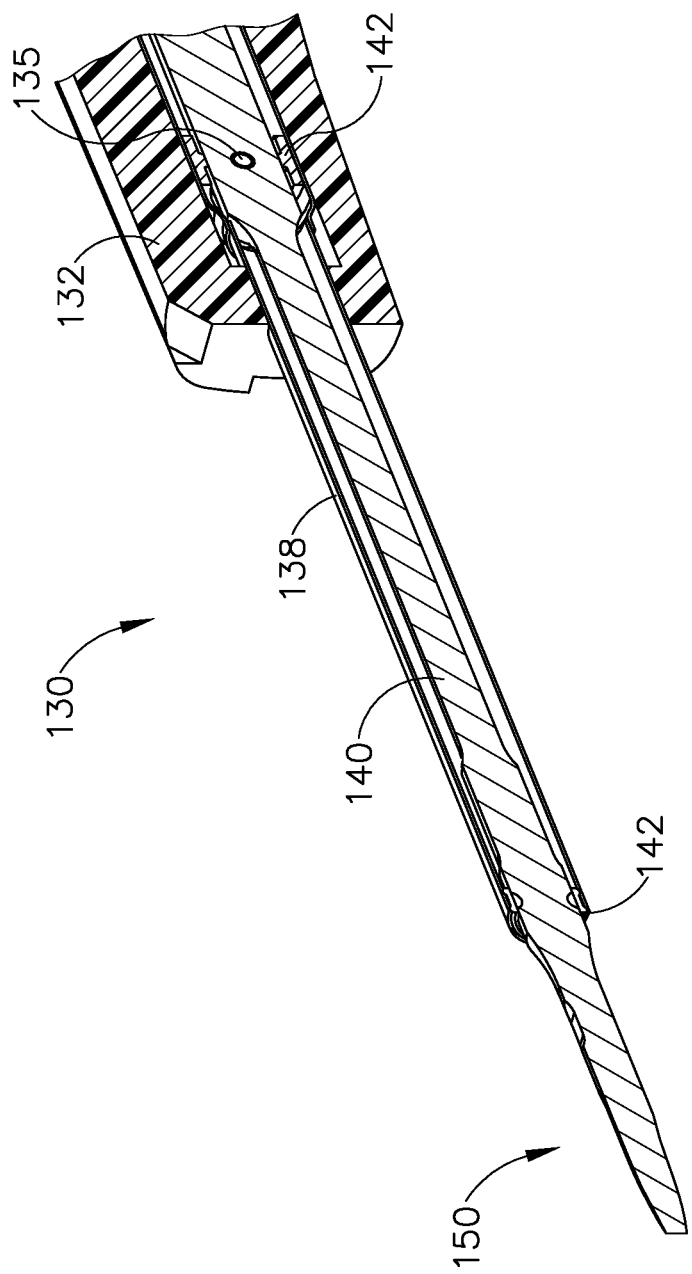
FIG. 6 depicts a cross-sectional perspective view of the shaft assembly and blade assembly of FIG. 5.

Referring to FIG. 4, ultrasonic transducer assembly (30) is housed within body (112) of handle assembly (110). As seen in FIGS. 1A-1B, transducer assembly (30) is coupled with a generator (5) via a plug (11). Transducer assembly (30) receives electrical power from generator (5) and converts that power into ultrasonic vibrations through piezoelectric principles. Generator (5) may include a power source and control module that is configured to provide a power profile to transducer assembly (30) that is particularly suited for the generation of ultrasonic vibrations through transducer assembly (30). Generator (5) may also be configured to provide a power profile that enables end effector (12) to apply RF electrosurgical energy to tissue.

By way of example only, generator (5) may comprise a GEN 300 sold by Ethicon Endo-Surgery, Inc. of Cincinnati, Ohio. In addition or in the alternative, generator (not shown) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. It should also be understood that at least some of the functionality of generator (5) may be integrated into handle assembly (110), and that handle assembly (110) may even include a battery or other on-board power source such that plug (11) is omitted. Still other suitable forms that generator (5) may take, as well as various features and operabilities that generator (5) may provide, will be apparent to those of ordinary skill in the art in view of the teachings herein.

Ultrasonic vibrations that are generated by transducer assembly (30) are communicated along acoustic waveguide (140) when properly coupled. Waveguide (140) is mechanically and acoustically coupled with transducer assembly (30). Waveguide (140) extends through shaft assembly (130) to reach ultrasonic blade (150). Waveguide (140) may be secured to proximal outer sheath (132) and/or body (112) via a pin (135) extending through waveguide (140) and proximal outer sheath (132). Pin (135) may help ensure waveguide (140) remains longitudinally and rotationally fixed relative to the rest of shaft assembly (130) when waveguide (140) is in a deactivated state (i.e. not vibrating ultrasonically).

Additionally, waveguide (140) may be supported by tube (138) via seals (142) located between an interior of tube (138) and an exterior of waveguide (140). Seals (142) may also prevent unwanted matter and fluid from entering portions of tube (138) housing waveguide (140). Pin (135) and seals (142) are located at positions along the length of waveguide (140) corresponding to nodes associated with resonant ultrasonic vibrations communicated through waveguide (140). Therefore, contact between waveguide (140) and pin (135), as well as contact between waveguide (140) and seals (142) may not affect ultrasonic vibrations communicated through waveguide (154).

When ultrasonic blade (150) is in an activated state (i.e., vibrating ultrasonically), ultrasonic blade (150) is operable to effectively cut through and seal tissue, particularly when the tissue is being clamped between clamp pad (222) and ultrasonic blade (150). It should be understood that waveguide (140) may be configured to amplify mechanical vibrations transmitted through waveguide (140). Furthermore, waveguide (140) may include features operable to control the gain of the longitudinal vibrations along waveguide (140) and/or features to tune waveguide (140) to the resonant frequency of the system.

In the present example, the distal end of ultrasonic blade (150) is located at a position corresponding to an anti-node associated with resonant ultrasonic vibrations communicated through waveguide (140), in order to tune the acoustic assembly to a preferred resonant frequency $f_o$ when the acoustic assembly is not loaded by tissue. When transducer assembly (30) is energized, the distal end of ultrasonic blade (150) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through the waveguide to (140) reach ultrasonic blade (150), thereby providing oscillation of ultrasonic blade (150) at the resonant ultrasonic frequency. Thus, when tissue is secured between ultrasonic blade (150) and clamp pad (222), the ultrasonic oscillation of ultrasonic blade (150) may simultaneously sever the tissue and denature the proteins in adjacent tissue cells, thereby providing a coagulative effect with relatively little thermal spread.

In some versions, an electrical current may also be provided through ultrasonic blade (150) and/or clamp pad (222) to also seal the tissue. It should therefore be understood that instrument (10) may also be configured to provide radiofrequency (RF) energy to a surgical site via end effector (12). By way of example only, an operator may rely mainly on the use of ultrasonic energy from blade (150) to sever tissue that is captured between ultrasonic blade (150) and clamp pad (222). The operator may further rely on the use of RF energy from end effector (12) to seal the severed tissue. Of course, it will be understood that the ultrasonic energy from blade (150) may seal tissue to some degree, such that the RF energy from end effector (12) may supplement the sealing that would already be provided from the ultrasonic energy. It will also be understood that there may be instances where the operator may wish to simply use end effector (12) to only apply RF energy to tissue, without also applying ultrasonic energy to tissue. As will be appreciated from the description herein, some versions of instrument (10) are capable of providing all of the above noted kinds of functionality. Various ways in which instrument (10) may be configured and operable to provide both ultrasonic and RF electrosurgical modes of operation are described in various references cited herein; while other ways in which instrument (10) may be configured and operable to provide both ultrasonic and RF electrosurgical modes of operation will be apparent to those of ordinary skill in the art in view of the teachings herein.

An operator may activate buttons (126) to selectively activate transducer assembly (30) to thereby activate ultrasonic blade (150). In the present example, two buttons (126) are provided. In some versions, one button (126) is provided for activating ultrasonic blade (150) at a first power profile (e.g., a first frequency and/or first amplitude) and another button (126) is provided for activating ultrasonic blade (150) at a second power profile (e.g., a second frequency and/or second amplitude). In some other versions, one button (126) is provided for activating ultrasonic blade (150) with ultrasonic energy, and the other button (126) is provided for activating end effector (12) with RF energy. In some other versions, one button (126) is operable to activate ultrasonic blade (150) with ultrasonic energy while simultaneously activating end effector (12) with RF energy; while the other button (126) is only operable to activate ultrasonic blade (150) with ultrasonic energy. In some other versions, at least one button (126) is operable to initially activate ultrasonic blade (150) with ultrasonic energy, then based on one or more other conditions (e.g., time, measured impedance, etc.) while button (126) remains activated, eventually activating end effector (12) with RF energy while still activating ultrasonic blade (150) with ultrasonic energy. In some other versions, at least one button (126) is operable to initially activate ultrasonic blade (150) with ultrasonic energy, then based on one or more other conditions (e.g., time, measured impedance, etc.) while button (126) remains activated, eventually activating end effector (12) with RF energy while ceasing activation of ultrasonic blade (150) with ultrasonic energy. In some other versions, at least one button (126) is operable to initially activate end effector (12) with RF energy, then based on one or more other conditions (e.g., time, measured impedance, etc.) while button (126) remains activated, eventually activating ultrasonic blade (150) with ultrasonic energy while ceasing activation of end effector (12) with RF energy.

It should be understood that any other suitable number of buttons and/or otherwise selectable power levels and/or power modalities may be provided. For instance, a foot pedal may be provided to selectively activate transducer assembly (30).

Buttons (126) of the present example are positioned such that an operator may readily fully operate instrument (10) with a single hand. For instance, when first and second modular assemblies (100, 200) are coupled, the operator may position their thumb in thumb grip ring (214), position their ring finger in finger grip ring (124), position their middle finger about body (112), and manipulate buttons (126) using their index finger. Of course, any other suitable techniques may be used to grip and operate instrument (10); and buttons (126) may be located at any other suitable positions.

Figure 7:
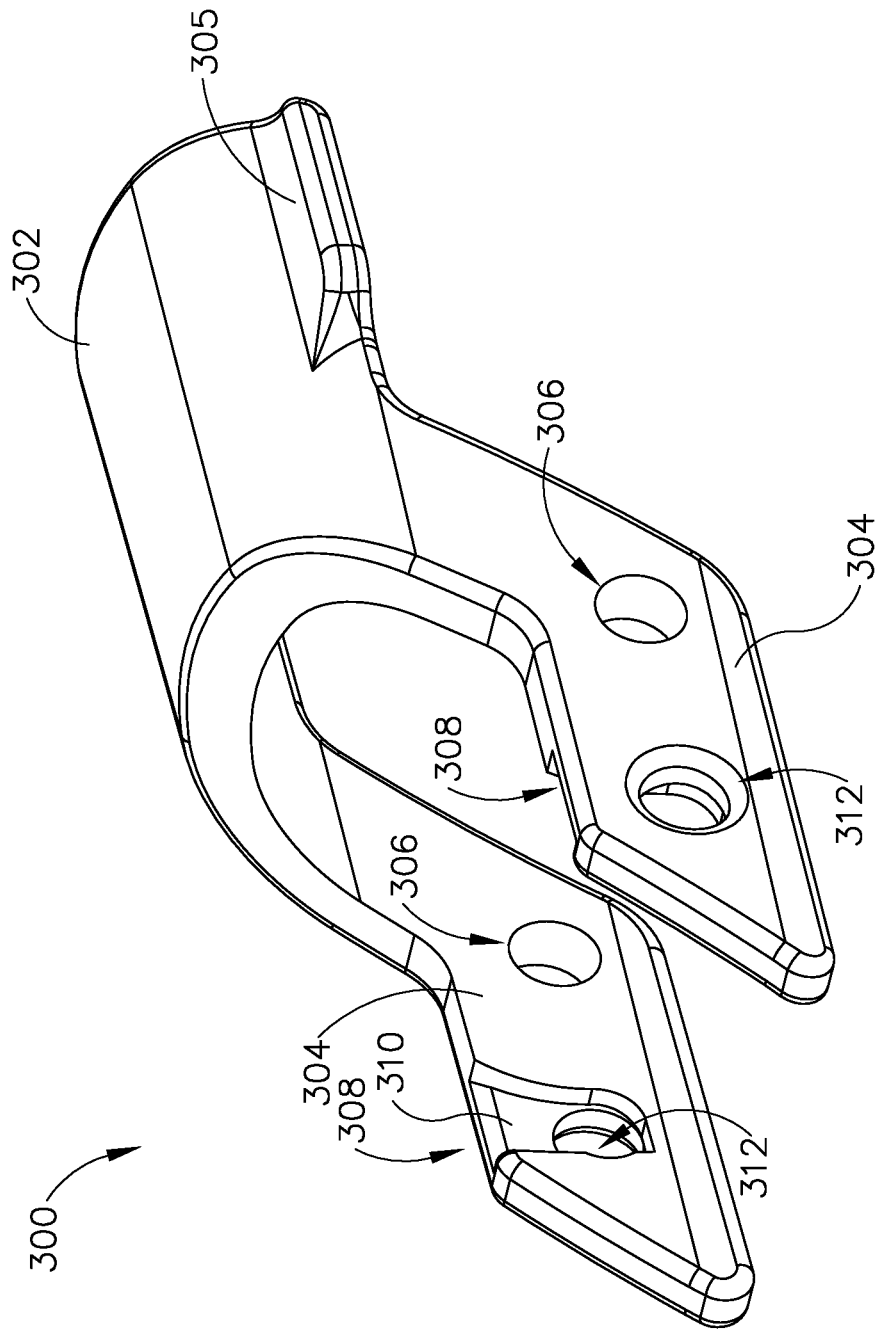
FIG. 7 depicts a perspective view of a coupling member of the instrument of FIG. 1A.
Figure 8:
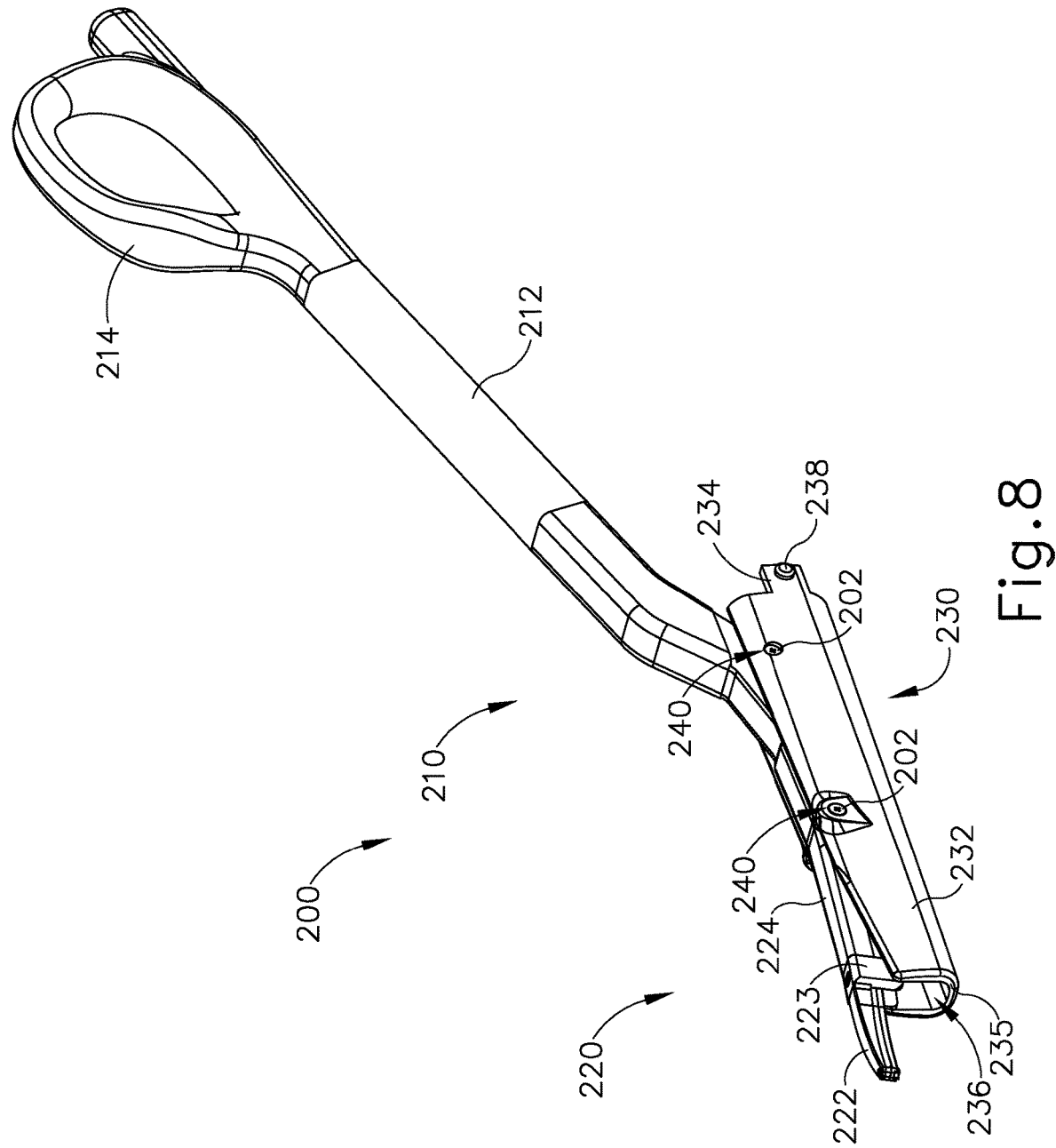
FIG. 8 depicts a perspective view of a second modular assembly of the instrument of FIG. 1A.
Figure 9:
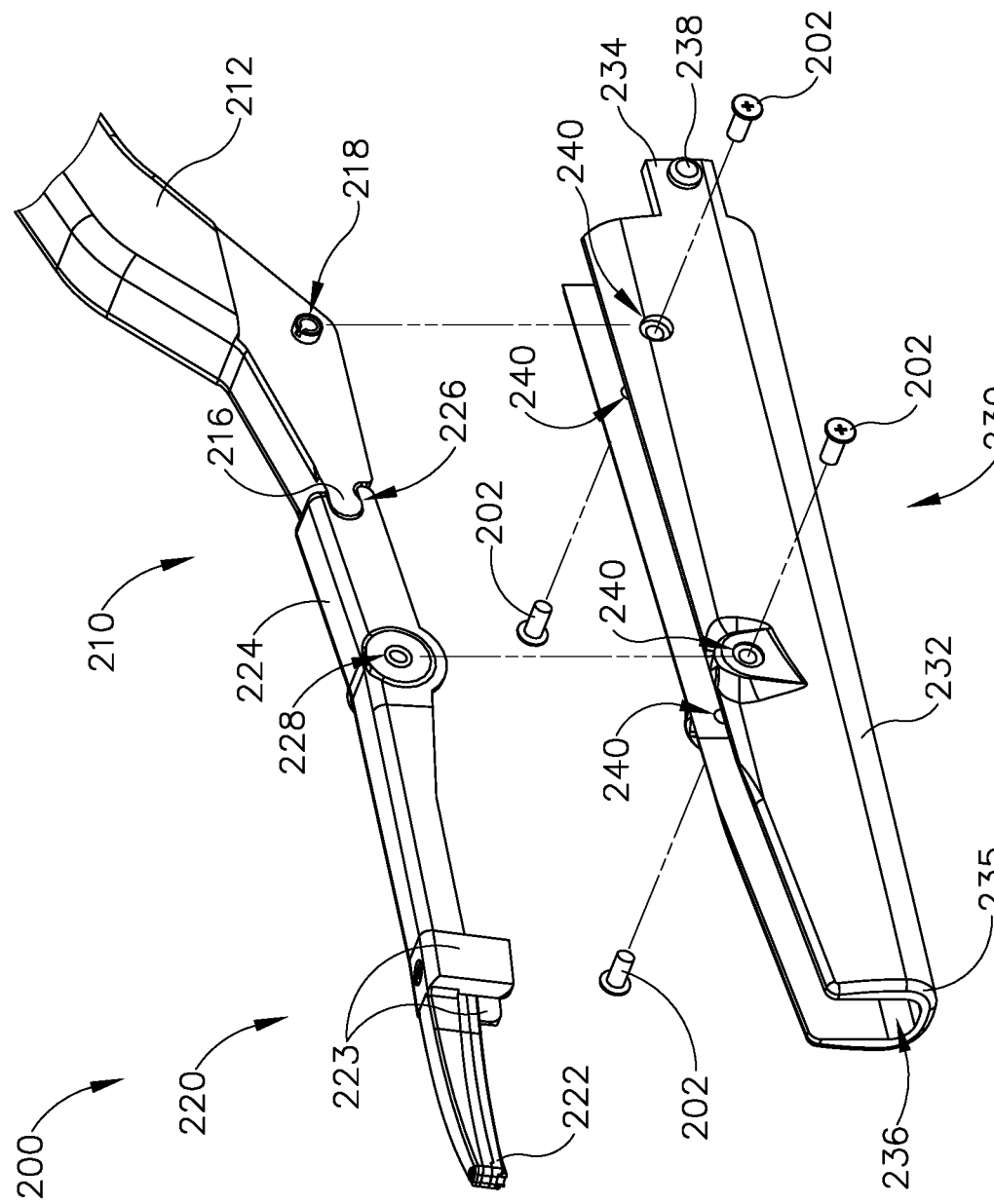
FIG. 9 depicts an exploded perspective view of the second modular assembly of FIG. 8.
Figure 10:
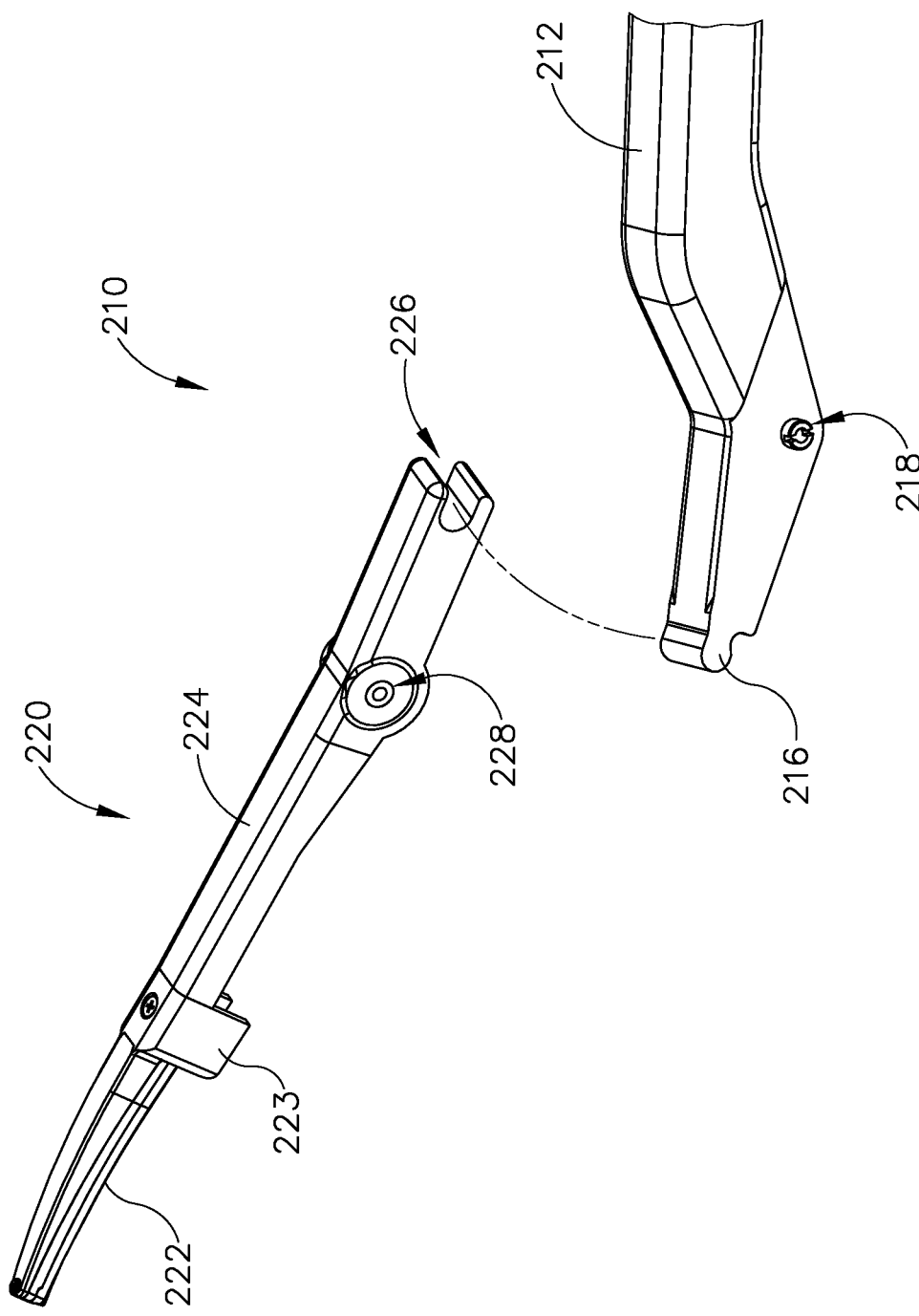
FIG. 10 depicts an exploded perspective view of a clamp arm assembly and a clamp pad assembly of the second modular assembly of FIG. 8.
Figure 11:
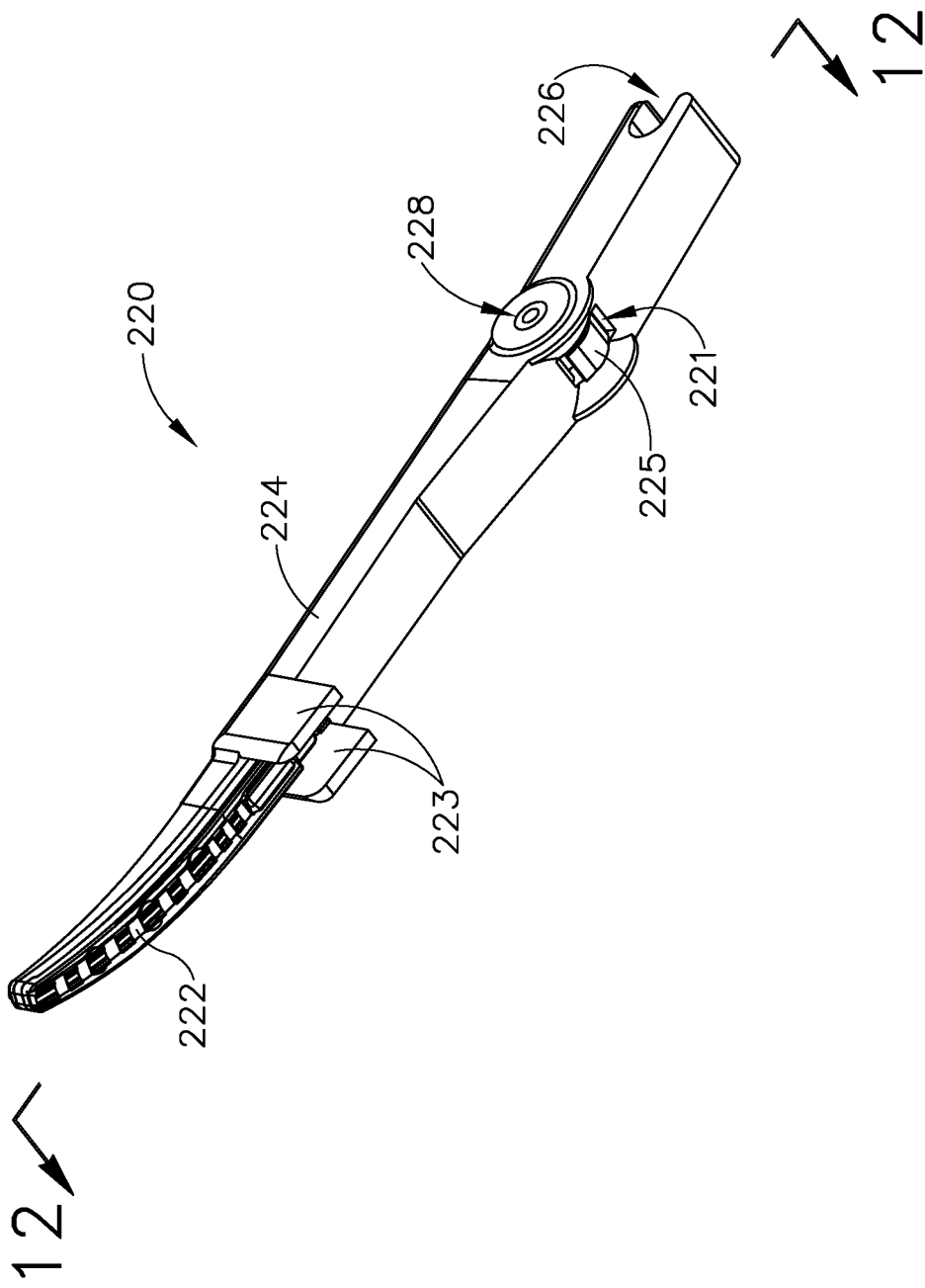
FIG. 11 depicts a perspective view of the clamp arm assembly of FIG. 10.
Figure 12:
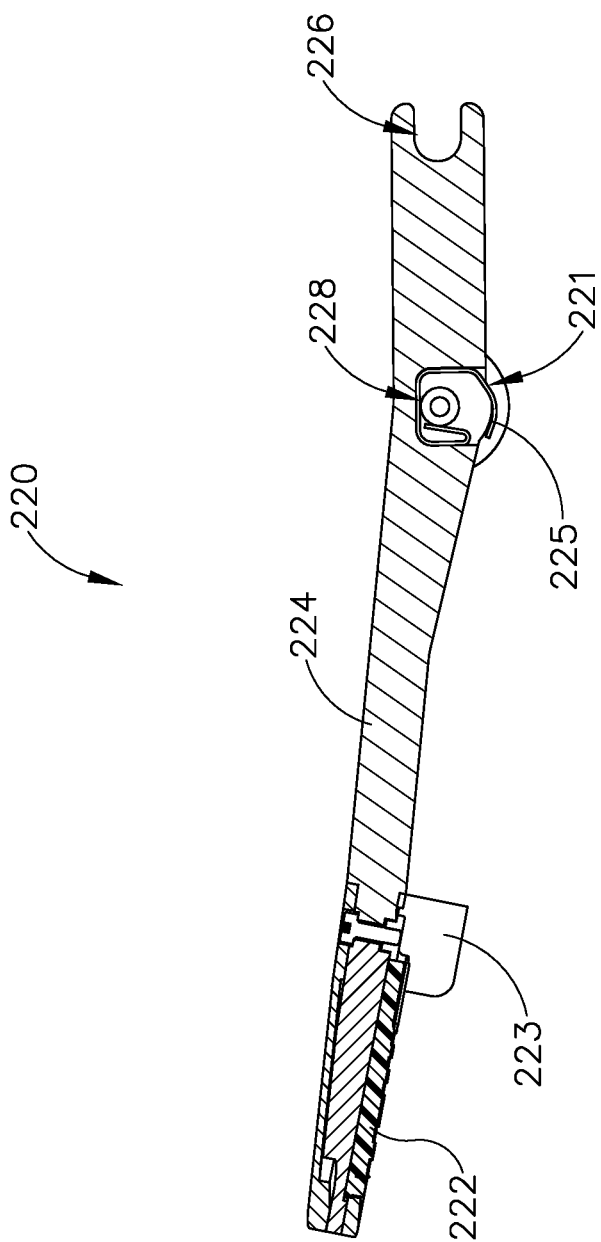
FIG. 12 depicts a cross-sectional side view of the clamp arm assembly of FIG. 10, taken along line 12-12 of FIG. 11.

As mentioned above, and as will be described below, coupling member (300) is configured to selectively couple first modular assembly (100) with second modular assembly (200). As best seen in FIG. 7, coupling member (300) comprises a body (302), a pair of resilient arms (304) extending from body (302), and a pair of grips (305) extending from body (302). Resilient arms (304) each define a respective pivot bore (306) and locking assembly (308). Resilient arms (304) are spaced apart from each other in order to receive proximal outer sheath (132) and to snap-fit pivot bores (306) with respective protrusions (136). Therefore, as shown between FIGS. 13B-13C and 14B-14C, coupling member (300) is configured to pivotally connect with proximal outer sheath (132) via pivot bores (306) and protrusions (136). While in the current example, coupling member (300) and proximal outer sheath (132) are pivotally coupled via snap-fitting, any other type of suitable connection may be used as would be apparent to one having ordinary skill in the art in view of the teachings herein. For example, protrusions (136) may be extendable relative to proximal outer sheath (132) in order to pivotally couple with pivot bore (306) of coupling member (300). Grips (305) may be positioned on body (302) such that an operator may easily rotate coupling member (300) relative to outer sheath (132) via grips (305).

Each locking assembly (308) includes an interior contact wall (310) facing toward each other and a coupling recess (312). As will be described in greater detail below, locking assembly (308) is configured to rotate about pivot bore (306) and protrusions (136) in order to selectively couple with portions of second modular assembly (200).

While coupling member (300) in the current example is used to connect first modular assembly (100) with second modular assembly (200), it should be understood that coupling member (300) may be incorporated into any suitable type of modular assembly that would be apparent to one having ordinary skill in the art in view of the teachings herein. For example, coupling assembly (300) may be modified to couple different modular clamp arm assemblies with first modular assembly (100) where the different modular clamp arm assemblies include clamp arm assemblies such as those taught in U.S. Pub. No. 2017/0105788, entitled "Surgical Instrument with Dual Mode End Effector and Modular Clamp Arm Assembly," published Apr. 20, 2017, issued as U.S. Pat. No. 10,893,914 on Jan. 19, 2021, the disclosure of which is incorporated by reference herein. Thus, one modular clamp arm assembly that may be coupled with first modular assembly (100) may provide pivotal motion of a clamp arm at one side of ultrasonic blade (150) while the other modular clamp arm assembly that may be coupled with first modular assembly (100) may provide pivotal motion of a clamp arm at the other side of ultrasonic blade (150). Other suitable kinds of clamp arm assemblies that may be used to provide different kinds of second modular assemblies (200) will be apparent to those of ordinary skill in the art in view of the teachings herein.

Second modular assembly (200) includes a clamp arm assembly (210), a clamp pad assembly (220), and a distal outer sheath (230). As will be described in greater detail below, distal outer sheath (230) is configured to couple with both coupling member (300) and proximal outer sheath (132) in order to selectively couple first modular assembly (100) with second modular assembly (200). It other words, when properly coupled, proximal outer sheath (132) and distal outer sheath (230) may be fixed relative to one another. As will also be described in greater detail below, clamp arm assembly (210) and clamp pad assembly (220) are both pivotally coupled with distal outer sheath (230). Additionally, clamp arm assembly (210) and clamp pad assembly (220) are dimensioned to mesh with each other such that rotation of one assembly (210, 220) relative to distal outer sheath (230) causes rotation of the other assembly (210, 220) relative to distal outer sheath (230). In other words, clamp arm assembly (210) and clamp pad assembly (220) are capable of rotating each other relative to distal outer sheath (230).

Distal outer sheath (230) includes a U-shaped body (232) extending from a distal face (235) and terminating in a pair of proximally presented projections (234). Proximally presented projections (234) each include a lateral protrusion (238) extending away from U-shaped body (232). U-shaped body (232) defines a longitudinal pathway (236) and a plurality of bores (240). U-shaped body (232) and longitudinal pathway (236) are dimensioned to receive tube (138) and to rotationally house a portion of clamp arm assembly (210) and clamp pad assembly (220). In particular, as best shown between FIGS. 13A-13B, U-shaped body (232) may be inserted over ultrasonic blade (150) and tube (138) such that tube (138) will rest under clamp arm assembly (210) and clamp pad assembly (220). Tube (138) may protect waveguide (140) such that clamp arm assembly (210) and clamp pad assembly (220) do not contact adjacent portions of waveguide (140).

Figure 13A:
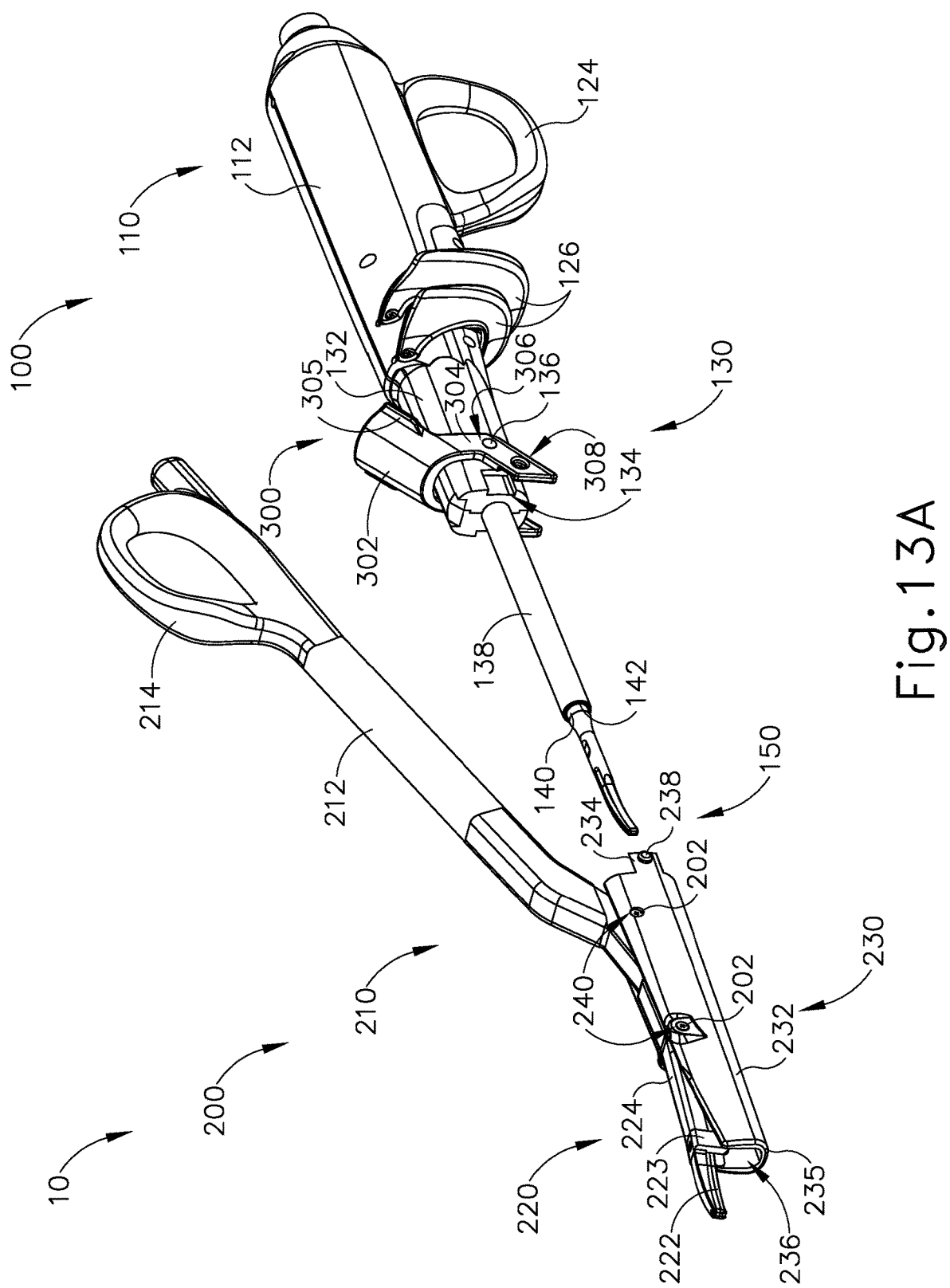
FIG. 13A depicts a perspective view of the second modular assembly of FIG. 8 aligned with the shaft assembly of FIG. 5 in order to couple the modular assemblies together.
Figure 13B:
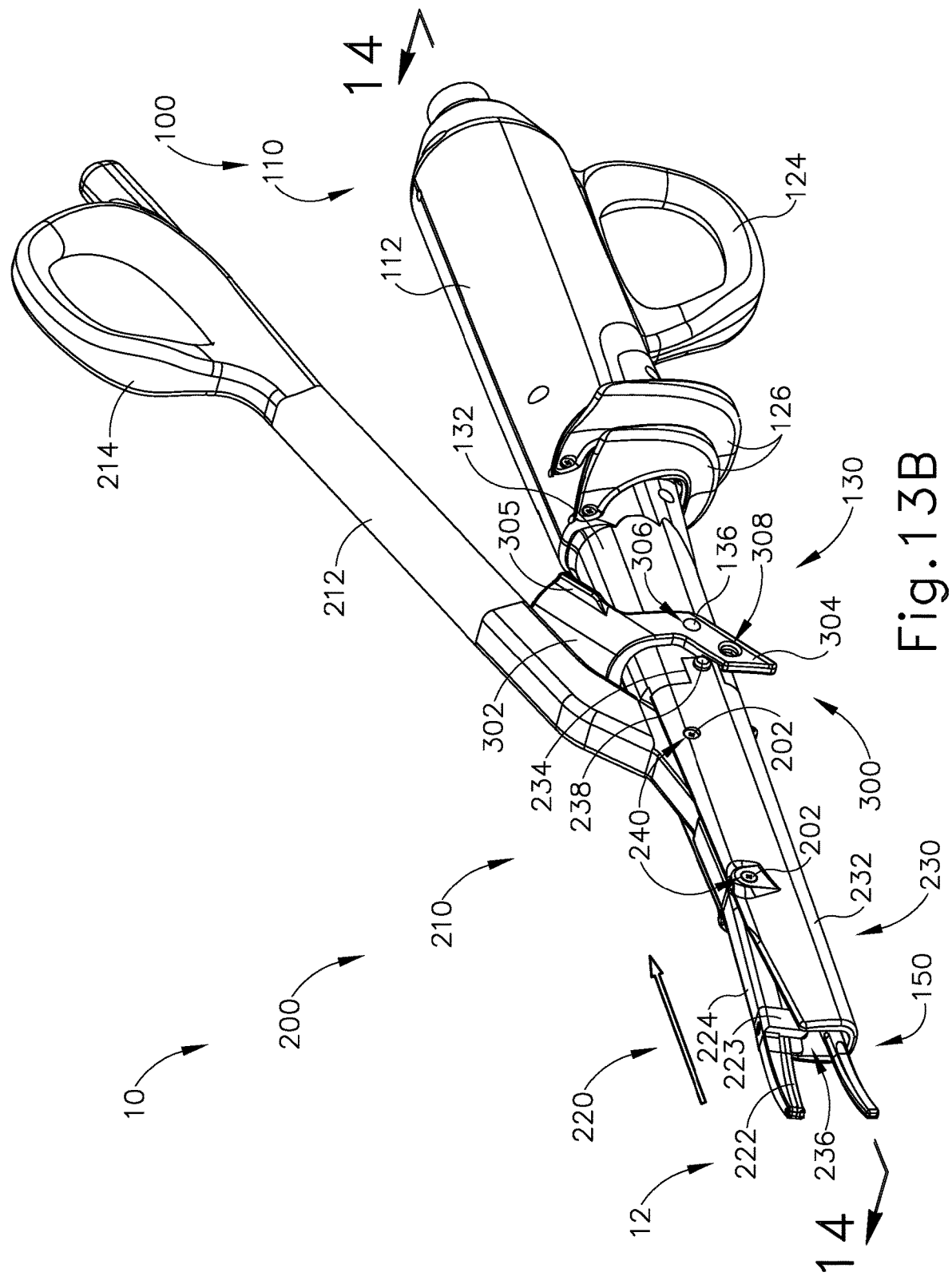
FIG. 13B depicts a perspective view of the second modular assembly of FIG. 8 inserted over the shaft assembly of FIG. 5.
Figure 14A:
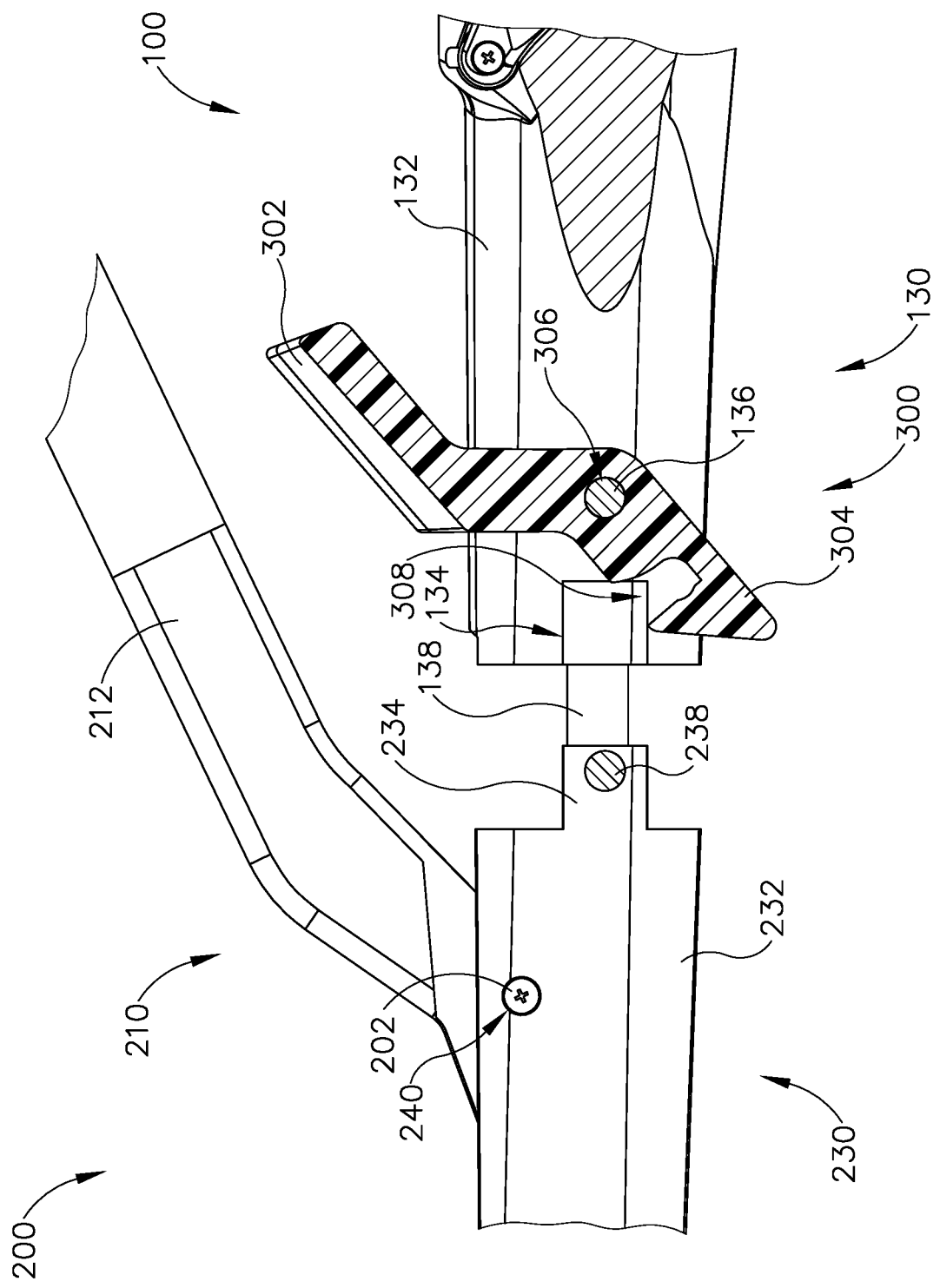
FIG. 14A depicts a cross-sectional side view of the second modular assembly of FIG. 8 partially inserted over the shaft assembly of FIG. 5, taken along line 14-14 of FIG. 13B.
Figure 14B:
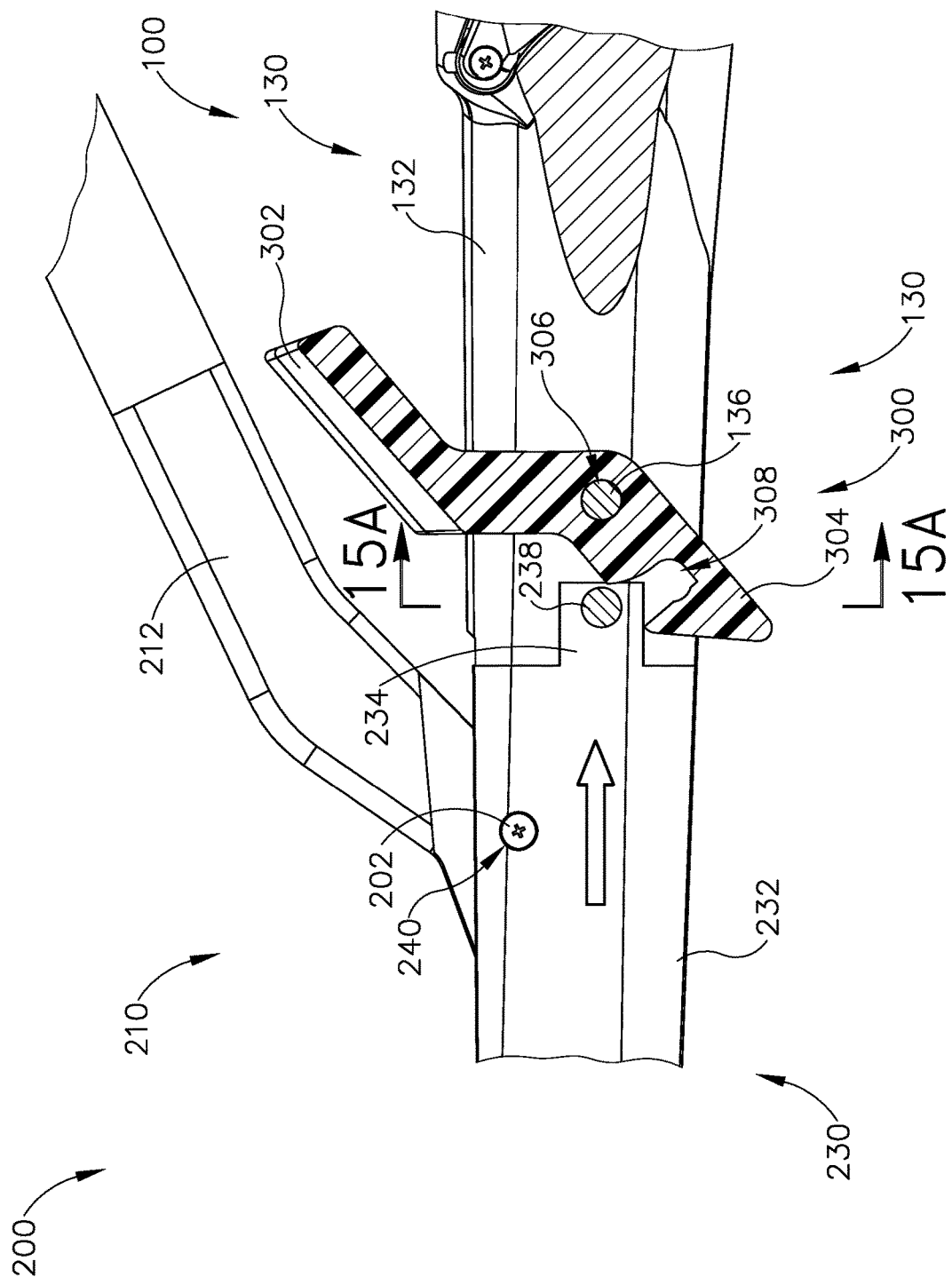
FIG. 14B depicts a cross-sectional side view of the second modular assembly of FIG. 8 further inserted over the shaft assembly of FIG. 5, taken along line 14-14 of FIG. 13B.

As shown between FIGS. 13A-13B and between FIGS. 14A-14B, proximally presented projections (234) are configured to be inserted into recesses (134) defined by proximal outer sheath (132). When proximally presented projections (234) are inserted into recesses (134), distal outer sheath (230) may not rotate relative to proximal outer sheath (132) about a longitudinal axis defined by tube (138). Therefore, proximally presented projections (234) may mate with recesses (134) in order to rotationally fix distal outer sheath (230) relative to proximal outer sheath (132).

Figure 13C:
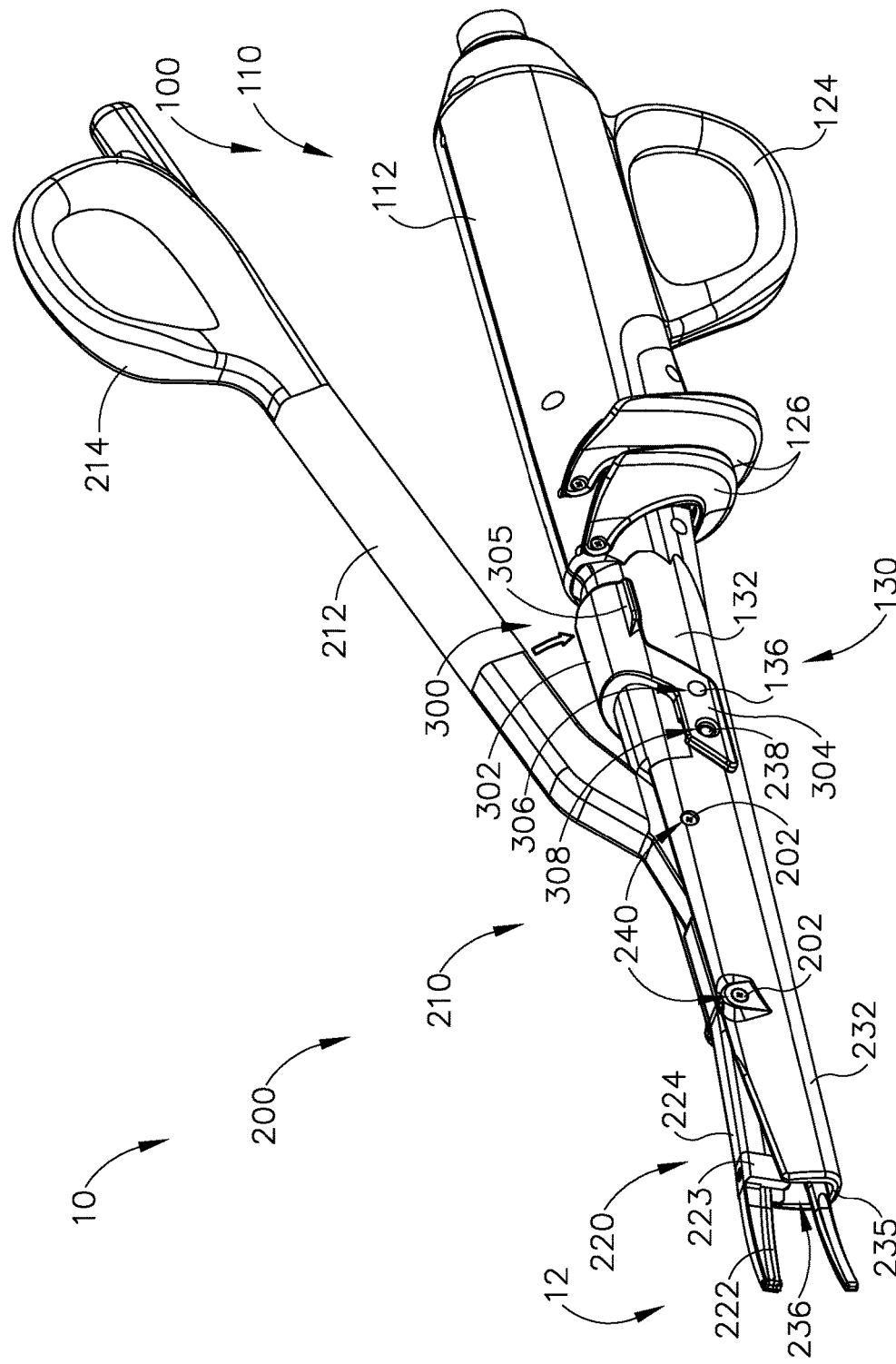
FIG. 13C depicts a perspective view of the second modular assembly of FIG. 8 coupled with the shaft assembly of FIG. 5 via the coupling member of FIG. 7.
Figure 14C:
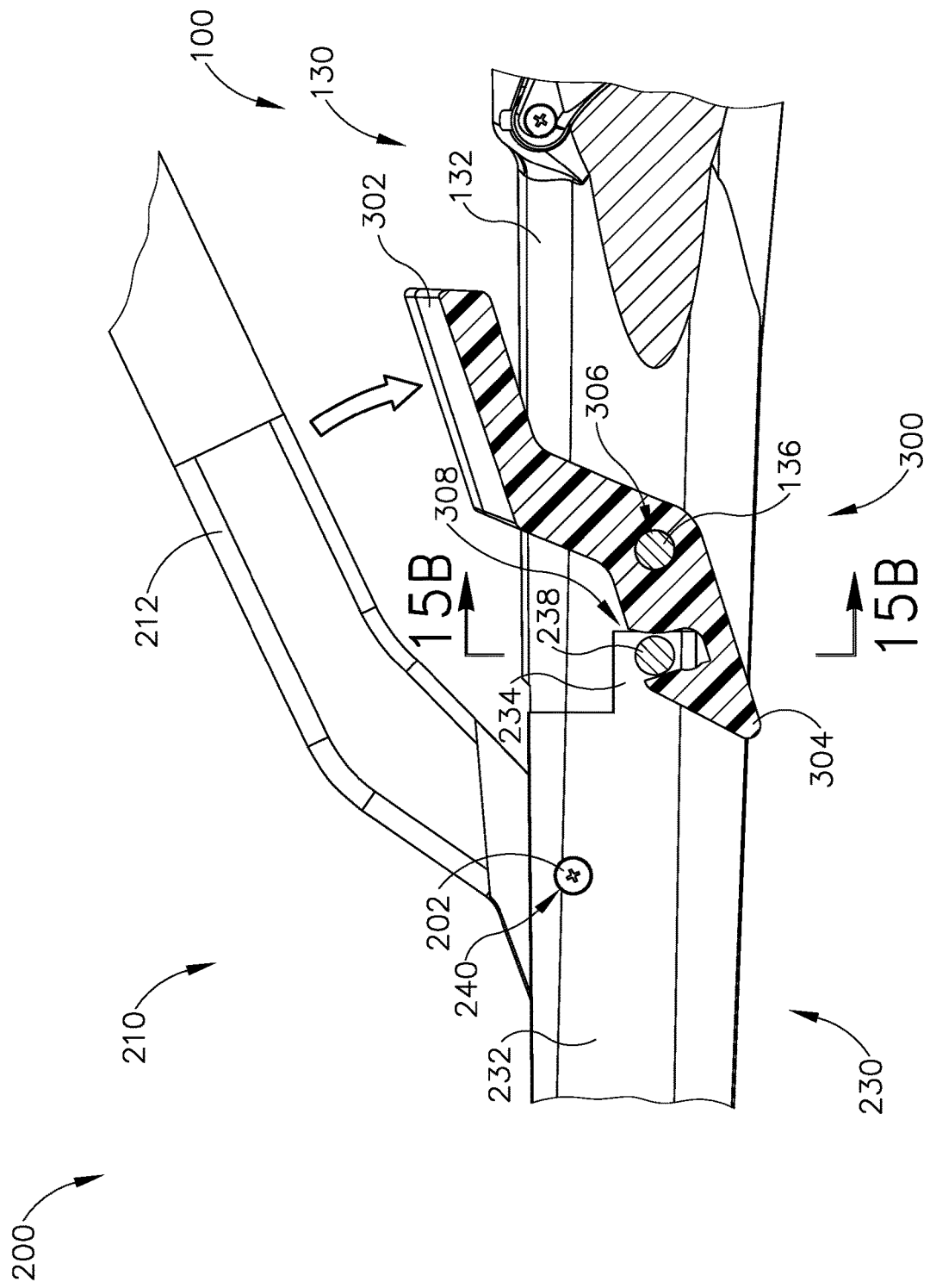
FIG. 14C depicts a cross-sectional side view of the second modular assembly of FIG. 8 inserted over the shaft assembly of FIG. 5 while the coupling member of FIG. 7 is rotated toward a configuration to couple the shaft assembly with the second modular assembly, taken along line 14-14 of FIG. 13B.
Figure 14D:
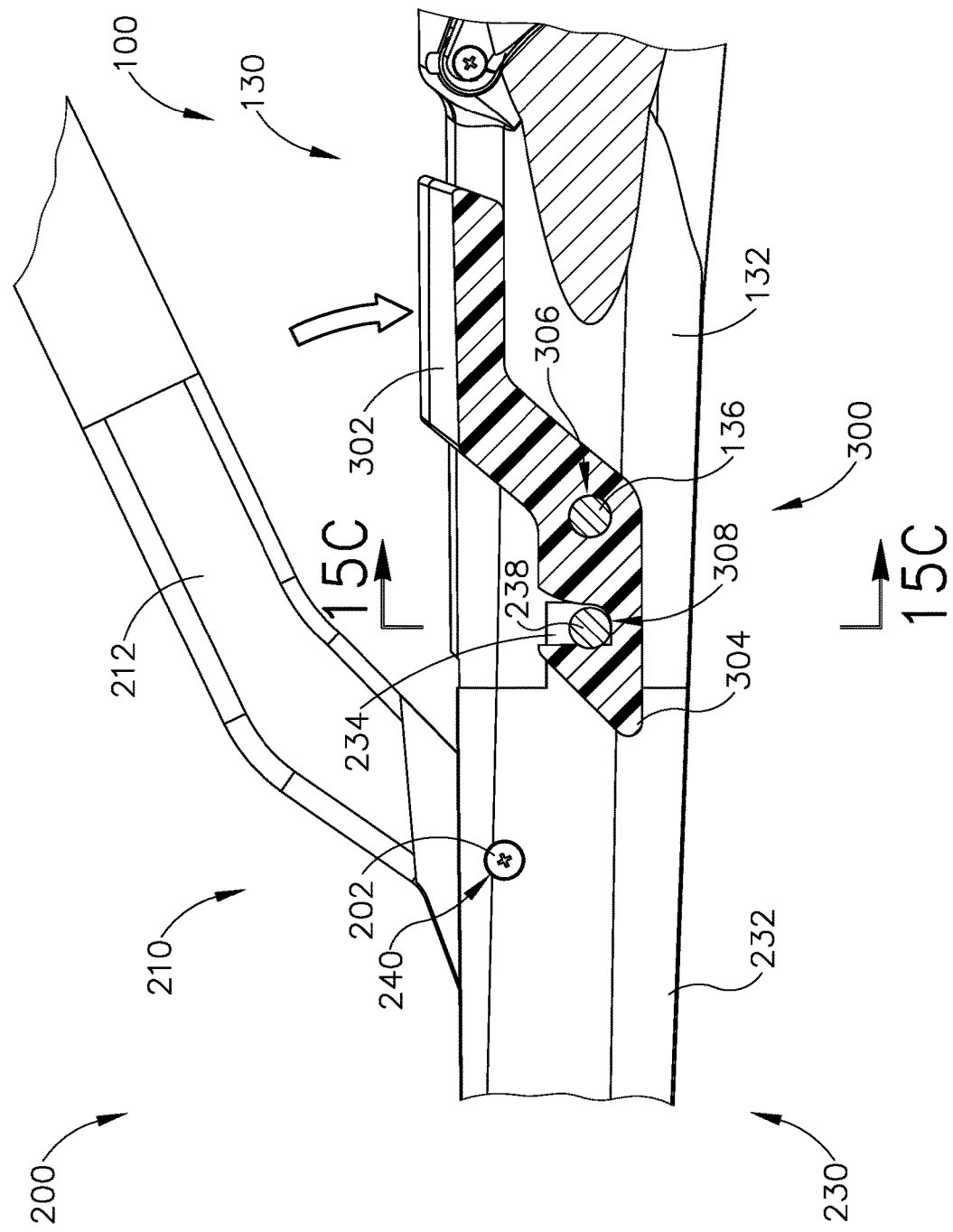
FIG. 14D depicts a cross-sectional side view of the coupling member of FIG. 7 connecting the second modular assembly of FIG. 8 and the shaft assembly of FIG. 5, taken along line 14-14 of FIG. 13B.
Figure 15A:
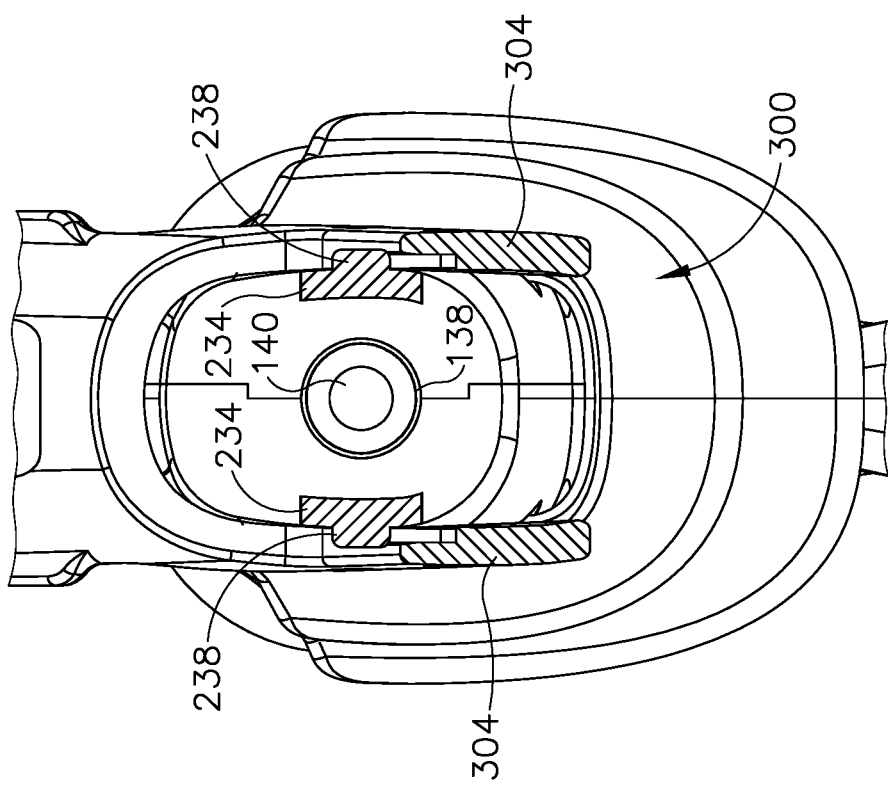
FIG. 15A depicts a cross-sectional front view of the second modular assembly of FIG. 8 inserted over the shaft assembly of FIG. 5, taken along line 15A-15A of FIG. 14B.
Figure 15B:
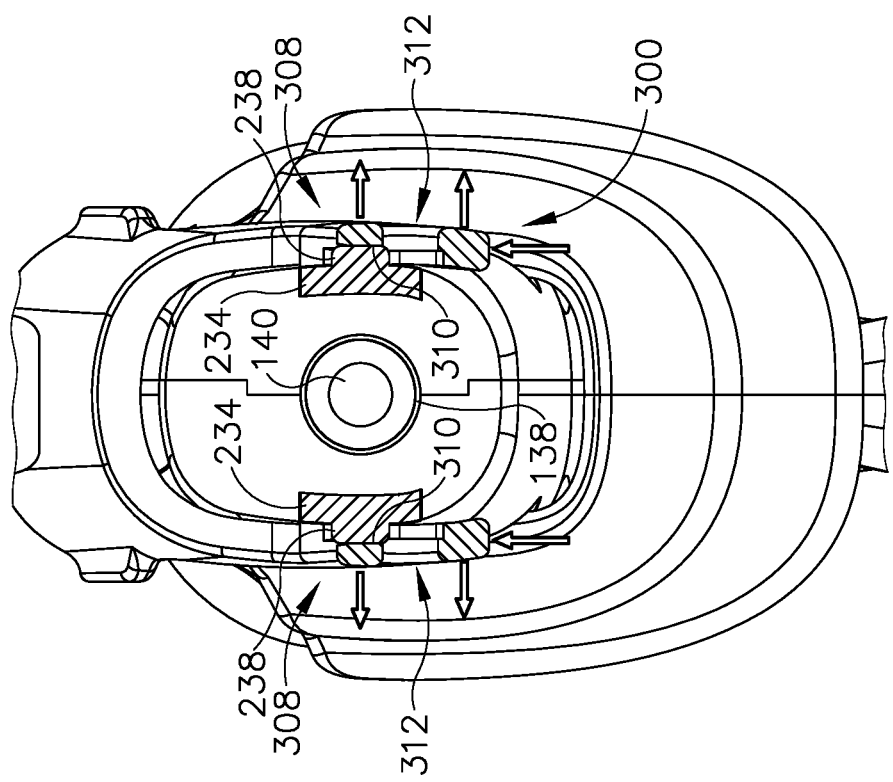
FIG. 15B depicts of cross-sectional front view of the second modular assembly of FIG. 8 inserted over the shaft assembly of FIG. 5 while the coupling member of FIG. 7 is rotated toward a configuration to couple the shaft assembly with the second modular assembly, taken along line 15B-15B of FIG. 14C.
Figure 15C:
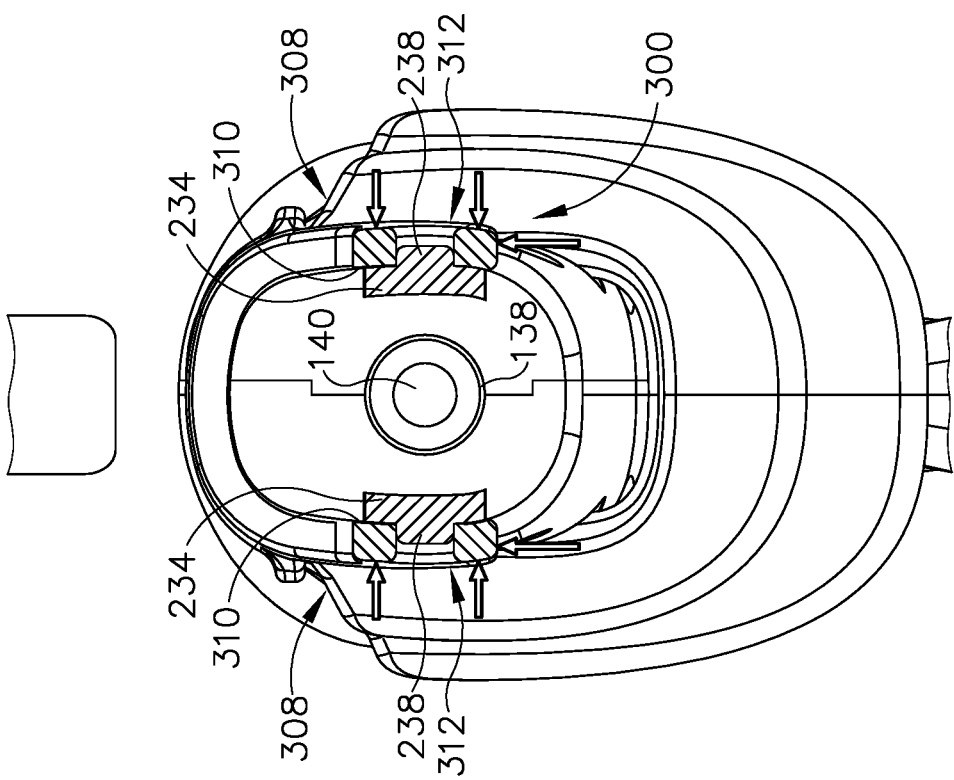
FIG. 15C depicts a cross-sectional front view of the coupling member of FIG. 7 connecting the second modular assembly of FIG. 8 and the shaft assembly of FIG. 5, taken along line 15C-15C of FIG. 14D.

As shown between FIGS. 13B-13C, between FIGS. 14B-14D, and between FIGS. 15A-15C, once distal outer sheath (230) is rotationally fixed relative to proximal outer sheath (132), an operator may rotate coupling member (300) such that locking assembly (308) snap-fits with lateral protrusions (238). In particular, an operator may rotate coupling member (300) about protrusion (136) such that lateral protrusions (238) cam against contact walls (310) of resilient arms (304). As a result, as best seen in FIG. 15B, contact between contact walls (310) and lateral protrusions (238) flex resilient arms (304) outwardly away from proximally presented projections (234). An operator may further rotate coupling member (300) about protrusions (136) such that lateral protrusions (238) no longer abut against contact wall (310), as shown in FIGS. 13C, 14C, and 15C. The resilient nature of resilient arms (304) allows resilient arms (304) to return to a relaxed position such that lateral protrusions (238) rest within coupling recess (312) of locking assembly (308). With locking assembly (308) of coupling member (300) fully attached, and shown in FIGS. 13C, 14D, and 15C, distal outer sheath (230) is longitudinally fixed relative to proximal outer sheath (132), thereby coupling first modular assembly (100) with second modular assembly (200).

If an operator wishes to decouple first modular assembly (100) with second modular assembly (200), an operator may grasp grips (305) to rotate coupling member (300) in the opposite direction about protrusions (136) in order to flex resilient arms (304) to pop out lateral protrusions (238) from coupling recess (312).

As mentioned above, clamp arm assembly (210) and clamp pad assembly (220) are both pivotally coupled with distal outer sheath (230) such that rotation of one assembly (210, 220) relative to distal outer sheath (230) causes rotation of the other assembly (210, 220) relative to distal outer sheath (230).

Clamp arm assembly (210) includes an elongated arm (212), a thumb grip ring (214), a camming protrusion (216), and a pivot coupling (218). Thumb grip ring (214) and elongated arm (212) together provide a scissor grip type configuration in combination with body (112) and finger grip ring (124). Pivot coupling (218) pivotally couples clamp arm assembly (210) with distal outer sheath (230) via pins (202). As will be described in greater detail below, camming protrusion (216) interacts with clamp pad assembly (220) in order to rotate clamp pad assembly (220) in response to rotation of clamp arm assembly (210).

Clamp pad assembly (220) includes a clamp pad (222) facing ultrasonic blade (150), a pair of tissue stops (223) located adjacent to ultrasonic blade (150) and proximal to clamp pad (222), an arm (224) defining both a camming recess (226) and a spring recess (221), a pivot coupling (228), and a leaf spring (225) housed within spring recess (221). In some versions, clamp pad assembly (220) further includes one or more electrodes that is/are operable to apply RF electrosurgical energy to tissue. Various references herein provide examples of how a clamp pad assembly may incorporate one or more electrodes that is/are operable to apply RF electrosurgical energy to tissue, while other examples of how clamp pad assembly (220) may incorporate one or more electrodes that is/are operable to apply RF electrosurgical energy to tissue will be apparent to those of ordinary skill in the art in view of the teachings herein.

In the current example, tissue stops (223) longitudinally align with distal face (235) when end effector (12) is in the closed position. Tissue stops (223) and distal face (235) may cooperate to consistently and simply prevent tissue from inadvertently reaching a proximal position within end effector (12) where ultrasonic energy from blade (150) may not adequately sever or seal the tissue. In providing such prevention, tissue stop (223) may eliminate the need for an operator to visualize proximal region of end effector (12) in order to determine whether the tissue has reached an undesirably proximal position within end effector (12).

Camming protrusion (216) is dimensioned to rotate within camming recess (226) while also contacting camming recess (226). Camming protrusion (216) and camming recess (226) are positioned within distal outer sheath (230) such that both are located between pivot couplings (218, 228) while clamp arm assembly (210) and clamp pad assembly (220) are pivotally coupled to distal outer sheath (230). Therefore, as shown between FIGS. 1A-1B and 16A-16B, when an operator rotates elongated arm (212) about pivot coupling (218) toward distal outer sheath (230), camming protrusion (216) rotates away from distal outer sheath (230) about pivot coupling (218). Because camming protrusion (216) is housed within camming recess (226), upward movement of camming protrusion (216) about pivot coupling (218) causes upward movement of camming recess (226) about pivot coupling (228). Upward movement of camming recess (226) about pivot coupling (228) rotates arm (224) such that clamp pad (222) rotates toward ultrasonic blade (150). Therefore, closure of elongated arm (212) of clamp arm assembly (210) toward handle assembly (110) leads to closure of clamp pad (222) toward ultrasonic blade (150). It should therefore be understood that when first modular assembly (100) and second modular assembly (200) are connected, an operator may squeeze thumb grip ring (214) toward body (112) to thereby clamp tissue between clamp pad assembly (220) and ultrasonic blade (150) to compress tissue against ultrasonic blade (150). When ultrasonic blade (150) is activated during such compression, clamp pad assembly (220) and ultrasonic blade (150) cooperate to transect and/or seal the compressed tissue.

As mentioned above, leaf spring (225) is housed within spring recess (221). As best seen in FIGS. 16A-16B, leaf spring (225) is dimensioned such that a portion of leaf spring (225) extends out of spring recess (221) to make contact against tube (138) in order to provide electrical continuity between the one or more RF electrodes of end effector (12) and the source of electrical power. It should be understood that leaf spring (225) maintains this electrical continuity throughout the range of motion of clamp pad assembly (220). It should also be understood that any other suitable kinds of features may be used to provide electrical continuity between the one or more RF electrodes of end effector (12) and the source of electrical power.

In some versions, one or more resilient members are used to bias clamp pad assembly (220) toward the open position shown in FIGS. 1A and 16A. Of course, any other suitable kind of resilient member may be used as would be apparent to one having ordinary skill in the art in view of the teachings herein, such as a torsion spring. Alternatively, clamp pad assembly (220) need not necessarily be biased toward the open position.

Pivot couplings (218, 228) of clamp arm assembly (210) and clamp pad assembly (220) being located within longitudinal pathway (236) of distal outer sheath (230) may provide certain desirable advantages as compared to clamp arm assembly (210) and clamp pad assembly (220) pivotally coupling with an exterior of distal outer sheath (230). For instance, there may be a reduced chance of inadvertently pinching tissue due to rotation of clamp arm assembly (210) and clamp pad assembly (220) with pivot couplings (218, 228) being housed within U-shaped body (232). In other words, U-shaped body (232) may protect tissue from being inadvertently pinched by rotation of clamp arm assembly (210) and clamp pad assembly (220) relative to distal outer sheath (230). Additionally, the width of second modular assembly (200) may be reduced due to pivot couplings (218, 228) being housed within longitudinal pathway (236) of distal outer sheath (230). It may also be easier to fabricate desired components due to the simplified shapes of clamp arm assembly (210) and clamp pad assembly (220). A reduction of tolerance stack may also be an advantage to storing pivot couplings (218, 228) within the interior of distal outer sheath (230).

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. Nos. 9,023,071; 8,461,744; 9,381,058; U.S. Pub. No. 2012/0116265, now abandoned; U.S. Pat. Nos. 9,393,037; 9,095,367; and/or U.S. Pub. No. 2015/0080925, entitled "Alignment Features for Ultrasonic Surgical Instrument," published Mar. 19, 2015, now abandoned, the disclosure of which is incorporated by reference herein.

Figure 17:
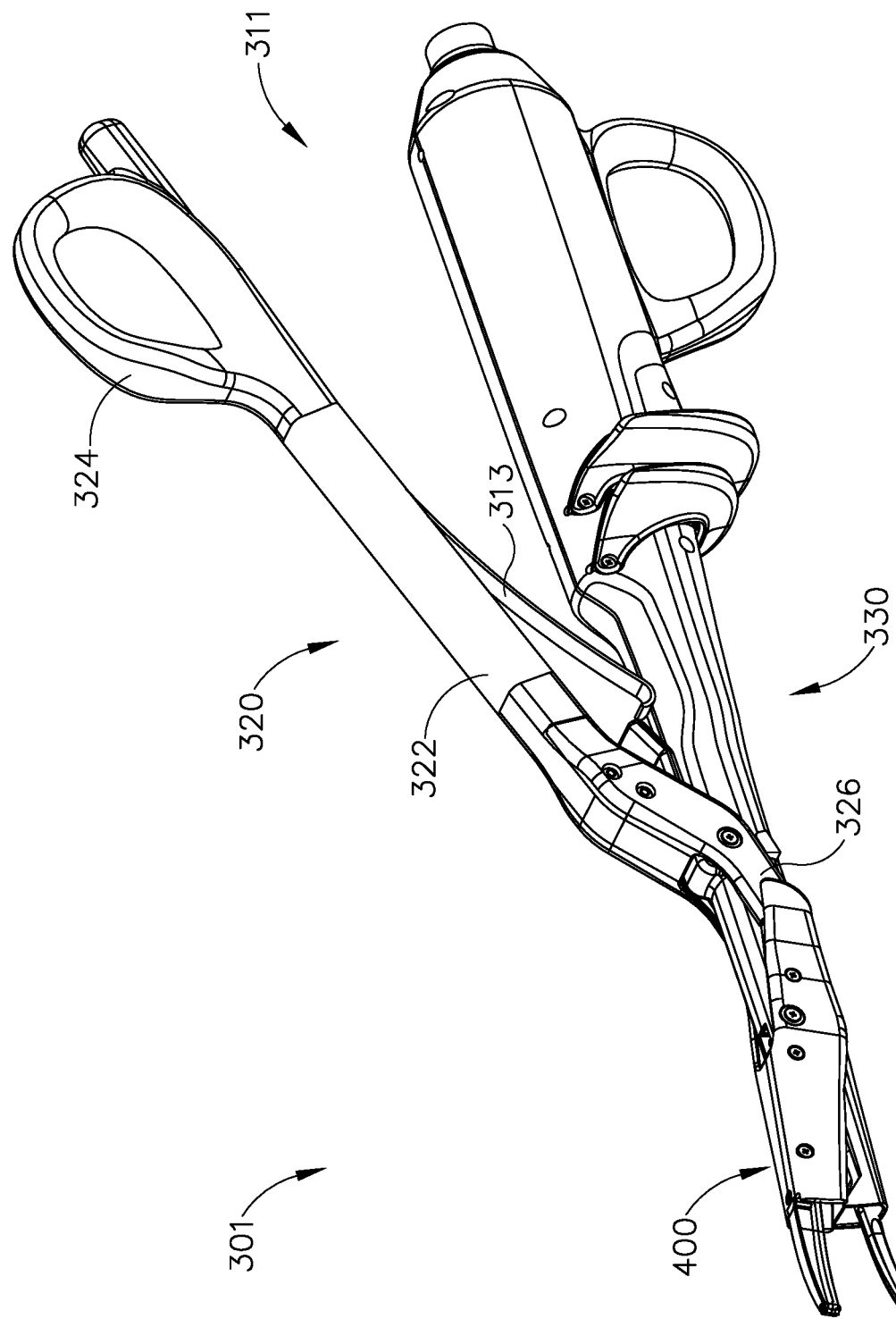
FIG. 17 depicts a perspective view of a second exemplary surgical instrument, with an end effector of the instrument in an open configuration.
Figure 18:
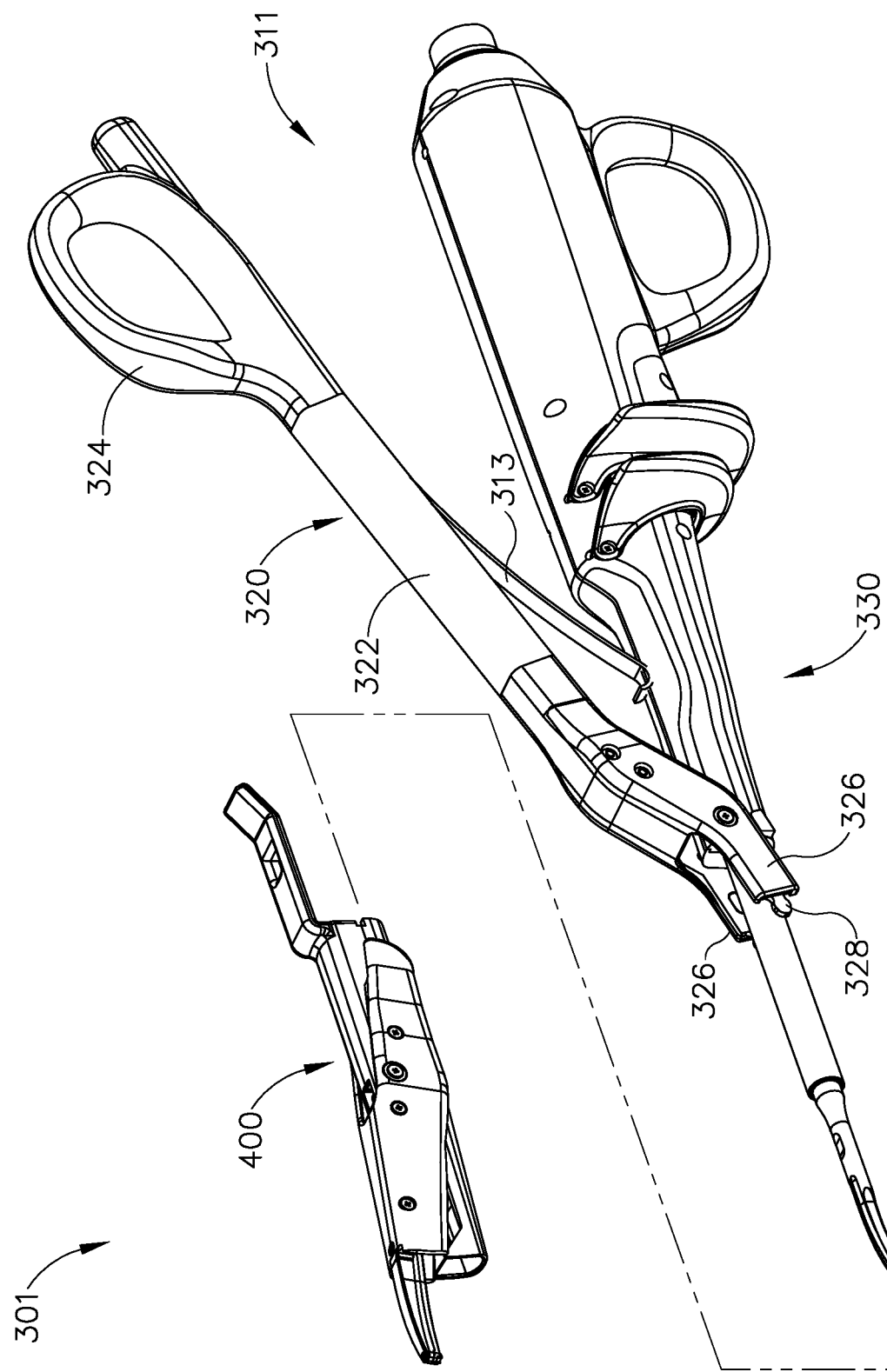
FIG. 18 depicts a partially exploded perspective view of the instrument of FIG. 17.

II. Second Exemplary Ultrasonic Surgical Instrument for Open Surgical Procedures FIGS. 17-18 show a second exemplary ultrasonic surgical instrument (301). Except as otherwise described below, instrument (301) of this example may be constructed and operable just like instrument (10) described above. Certain details of instrument (301) will therefore be omitted from the following description, it being understood that such details are already provided above in the description of instrument (10).

Instrument (301) of the present example comprises a handle assembly (311), a clamp arm actuator (320), a shaft assembly (330), and a clamp arm assembly (400). Handle assembly (311) of this example is configured and operable just like handle assembly (110) described above, such that details of handle assembly (311) will not be reiterated here.

Figure 19:
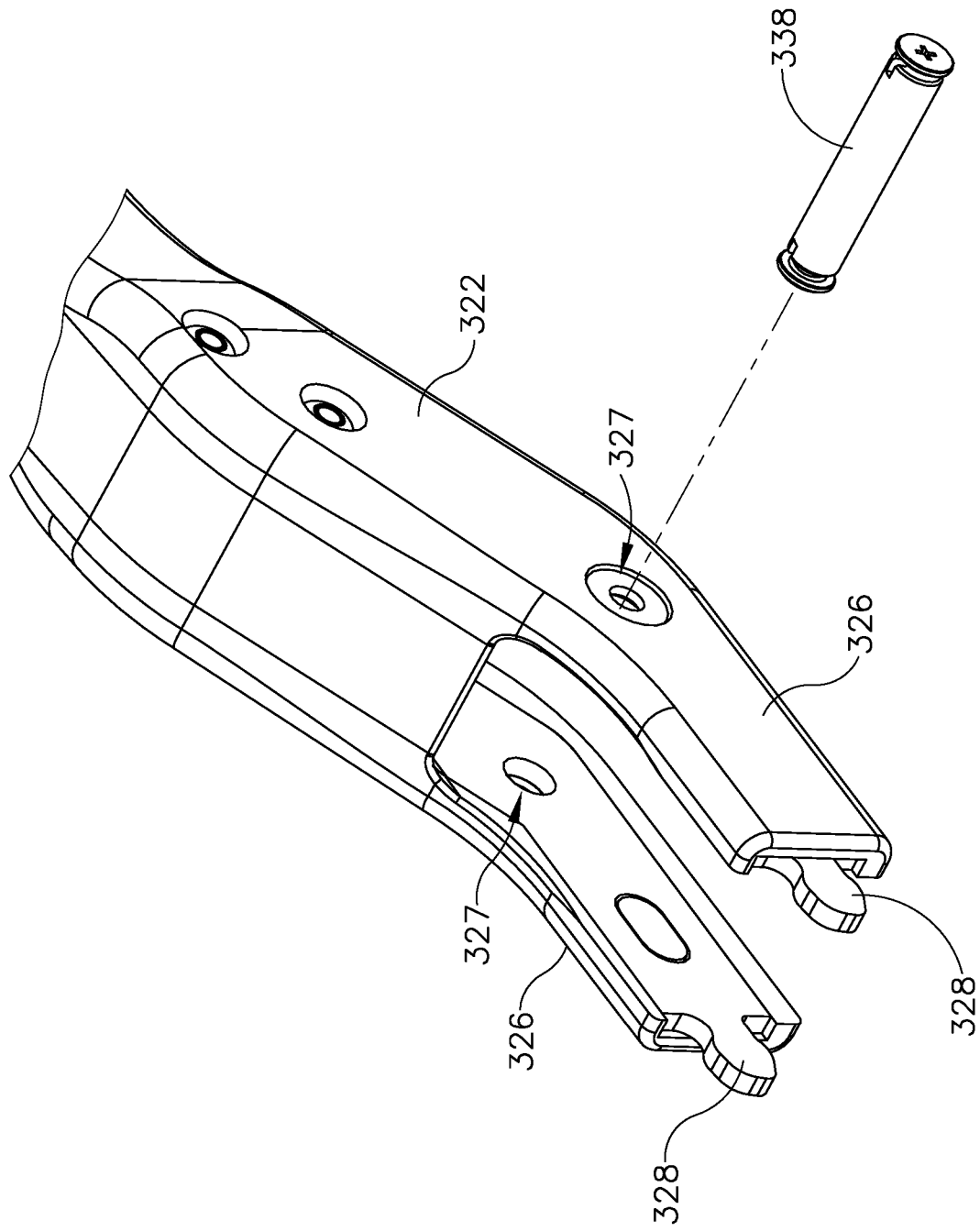
FIG. 19 depicts a partial perspective view of the distal end of a clamp arm actuator of the instrument of FIG. 17.

Clamp arm actuator (320) is pivotably coupled with shaft assembly (330). In the present example, clamp arm actuator (320) is not removable from shaft assembly (330). Clamp arm actuator (320) of the present example comprises a shaft (322). A thumb ring (324) is positioned at the proximal end of shaft (322). As best seen in FIGS. 18-19, pair of projections (326) extend distally from shaft (322). Projections (326) are laterally spaced apart from each other and extend parallel to each other. As best seen in FIG. 19, the distal end of each projection (326) includes a camming protrusion (328). Camming protrusions (328) are configured to cooperate with clamp arm assembly (400), in a manner similar to camming protrusions (216), as will be described below. As also best seen in FIG. 19, projections (326) also define a pair of pin openings (327), which are configured to receive pin (338). Pin (338) provides a pivotable coupling between clamp arm actuator (320) and shaft assembly (330).

Figure 20:
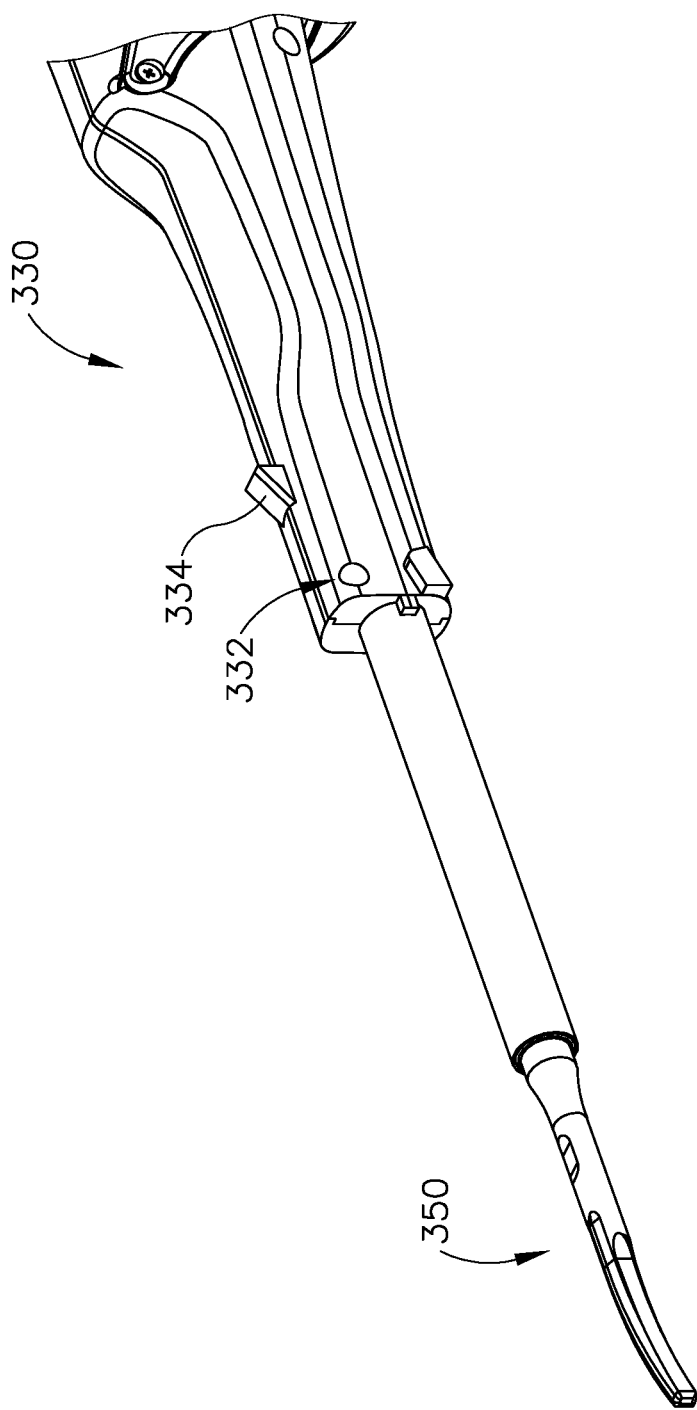
FIG. 20 depicts a perspective view of a shaft assembly and ultrasonic blade of the instrument of FIG. 17.

Shaft assembly (330) extends distally from handle assembly (311) and is substantially identical to shaft assembly (130) described above except for the differences described below. An ultrasonic blade (350), which is identical to ultrasonic blade (150) described above, is positioned at the distal end of shaft assembly (130). As best seen in FIG. 20, shaft assembly (330) defines an opening (332) that is configured to receive pin (338) to thereby provide a pivotable coupling between clamp arm actuator (320) and shaft assembly (330). As also shown in FIG. 20, shaft assembly (330) includes a ramped latch protrusion (334), which is configured to engage clamp arm assembly (400) as will be described in greater detail below.

Figure 21:
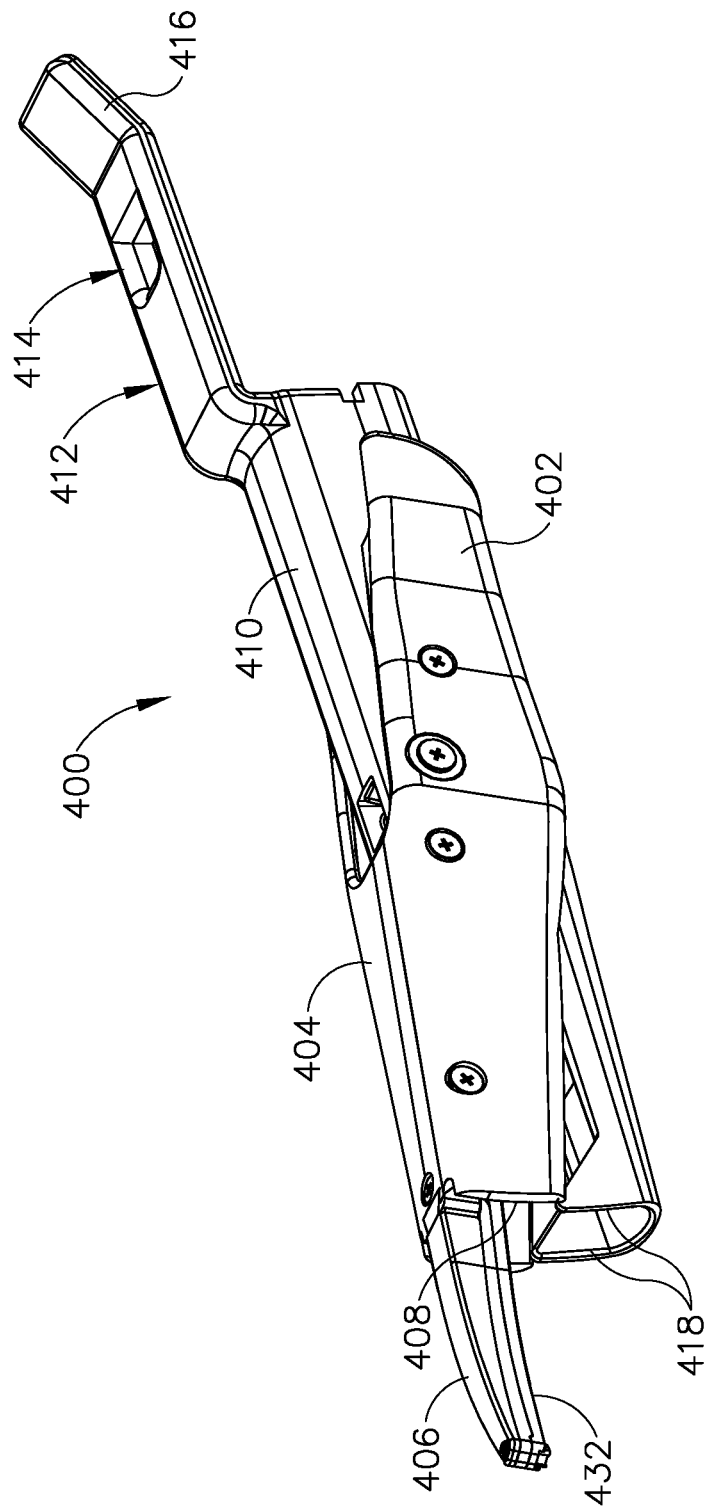
FIG. 21 depicts a perspective view of a removable clamp arm assembly of the instrument of FIG. 17.
Figure 22:
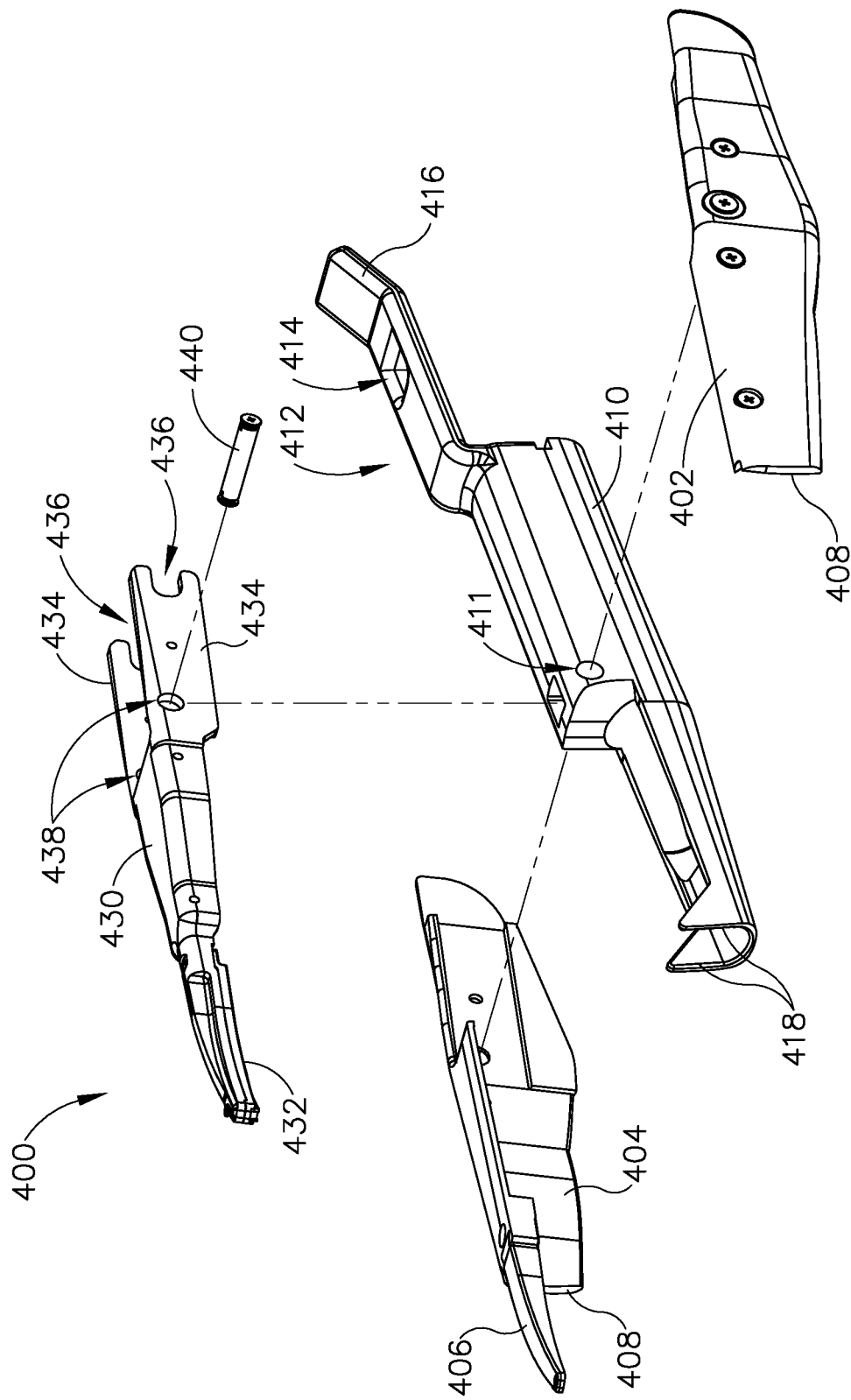
FIG. 22 depicts an exploded perspective view of the clamp arm assembly of FIG. 21.

As shown in FIGS. 21-22, clamp arm assembly (400) of the present example comprises a pair of shrouds (402, 404) partially encompassing a clamp arm body (430), which is pivotally coupled with a stationary body (410). Each shroud includes a distally presented tissue stop edge (408). Stationary body (410) also includes a pair of distally presented tissue stop edges (418). Edges (408, 418) are configured to cooperate to consistently and restrict proximal positioning of tissue like tissue stops (223) and distal face (235) described above. Shroud (404) of the present example also includes a distally projecting shield member (406).

Stationary body (410) of the present example further includes a pin opening (411) and a proximally projecting latch member (412). Latch member (412) defines a latch opening (414) and a ramp (416). Latch member (412) is configured to cooperate with latch protrusion (334) of shaft assembly (330) to selectively secure clamp arm assembly (400) to shaft assembly (330). In particular, when clamp arm assembly (400) is initially provided separately from shaft assembly (330), an operator may align clamp arm assembly (400) with shaft assembly (330) along a common axis, and then insert blade (350) and the remaining distal portion of shaft assembly (330) into clamp arm assembly (400). Ramp (416) will eventually engage latch protrusion (334), which will provide a camming action that causes latch member (412) to deflect away from the longitudinal axis. As the operator continues to insert shaft assembly (330) through clamp arm assembly (400), latch protrusion (334) eventually reaches latch opening (414), at which point latch member (412) resiliently returns to a straight, non-deflected state. At this stage, latch protrusion (334) is disposed in latch opening (414) and thereby secures clamp arm assembly (400) to shaft assembly (330). When the operator wishes to remove clamp arm assembly (400) from shaft assembly (330), the operator may simply engage ramp (416) and thereby urge latch member (412) to a deflected state where latch member (412) can clear latch protrusion (334); then pull clamp arm assembly (400) away from shaft assembly (330). Other suitable structures and techniques that may be used to secure clamp arm assembly (400) to shaft assembly (330), and to remove clamp arm assembly (400) from shaft assembly (330), will be apparent to those of ordinary skill in the art in view of the teachings herein.

Clamp arm body (430) of the present example comprises a clamp pad (432) and a pair of proximal projections (434). Clamp pad (432) is positioned and configured to compress tissue against ultrasonic blade (350) when clamp arm assembly (400) is secured to shaft assembly (330). Shield member (406) of shroud (404) is configured to extend over the exterior of the distal end of clamp arm body (430), without covering clamp pad (432). Shield member (406) thus enables clamp pad (432) to contact tissue directly. Projections (438) each comprise a respective proximally presented recess (436) and a pair of pin openings (438). A pin (440) is positioned in pin openings (411, 438) to thereby pivotally couple clamp arm body (430) with stationary body (410). Shrouds (402, 404) are fixedly secured to clamp arm body (430) such that shrouds (402, 404) pivot with clamp arm body (430) relative to stationary body (410).

Figure 23:
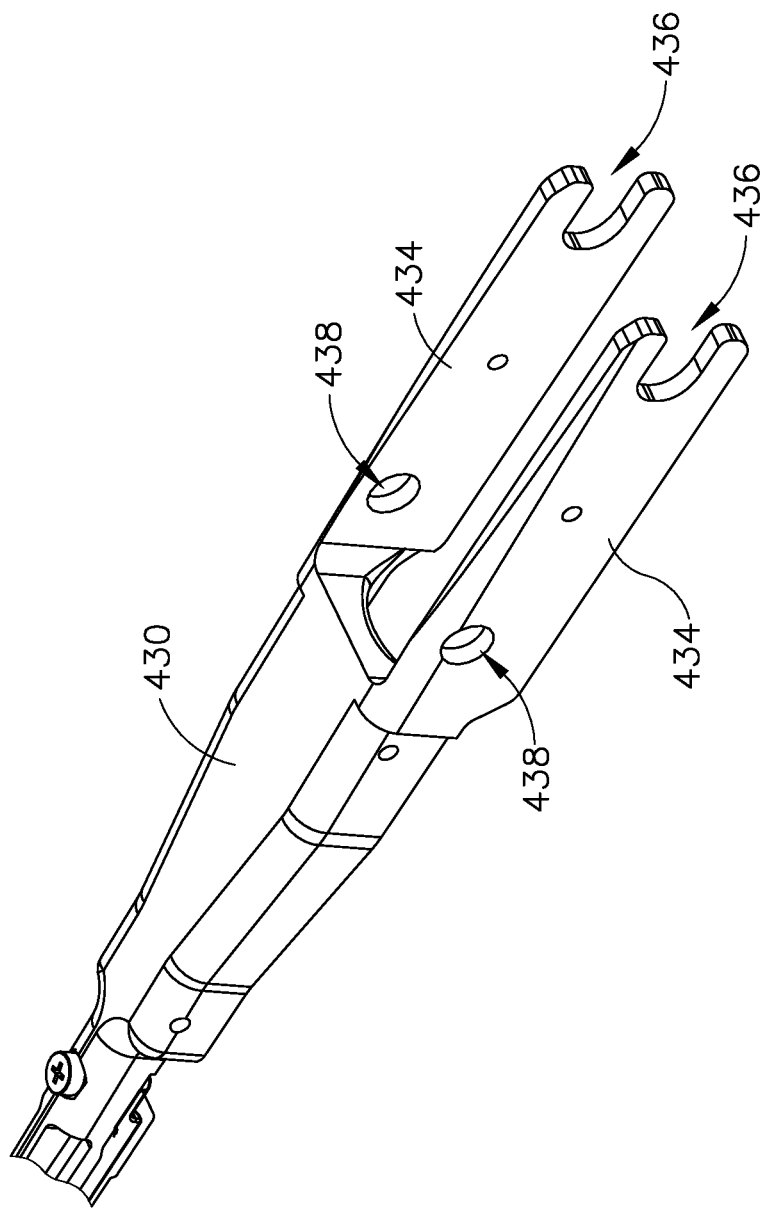
FIG. 23 depicts a partial perspective view of a proximal end of a clamp arm body of the clamp arm assembly of FIG. 22.

As shown in FIG. 23, recesses (436) have a generally U-shaped configuration. Recesses (436) are configured to receive camming protrusions (328) of clamp arm actuator (320). In other words, when shaft assembly (330) is inserted into clamp arm assembly (400) as described above, camming protrusions (328) will enter recesses (436) when latch member (412) reaches the point at which latch member (412) secures clamp arm assembly (400) to shaft assembly (330). When the operator removes clamp arm assembly (400) from shaft assembly (330), camming protrusions (328) may freely exit recesses (436), as clamp arm actuator (320) remains secured to shaft assembly (330). As best seen in FIG. 17, shrouds (402, 404) are configured to cover the interfaces between recesses (436) and camming protrusions (328). It should be understood that the relationship between recesses (436) and camming protrusions (328) is substantially identical to the relationship between camming protrusion (216) and camming recess (226) described above. Thus, recesses (436) and camming protrusions (328) provide a pivoting coupling between clamp arm body (430) and clamp arm actuator (320).

As noted above, clamp arm actuator (320) is pivotally coupled with shaft assembly (330) via pin (338); and clamp arm body (430) is pivotally coupled with stationary body (410) via pin (440); while stationary body (410) is fixedly secured to shaft assembly (330). The pivoting interface between recesses (436) and camming protrusions (328) is longitudinally positioned between the longitudinal positions of pins (338, 440). It should therefore be understood that clamp arm actuator (320) and clamp arm body (430) cooperate to provide a compound lever assembly. When an operator pivots thumb ring (324) toward handle assembly (311), the compound lever action provides corresponding pivotal movement of clamp pad (432) toward ultrasonic blade (350).

In the present example, a resilient beam (313) is secured to clamp arm actuator (320) and slidably bears against shaft assembly (330), such that resilient beam (313) resiliently urges clamp arm actuator (320) away from handle assembly (311). Thus, when an operator relaxes their grip on thumb ring (324), resilient beam (313) will urge thumb ring (324) away from handle assembly (311), thereby urging clamp pad (432) away from ultrasonic blade (350). Of course, any other suitable components and arrangements may be used to provide a resilient bias to clamp arm actuator (320). Alternatively, such resilient bias may simply be omitted.

III. Exemplary Ultrasonic Surgical Instrument with Optimal Gap Setting Mechanism In some instances, it may be beneficial for an ultrasonic surgical instrument to provide the operator with an indication that a predetermined gap has been established between ultrasonic blade (150) and clamp pad (222) of end effector (12) during spot coagulation. Improving the ability of ultrasonic surgical instruments, such as surgical instrument (10, 301) discussed above, to form the predetermined gap at end effector (12) may be desirable when providing ultrasonic and/or RF energy to a patient's tissue, such as performing a spot coagulation on a patient's tissue. Furthermore, it may be desirable for ultrasonic surgical instruments to be able to maintain the predetermined gap between ultrasonic blade (150) and clamp pad (222) for an extended period. Providing this ability may improve an operator's capability to move clamp pad (222) toward ultrasonic blade (150) to an intermediate position with the predetermined gap formed at end effector (12). This may be beneficial to ensure end effector

(12) is not excessively urged to a closed position or unproductively urged towards the intermediate position but remaining in an open position. Providing a surgical instrument that is able to achieve and maintain the predetermined gap at end effector (12) may approve the operator's ability to successfully perform a spot coagulation of a patient's tissue.

In ultrasonic surgical instruments, such as instrument (10, 301) described above, it may be beneficial to include a spacer, whether a physical component or electrical, that is attached or removably inserted onto handle assembly (110), clamp arm assembly (210), and/or shaft assembly (330) to thereby inhibit movement of clamp arm assembly (210) for maintaining the predetermined gap in use and/or provide an indication to the operator that the predetermined gap is formed at end effector (12). It may be desirable to provide the spacer in a manner that allows the operator to freely transition the spacer from an unactuated position, where the spacer is not actively operational to set the predetermined gap at end effector (12), to an actuated position where the spacer is actively operable to form the predetermined gap between ultrasonic blade (150) and clamp pad (222) as the ultrasonic surgical instrument (10, 301) is engaged. This may provide the operator with the selective ability to activate the spacer when the predetermined gap in end effector (12) is desired. It may further be desirable for the spacer to inhibit ultrasonic blade (150) and clamp pad (222) from the closed position. The following description provides various examples of an ultrasonic surgical instrument (5100, 5200, 5300, 5400, 5500, 5600, 5700, 5800, 5900, 6000, 6100, 6200, 6300, 6400, 6500, 6600, 6700, 6800, 6900) and corresponding end effectors (5140, 5240, 5340, 5440, 5540, 5640, 5740, 5840, 5940, 6040, 6140, 6240, 6340, 6440, 6540, 6640, 6740, 6840, 6940) that are cooperatively configured to provide a predetermined gap at end effector (5140, 5240, 5340, 5440, 5540, 5640, 5740, 5840, 5940, 6040, 6140, 6240, 6340, 6440, 6540, 6640, 6740, 6840, 6940).

It should be understood that spacers (5150, 5250, 5350, 5450, 5550, 5650, 5750, 5850, 5950, 6050, 6150, 6250) and urging mechanisms (6350, 6450, 6550, 6650, 6750, 6850, 6950) described below may be readily incorporated into in any of the various surgical instruments (10, 301) described above and in any of the various surgical procedures described in the various references described herein. Other suitable ways in which the below-described surgical instruments (5100, 5200, 5300, 5400, 5500, 5600, 5700, 5800, 5900, 6000, 6100, 6200, 6300, 6400, 6500, 6600, 6700, 6800, 6900), spacers (5150, 5250, 5350, 5450, 5550, 5650, 5750, 5850, 5950, 6050, 6150, 6250) and urging mechanisms (6350, 6450, 6550, 6650, 6750, 6850, 6950) may be used will be apparent to those of ordinary skill in the art in view of the teachings herein. It should be understood that handle body (5110, 5210, 5310, 5410, 5510, 5610, 5710, 5810, 5910, 6010, 6110, 6210, 6310, 6410, 6510, 6610, 6710, 6810, 6910), shaft assembly (5120, 5220, 5320, 5420, 5520, 5620, 5720, 5820, 5920, 6020, 6120, 6220, 6320, 6420, 6520, 6620, 6720, 6820, 6920) and clamp arm actuator (5130, 5230, 5330, 5430, 5530, 5630, 5730, 5830, 5930, 6030, 6130, 6230, 6330, 6430, 6530, 6630, 6730, 6830, 6930) may be configured and operable in accordance with those assemblies in surgical instruments (10, 301) described above except for the differences explicitly noted herein. Like reference numerals below are directed to like features described above.

Figure 24A:
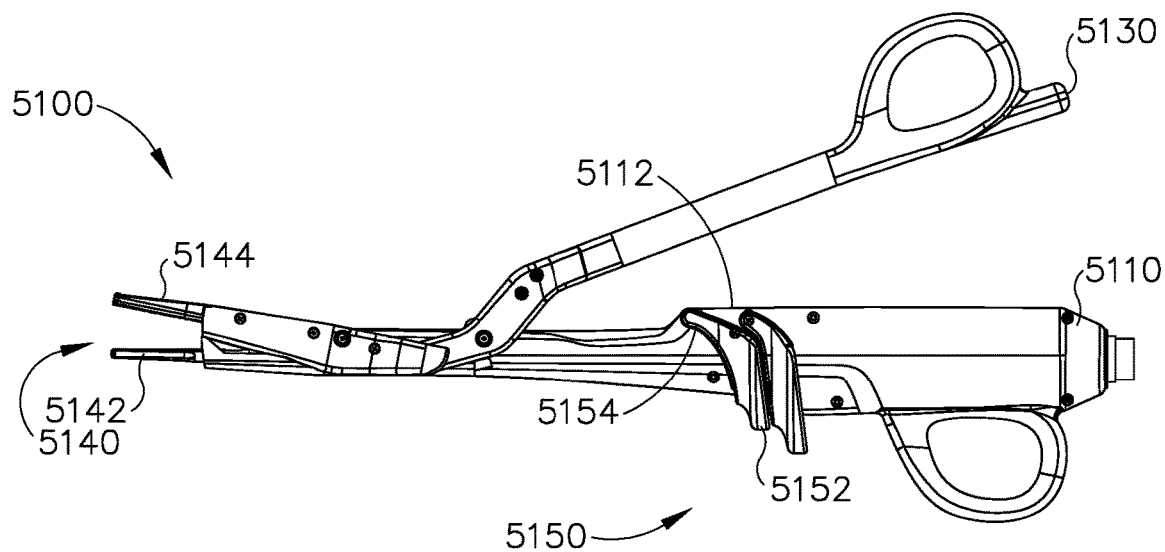
FIG. 24A depicts a side elevational view of a third exemplary surgical instrument including an exemplary toggle spacer and an end effector, with the toggle spacer in an unactuated position and the end effector in an open position.
Figure 24B:
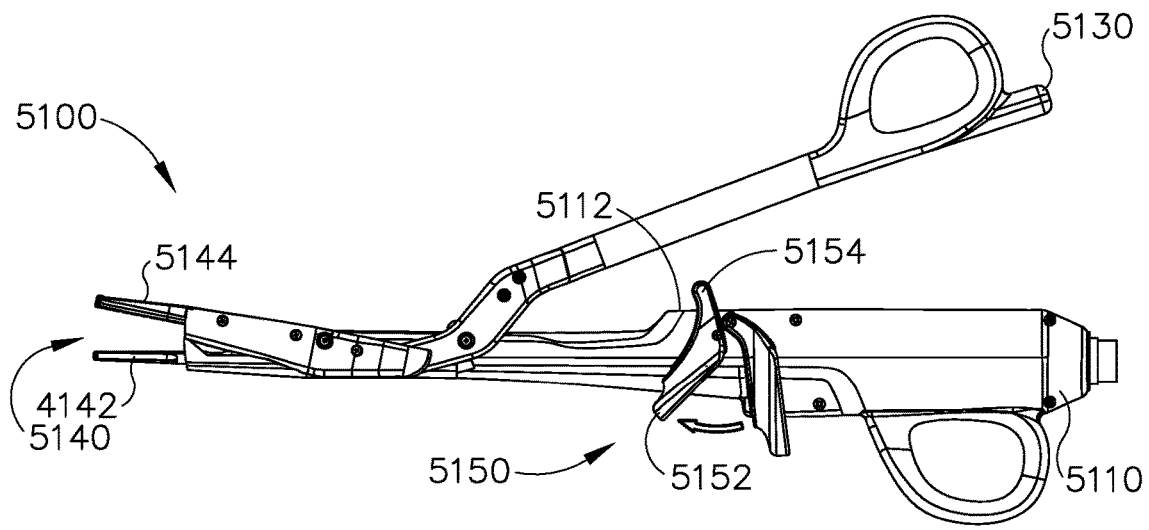
FIG. 24B depicts a side elevational view of the surgical instrument of FIG. 24A, with the toggle spacer in an actuated position and a blocker extending towards a clamp arm actuator.
Figure 24C:
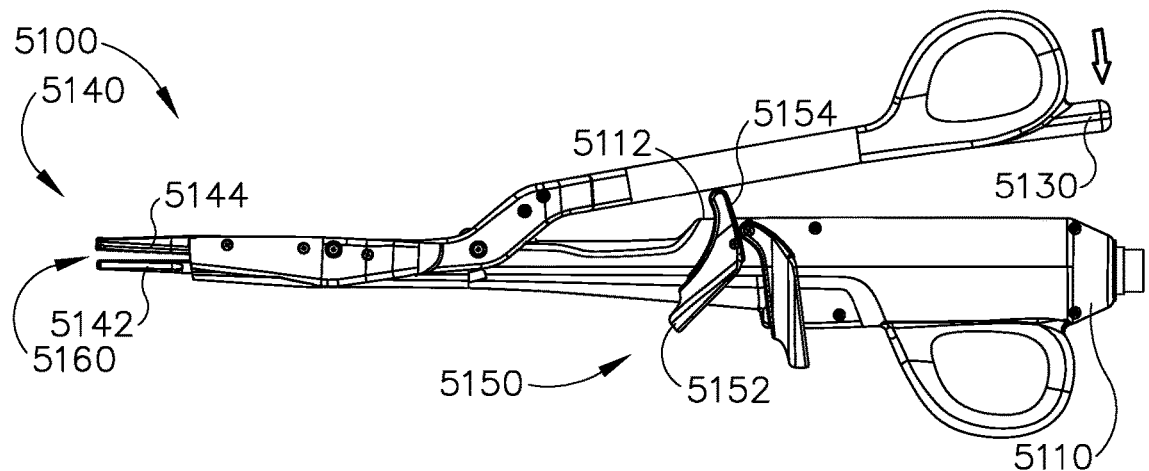
FIG. 24C depicts a side elevational view of the surgical instrument of FIG. 24A, with the toggle spacer in the actuated position and the end effector in an intermediate position.

A. Exemplary Surgical Instrument with Spacer Mechanism i. Toggle Spacer with Switch Adjuster FIGS. 24A-24D show an exemplary toggle spacer (5150) positioned along a handle body (5110) of a third exemplary surgical instrument (5100). Toggle spacer (5150) includes a switch adjuster (5152) and a blocker (5154). Toggle spacer (5150) is configured to move from an unactuated position, as seen in FIG. 24A, to an actuated position shown in FIG. 24B. With toggle spacer (5150) in the unactuated position, an end effector (5140) of surgical instrument (5100) is configured to close an ultrasonic blade (5142) and a clamp arm (5144) without interruption from toggle spacer (5150). However, with toggle spacer (5150) in the actuated position, blocker (5154) is extended transversely upwards from handle body (5110) and towards a clamp arm actuator (5130) of surgical instrument (5100), as seen in FIG. 24B. In this instance, blocker (5154) is configured to inhibit clamp arm actuator (5130) moving toward handle body (5110) to the closed configuration.

In the present example, as seen in FIG. 24A-24B, switch adjuster (5152) is a switch configured to be moved distally to thereby pivot blocker (5154) from a first position, below an upper surface (5112) of handle body (5110), to a second position extending towards clamp arm actuator (5130) above upper surface (5112). Although not shown, it will be apparent to those of ordinary skill in the art that switch adjuster (5152) may be a button or other user interface feature. With toggle spacer (5150) in the actuated position, blocker (5154) is configured to inhibit clamp arm actuator (5130) from moving towards handle body (5110) to the closed configuration. In this instance, blocker (5154) is a protrusion configured to extend from upper surface (5112) of handle body (5110) at a transverse length that corresponds to a predetermined gap (5160) between ultrasonic blade (5142) and clamp arm (5144) of end effector (5140). With toggle spacer (5150) in the actuated position, blocker (5154) is configured to maintain end effector (5140) at an intermediate position with predetermined gap (5160) formed between ultrasonic blade (5142) and clamp arm (5144).

Figure 24D:
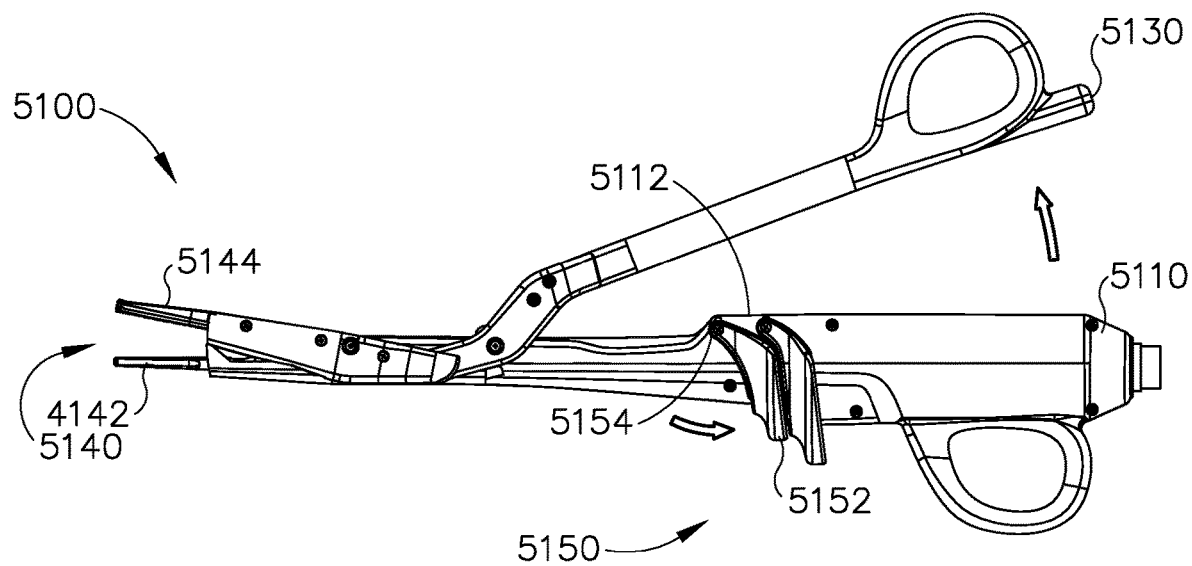
FIG. 24D depicts a side elevational view of the surgical instrument of FIG. 24A with the toggle spacer in the unactuated position and the end effector in the open position.

Switch adjuster (5152) is further configured to be moved proximally to thereby pivot blocker (5154) from the second position to the first position. FIG. 24D shows clamp arm actuator (5130) moved away from handle body (5110) to the open configuration and toggle spacer (5150) in the unactuated position. As toggle spacer (5150) is transitioned from the actuated position to the unactuated position, blocker (5154) is configured to reversibly pivot to the first position with blocker (5154) below upper surface (5112) of handle body (5110). With toggle spacer (5150) in the unactuated position, clamp arm actuator (5130) is configured to move relative to handle body (5150) to the closed configuration without encountering blocker (5154) to thereby move ultrasonic blade (5142) and clamp arm (5144) to the closed position.

ii. Slidable Spacer with Steering Adjuster

Figure 25A:
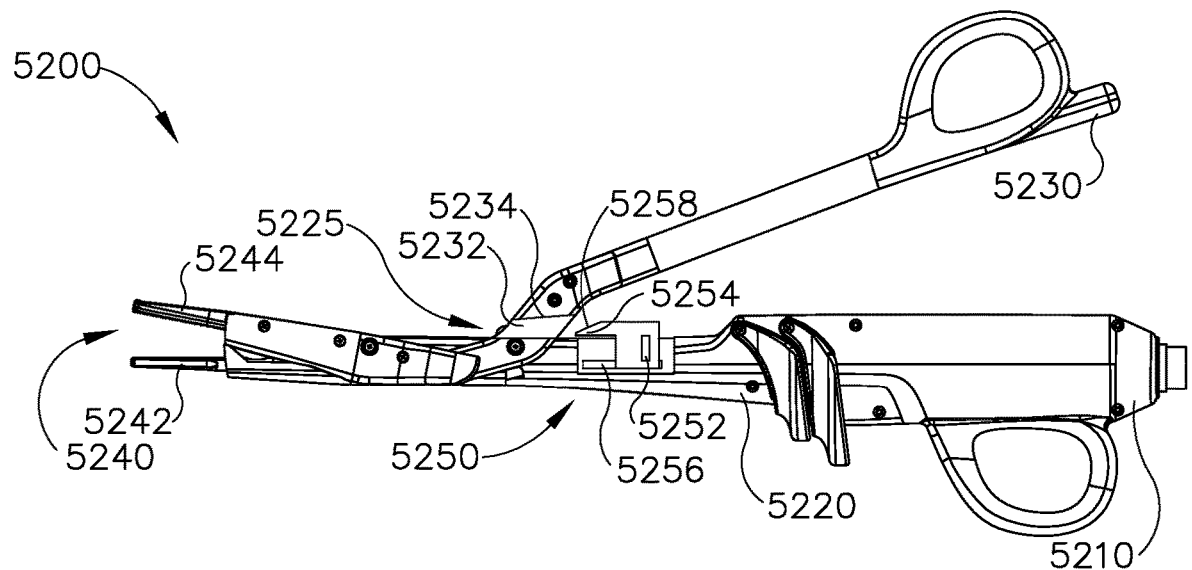
FIG. 25A depicts a side elevational view of a fourth exemplary surgical instrument including an exemplary slidable spacer and an end effector, with the slidable spacer in an unactuated position and the end effector in an open position.
Figure 25B:
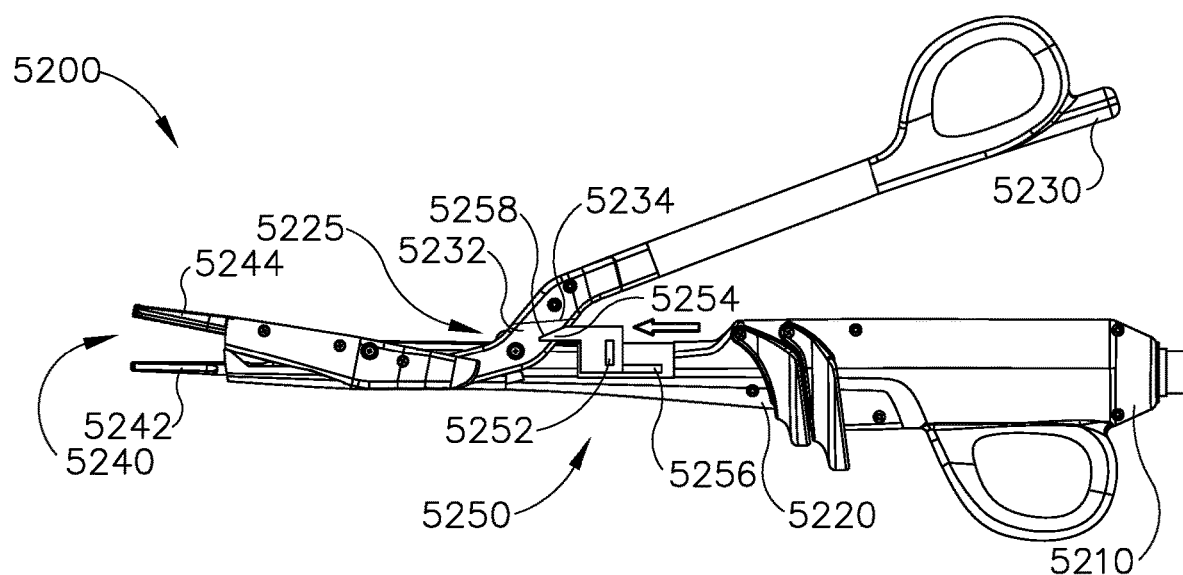
FIG. 25B depicts a side elevational view of the surgical instrument of FIG. 25A, with the slidable spacer in an actuated position and a blocker extending distally towards a clamp arm actuator.

FIGS. 25A-25D show an exemplary slidable spacer (5250) positioned along a shaft assembly (5220) of a fourth exemplary surgical instrument (5200). Slidable spacer (5250) includes a steering adjuster (5252) and a blocker (5254) on a proximal end of slidable spacer (5250). Slidable spacer (5250) is configured to be selectively manipulated from an unactuated position, proximal to a handle body (5210) as seen in FIG. 25A, to an actuated position, distal to handle body (5210) and proximal to clamp arm actuator (5230), as seen in FIG. 25B. With slidable spacer (5250) in the unactuated position, an end effector (5240) of surgical instrument (5200) is configured to close an ultrasonic blade (5242) and a clamp arm (5244) without interruption from slidable spacer (5250). However, with slidable spacer (5250) in the actuated position, blocker (5254) is distally advanced along a shaft assembly (5220) towards clamp arm actuator (5230), as seen in FIG. 25B. Clamp arm actuator (5230) includes a slot (5232) in longitudinal alignment with blocker (5254) such that slot (5232) is configured to receive blocker (5254). Steering adjuster (5252) is configured to slidably translate blocker (5254) distally towards slot (5232). In this instance, blocker (5254) is configured to inhibit clamp arm actuator (5230) moving toward handle body (5210) to the closed configuration when positioned within slot (5232).

In the present example, as seen in FIGS. 25A-25B, steering adjuster (5252) is along both sides of slidable spacer (5250) and is configured to slide blocker (5254) distally along a longitudinal track (5256) on shaft assembly (5220). Actuating steering adjuster (5250) advances blocker (5254) along longitudinal track (5256) from a first position, located on a proximal end of shaft assembly (5220), to a second position, extending into slot (5232). With slidable spacer (5250) in the actuated position, as seen in FIG. 25B, blocker (5254) is configured to inhibit clamp arm actuator (5230) from moving toward handle body (5210) to the closed configuration. In this instance, blocker (5254) is configured to slidably translate along shaft assembly (5220) and be received within slot (5232). Slot (5232) is positioned on clamp arm actuator (5230) adjacent to a coupling portion (5225). In the present example, blocker (5254) includes a tapered head (5258) configured to associate with an inner surface (5234) of slot (5232) with blocker (5254) wedged into slot (5232). In other words, with slidable spacer (5250) in the actuated position, bottom surface (5234) is configured to fittingly engage tapered head (5258).

With slidable spacer (5250 in the actuated position, blocker (5254) is configured to prevent the downward movement of inner surface (5234) relative to shaft assembly (5220). In this instance, blocker (5250) is configured to inhibit clamp arm actuator (5230) from moving relative to handle body (5210) to the closed configuration. The height of tapered head (5258) is configured to correspond with a predetermined gap (5260) formed between ultrasonic blade (5242) and clamp arm (5244) of end effector (5240). With slidable spacer (5250) in the actuated position, blocker (5254) is configured to maintain end effector (5240) at an intermediate position with predetermined gap (5260) formed between ultrasonic blade (5242) and clamp arm (5244).

Steering adjuster (5252) is further configured to slide blocker (5254) proximally along longitudinal track (5256) on shaft assembly (5220). FIG. 25D illustrates clamp arm actuator (5230) moved away from handle body (5210) to the open configuration and slidable spacer (5250) in the unactuated position. As slidable spacer (5250) transitions from the actuated position to the unactuated position, blocker (5254) is configured to slidably translate to the first position with blocker (5254) proximal to slot (5232) and tapered head (5258) disengaged from inner surface (5234). With slidable spacer (5250) in the unactuated position, clamp arm actuator (5230) is configured to move toward handle body (5210) to the closed configuration without encountering blocker (5254) to thereby move ultrasonic blade (5242) and clamp arm (5244) to the closed position. As seen in FIG. 26, slidable spacer (5250) further includes a cavity (5251) and a pair of latches (5253). Cavity (5251) is between adjusters (5252) and beneath blocker (5254). Cavity (5251) is configured to receive and attach to shaft assembly (5220). Latches (5253) are along a bottom end of slidable spacer (5250) and are sized to be received within longitudinal track (5256). Latches (5253) are configured to allow steering adjuster (5252) to slidably translate blocker (5254) along longitudinal track (256).

iii. Slidable Spacer with Curved Blocker

Figure 27A:
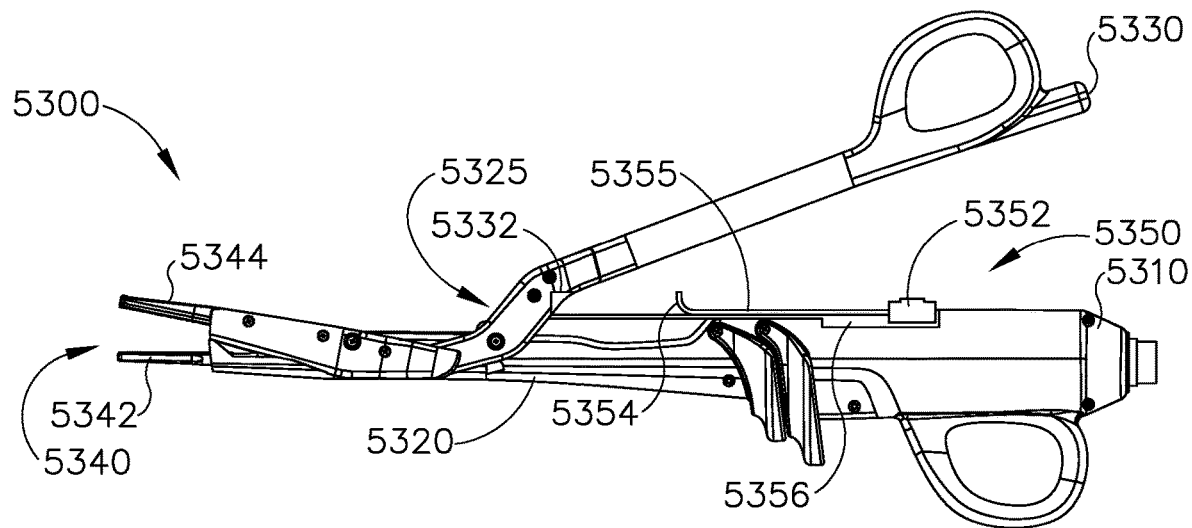
FIG. 27A depicts a side elevational view of a fifth exemplary surgical instrument including an exemplary alternative slidable spacer and an end effector, with the slidable spacer in an unactuated position and the end effector in an open position.
Figure 27B:
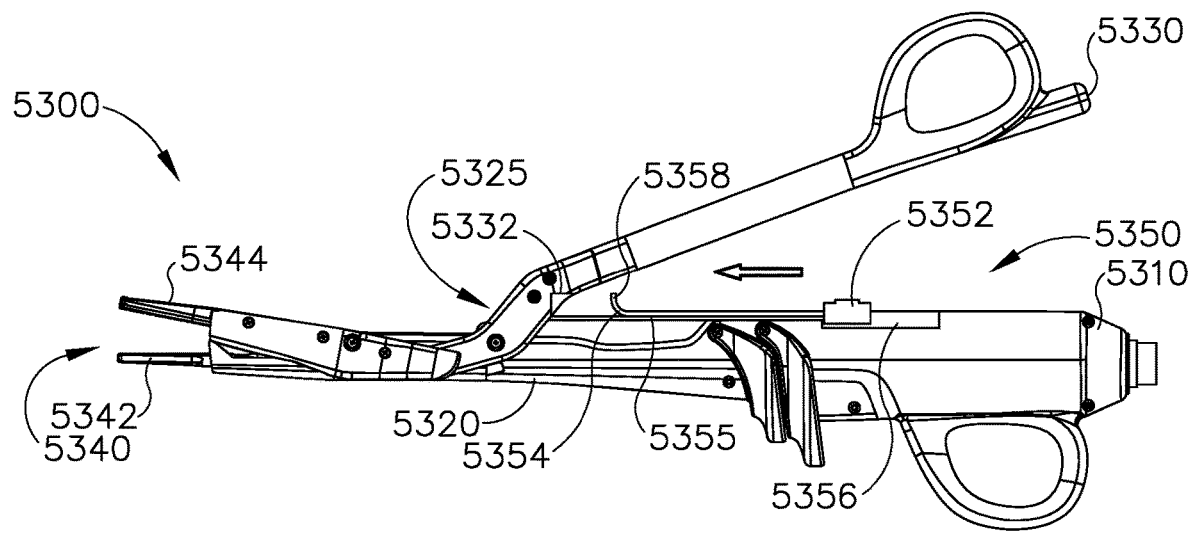
FIG. 27B depicts a side elevational view of the surgical instrument of FIG. 27A, with the slidable spacer in an actuated position and a blocker extending distally towards a clamp arm actuator.

FIGS. 27A-27D show an exemplary slidable spacer (5350) positioned along a handle body (5310) and distally extending onto a shaft assembly (5320) of a fifth exemplary surgical instrument (5300). Slidable spacer (5350) includes a guiding adjuster (5352) on a distal end of slidable spacer (5350) and a curved blocker (5354) on a proximal end of slidable spacer (5350). Slidable spacer (5350) further includes an extension (5355) positioned between guiding adjuster (5352) and curved blocker (5354). Slidable spacer (5350) is configured to move from an unactuated position, as seen in FIG. 27A, to an actuated position, as shown in FIG. 27B. With slidable spacer (5350) in the unactuated position, an end effector (5340) of surgical instrument (5300) is configured to close an ultrasonic blade (5342) and a clamp arm (5344) without interruption from curved blocker (5354). However, with slidable spacer (5350) in the actuated position, curved blocker (5354) is distally advanced along shaft assembly (5320) by extension (5355) towards a coupling portion (5325), as seen in FIG. 129B. Clamp arm actuator (5330) includes a blocked surface (5332) configured to engage curved blocker (5354) with slidable spacer (5350) in the actuated position. In this instance, with extension (5335) extending curved blocker (5354) underneath blocked surface (5332), curved blocker (5354) is configured to inhibit clamp arm actuator (5330) from moving relative to handle body (5310) to the closed configuration.

In the present example, guiding adjuster (5352) is a guider at a distal end of slidable spacer (5350) and is configured to translate curved blocker (5354) distally along a longitudinal track (5356) on handle body (5310) when manually manipulated. In other words, guiding adjuster (5352) is configured to translate curved blocker (5354) along longitudinal track (5356) from a first position, as shown in FIG. 27A, to a second position with curved blocker (5354) directly beneath blocked surface (5332), as seen in FIG. 27B. With slidable spacer (5350) in the actuated position, curved blocker (5354) is configured to inhibit clamp arm actuator (5330) moving towards handle body (5310) to the closed configuration. In this instance, curved blocker (5354) includes a curved arm (5358) configured to extend toward clamp arm actuator (5330) and wedge against blocked surface (5332), as seen in FIG. 27C. The profile of curved arm (5358) is configured to impede the downward movement of blocked surface (5332) relative to shaft assembly (5320). With slidable spacer (5350) in the actuated position, curved blocker (5354) is configured to maintain end effector (5340) at an intermediate position with predetermined gap (5360) formed between ultrasonic blade (5342) and clamp arm (5344). The profile of curved arm (5358) is configured to correspond with a predetermined gap (5360) formed between ultrasonic blade (5342) and clamp arm (5344).

Guiding adjuster (5352) is further configured to translate curved blocker (5354) proximally along longitudinal track (5356). As seen in FIG. 27D, clamp arm actuator (5330) is moved away from handle body (5310) in the open configuration with slidable spacer (5350) in the unactuated position. As slidable spacer (5350) is transitioned from the actuated position to the unactuated position, curved blocker (5354) is configured to proximally translate to the first position with curved arm (5358) disengaged from blocked surface (5332). With slidable spacer (5350) in the unactuated position, clamp arm actuator (5330) is configured to move toward handle body (5310) to the closed configuration without encountering curved blocker (5354) to thereby allow ultrasonic blade (5342) to move toward clamp arm (5344) to the closed position. As seen in FIG. 28, slidable spacer (5350) further includes a pair of latches (5353) connected along a bottom end of slidable spacer (5350). Latches (5353) are sized to be received within longitudinal track (5356) and configured to allow guiding adjuster (5352) to slidably translate blocker (5354) along longitudinal track (5356).

Figure 29A:
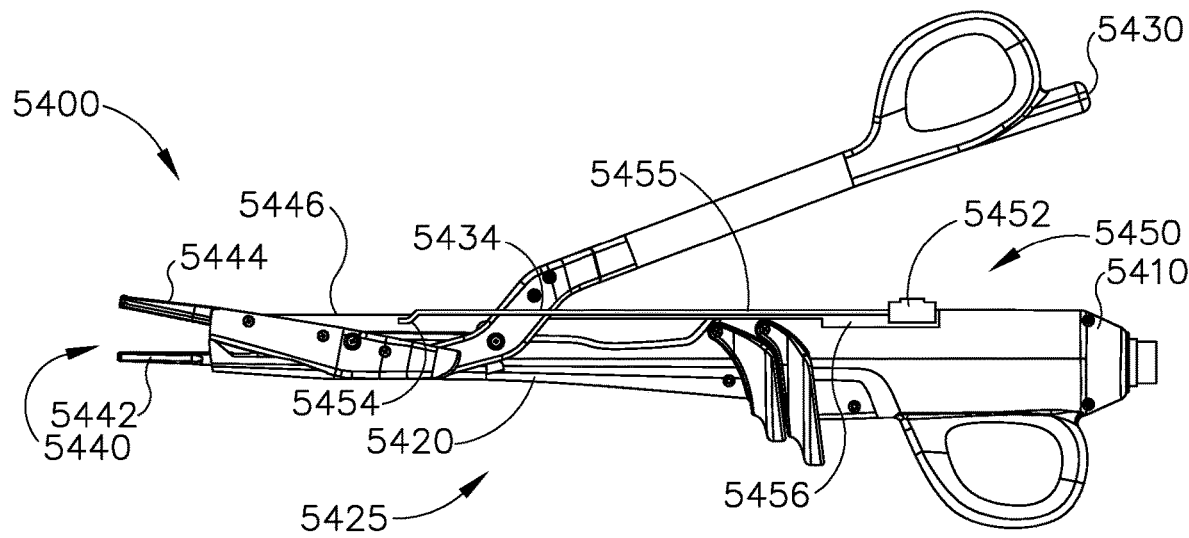
FIG. 29A depicts a side elevational view of a sixth exemplary surgical instrument including another exemplary alternative slidable spacer and an end effector, with the slidable spacer in an unactuated position and the end effector in an open position.
Figure 29B:
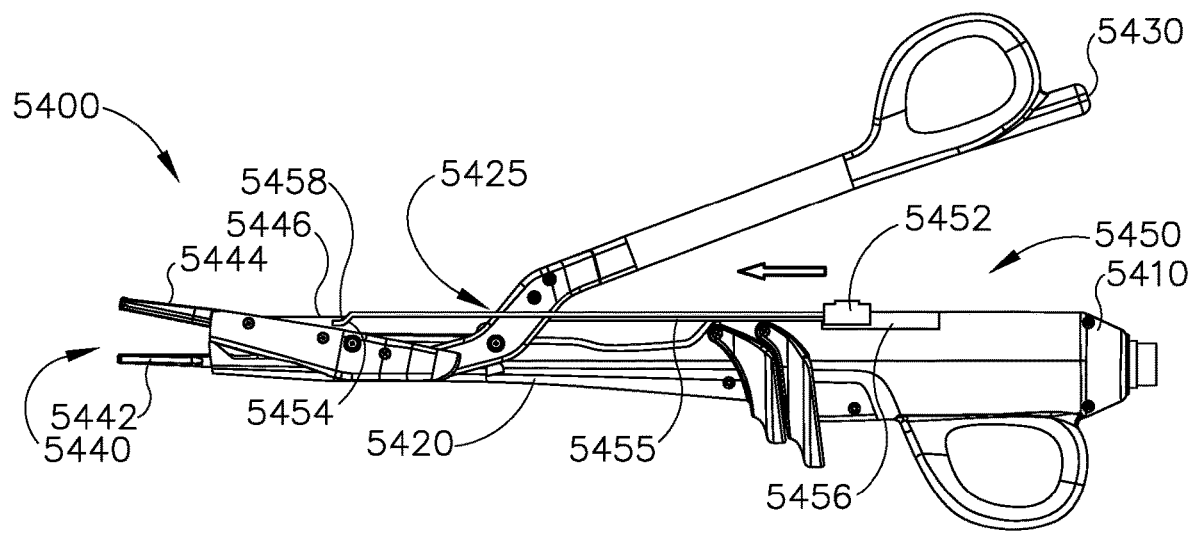
FIG. 29B depicts a side elevational view of the surgical instrument of FIG. 29A, with the slidable spacer in an actuated position and a blocker extending distally towards a clamp arm actuator.

FIGS. 29A-29B illustrate an exemplary alternative slidable spacer (5450) similar in configuration and operability to slidable spacer (5350). In the present example, slidable spacer (5450) includes a guiding adjuster (5452) and a curved blocker (5454). Slidable spacer (5450) further includes an extension (5455) positioned between guiding adjuster (5452) and curved blocker (5454). Slidable spacer (5450) is configured to move from an unactuated position to an actuated position, as seen in FIGS. 29A-29B, respectively. With slidable spacer (5450) in the unactuated position, an end effector (5440) of a sixth exemplary surgical instrument (5400) is configured to close an ultrasonic blade (5442) and a clamp arm (5444) without interruption from curved blocker (5454). Curved blocker (5454) includes a curved arm (5458). As seen in FIGS. 29A, clamp arm actuator (5430) includes a channel (5434), adjacent to a coupling portion (5425), configured to slidably receive extension (5455) to thereby position curved blocker (5454) within clamp arm (5444). With slidable spacer (5450) in the actuated position, curved blocker (5454) is distally advanced within clamp arm (5444) by extension (5455), as seen in FIG. 29B. Clamp arm (5445) includes a blocked surface (5446) configured to engage curved blocker (5454) with slidable spacer (5450) in the actuated position. In this instance, with extension (5455) extending curved blocker (5454) underneath blocked surface (5446), curved blocker (5454) is configured to inhibit clamp arm actuator (5430) from moving relative to handle body (5410) to the closed configuration.

Figure 29C:
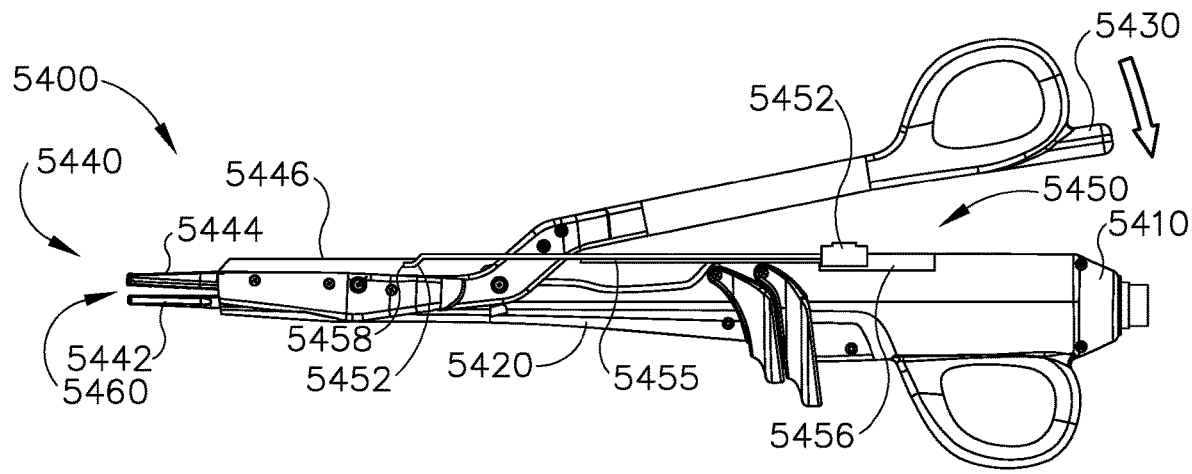
FIG. 29C depicts a side elevational view of the surgical instrument of FIG. 29A, with the slidable spacer in the actuated position and the end effector in an intermediate position.

As seen in FIG. 29C, guiding adjuster (5452) is configured to translate curved blocker (5454) distally along a longitudinal track (5456) from a first position, as shown in FIG. 29A, to a second position with curved blocker (5454) beneath blocked surface (5446). With slidable spacer (5450) in the actuated position, curved blocker (5454) is configured to inhibit clamp arm actuator (5430) moving toward handle body (5410) to the closed configuration due to curved arm (5458) being wedged against block surface (5446). Similar to curved arm (5358), the transverse length of curved arm (5458) is configured to impede the downward movement of blocked surface (5446) relative to ultrasonic blade (5442). With slidable spacer (5450) in the actuated position, curved blocker (5454) is configured to maintain end effector (5440) at an intermediate position with predetermined gap (5560) formed between ultrasonic blade (5442) and clamp arm (5444). The transverse length of curved arm (5458) is configured to correspond with a predetermined gap (5460) formed between ultrasonic blade (5442) and clamp arm (5444).

Figure 29D:
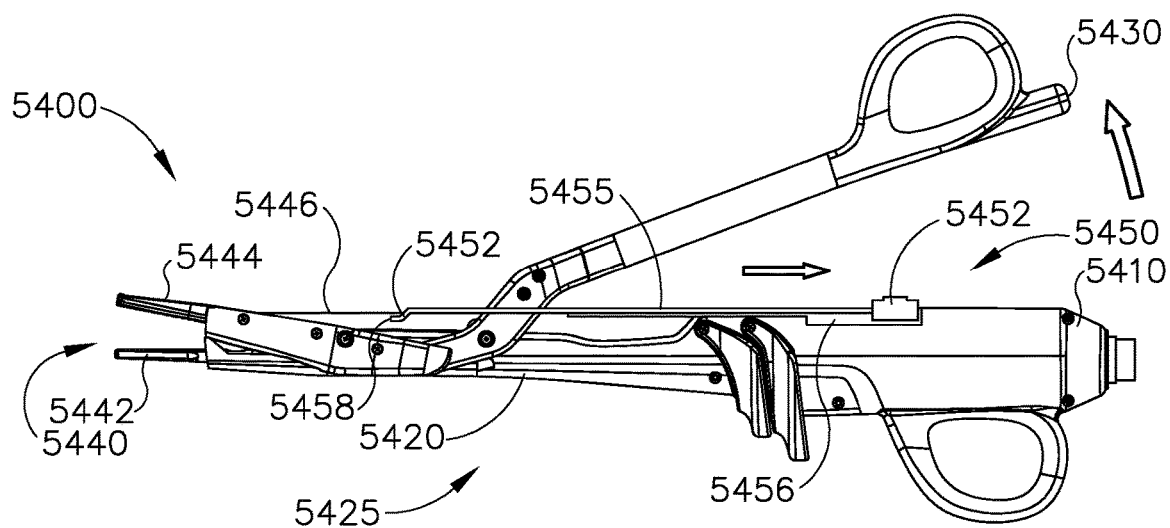
FIG. 29D depicts a side elevational view of the surgical instrument of FIG. 29A, with the slidable spacer returned to the unactuated position and the blocker extending proximal to a clamp arm actuator, with the end effector extended back to the open position.

Guiding adjuster (5452) is further configured to translate curved blocker (5454) proximally along longitudinal track (5456). FIG. 29D shows clamp arm actuator (5430) separated from handle body (5410) in the open configuration with slidable spacer (5450) in the unactuated position. As slidable spacer (5450) is transitioned from the actuated to the unactuated position, curved blocker (5450) is configured to proximally translate to the first position with curved arm (5458) disengaged from blocked surface (5446). With slidable spacer (5450) in the unactuated position, clamp arm actuator (5430) is configured to move toward handle body (5410) to the closed configuration without encountering curved blocker (5454) to thereby allow ultrasonic blade (5442) to move toward clamp arm (5444) to the closed position.

iv. Biasing Spacer with Toggle Adjuster

Figure 30A:
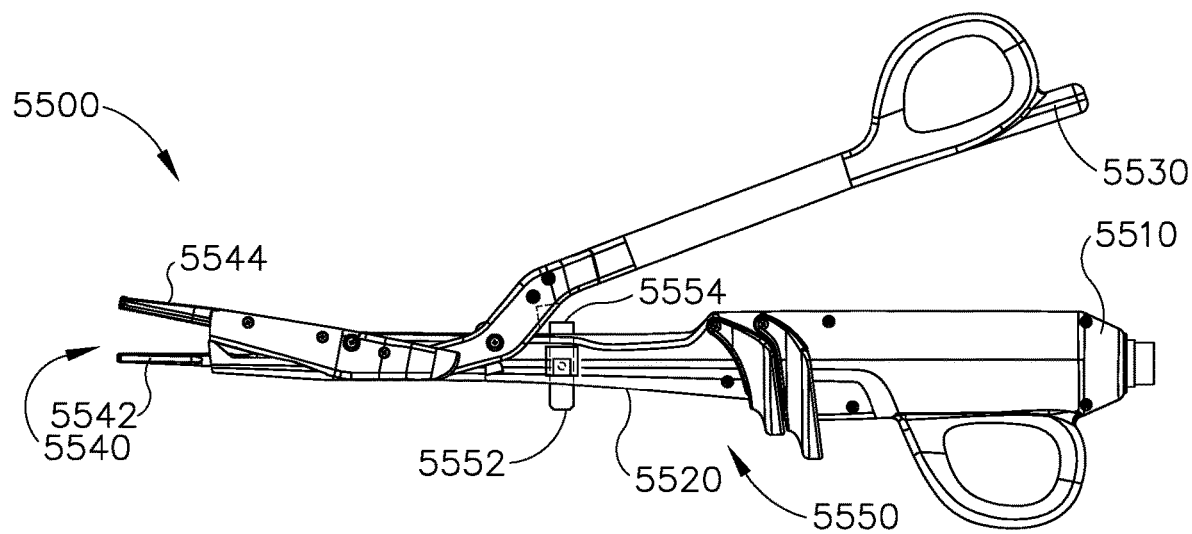
FIG. 30A depicts a side elevational view of a seventh exemplary surgical instrument including exemplary alternative toggle spacer and an end effector, with the toggle spacer in an unactuated position and the end effector in an open position.
Figure 30B:
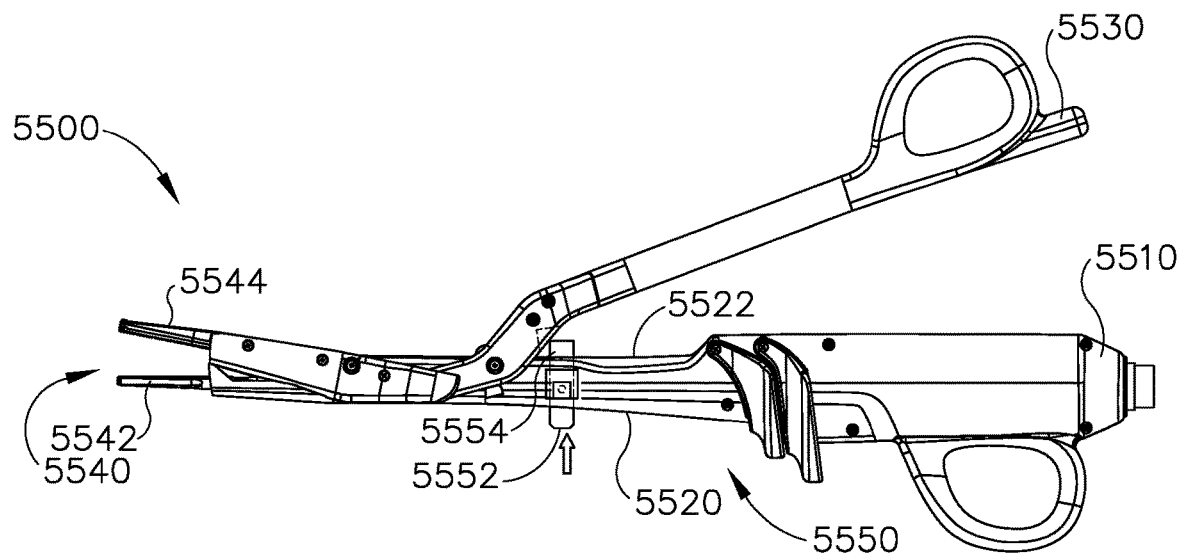
FIG. 30B depicts a side elevational view of the surgical instrument of FIG. 30A, with the toggle spacer in an actuated position and a blocker extending towards a clamp arm actuator.

FIG. 30A shows an exemplary biasing spacer (5550) positioned along a shaft assembly (5520) of a seventh exemplary surgical instrument (5500). Biasing spacer (5550) includes a toggle adjuster (5552) and a blocker (5554). Biasing spacer (5550) is configured to move from an unactuated position, as seen in FIG. 30A, to an actuated position, as shown in FIG. 30B. With biasing spacer (5550) in the unactuated position, an end effector (5540) of surgical instrument (5500) is configured to close an ultrasonic blade (5542) and a clamp arm (5544) to the closed position without interruption from biasing spacer (5550). However, with biasing spacer (5550) in the actuated position, blocker (5554) extends transversely from shaft assembly (5520) towards a clamp arm actuator (5530), as seen in FIG. 30B. In this instance, blocker (5554) is configured to inhibit clamp arm actuator (5530) from moving relative to handle body (5510) to the closed configuration.

In the present example, toggle adjuster (5552) is a button configured to be clicked transversely into shaft assembly (5520) to thereby extend blocker (5554) from a first position, substantially level with an upper surface (5522) of shaft assembly (5520), to a second position extending towards clamp arm actuator (5530). As seen in FIG. 30B, with biasing spacer (5550) in the actuated position, blocker (5554) is a protrusion configured to extend from upper surface (5522) at a transverse length that corresponds to a predetermined gap (5560) formed between ultrasonic blade (5542) and clamp arm (5544). In this instance, blocker (5554) is configured to bias against clamp arm actuator (5530) until toggle adjuster (5552) is clicked transversely into shaft assembly (5520) to thereby retract blocker (5554) to the first position. Biasing spacer (5550) may include a cam, plunger, stop member, spring mechanism, or other biasing mechanism to provide for the retractable extension of blocker (5554) as will be apparent to those of ordinary skill in the art in view of the teachings herein.

Figure 30C:
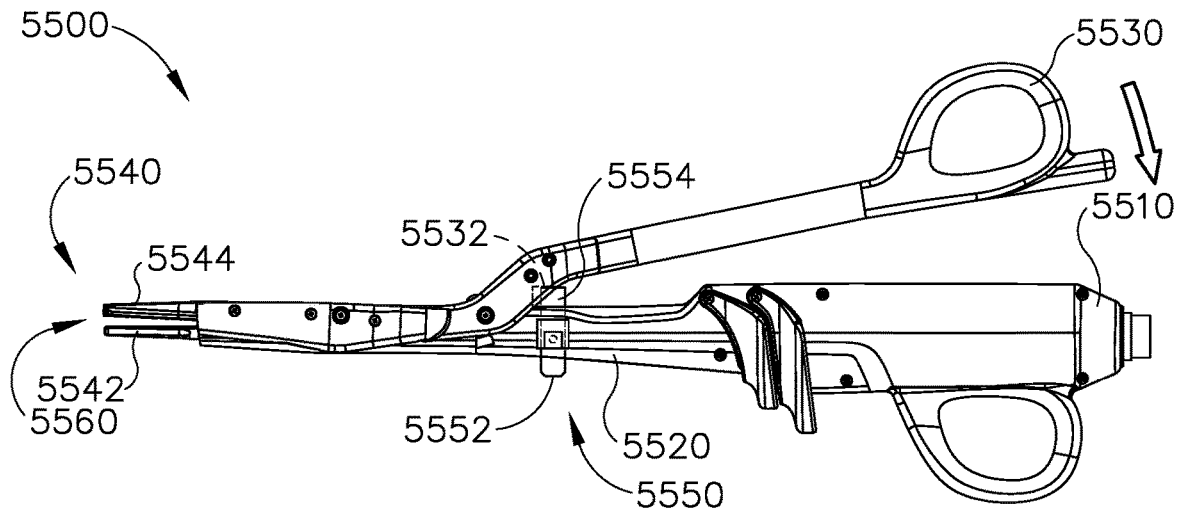
FIG. 30C depicts a side elevational view of the surgical instrument of FIG. 30A, with the toggle spacer in the actuated position and the end effector in an intermediate position.
Figure 30D:
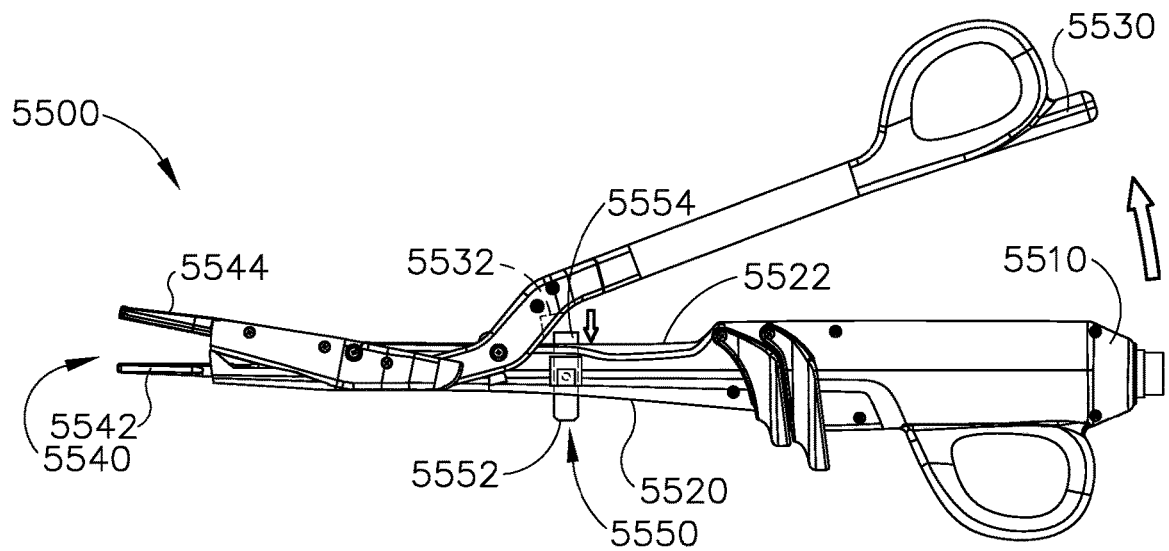
FIG. 30D depicts a side elevational view of the surgical instrument of FIG. 30A, with the toggle spacer returned to the unactuated position and the end effector returned to the open position.

As best seen in FIG. 30C, with biasing spacer (5550) in the actuated position, blocker (5554) is wedged against a blocked surface (5532) of clamp arm actuator (5530). Blocker (5554) is configured to impede the downward movement of blocked surface (5532) to thereby inhibit clamp arm actuator (5530) moving towards handle body (5510) to the closed configuration. Biasing spacer (5550) is configured to be transitioned to the actuated position by clicking toggle adjuster (5552) in the transverse direction relative to shaft assembly (5520). FIG. 30D shows clamp arm actuator (5530) moved away from handle body (5510) with biasing spacer (5550) in the unactuated position. Toggle adjuster (5552) is clicked in the same transverse direction, relative to shaft assembly (5520), to transition biasing spacer (5550) to the unactuated position. As biasing spacer (5550) is transitioned from the actuated position to the unactuated position, blocker (5554) is transversely retracted back to the first position with blocker (5554) substantially level with upper surface (5522) of shaft assembly (5520). With biasing spacer (5550) in the unactuated position, clamp arm actuator (5530) is configured to move towards handle body (5510) to the closed configuration without encountering blocker (5554) to thereby move ultrasonic blade (5542) and clamp arm (5544) to the closed position. Although not shown, it will be apparent to those of ordinary skill in the art that biasing spacer (5550) may alternatively be positioned along handle body (5510) or clamp arm actuator (5530).

v. Gap Spacer with Switch Adjuster

Figure 31A:
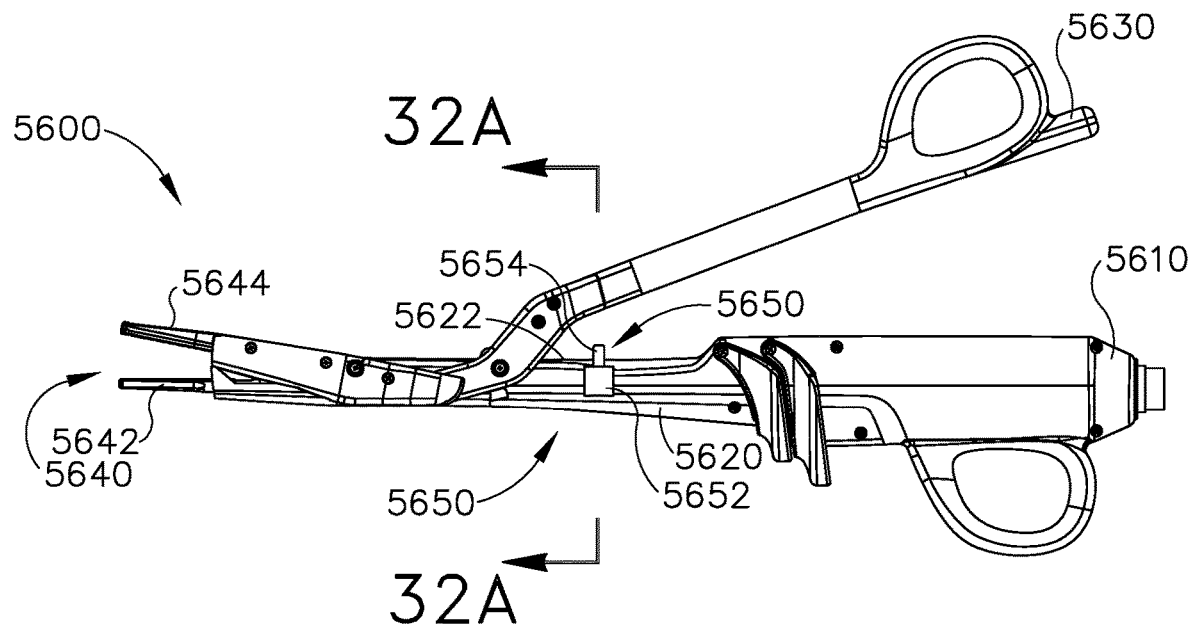
FIG. 31A depicts a side elevational view of an eighth exemplary surgical instrument including an exemplary gap spacer and an end effector, with the gap spacer in an unactuated position and the end effector in an open position.
Figure 31B:
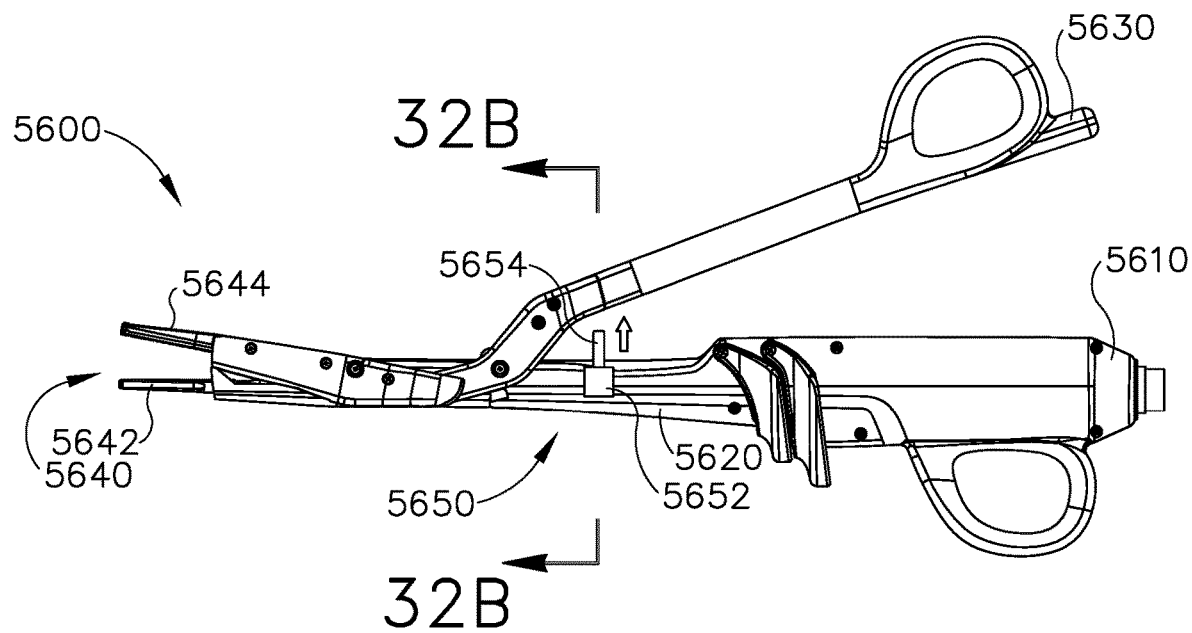
FIG. 31B depicts a side elevational view of the surgical instrument of FIG. 31A, with the gap spacer in an actuated position and a blocker extending towards a clamp arm actuator.

FIG. 31A shows an exemplary gap spacer (5650) positioned along a shaft assembly (5620) of an eighth exemplary surgical instrument (5600). Gap spacer (5650) includes a switch adjuster (5652) and a blocker (5654). Gap spacer (5650) is configured to move from an unactuated position, as seen in FIG. 31A, to an actuated position as shown in FIG. 31B. With gap spacer (5650) in the unactuated position, an end effector (5640) of surgical instrument (5600) is configured to close an ultrasonic blade (5642) and a clamp arm (5644) without interruption from gap spacer (5650). As seen in FIG. 31B, with gap spacer (5650) in the actuated position, blocker (5654) extends transversely from shaft assembly (5620) towards a clamp arm actuator (5630). In this instance, blocker (5654) is configured to inhibit clamp arm actuator (5630) moving towards handle body (5610) to a closed configuration by blocking the downward movement of clamp arm actuator (5630) relative to handle body (5610).

Figure 32A:
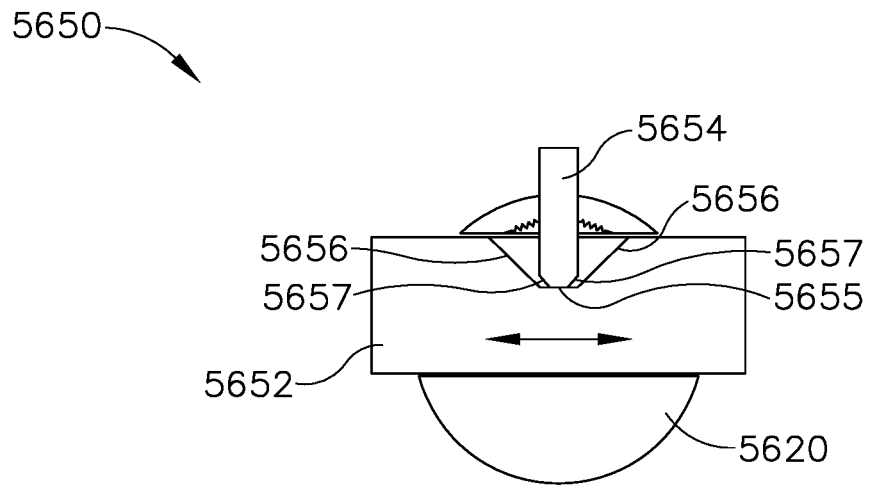
FIG. 32A depicts a cross-sectional view of the surgical instrument of FIG. 31A, taken along line 32A-32A of FIG. 31A.
Figure 32B:
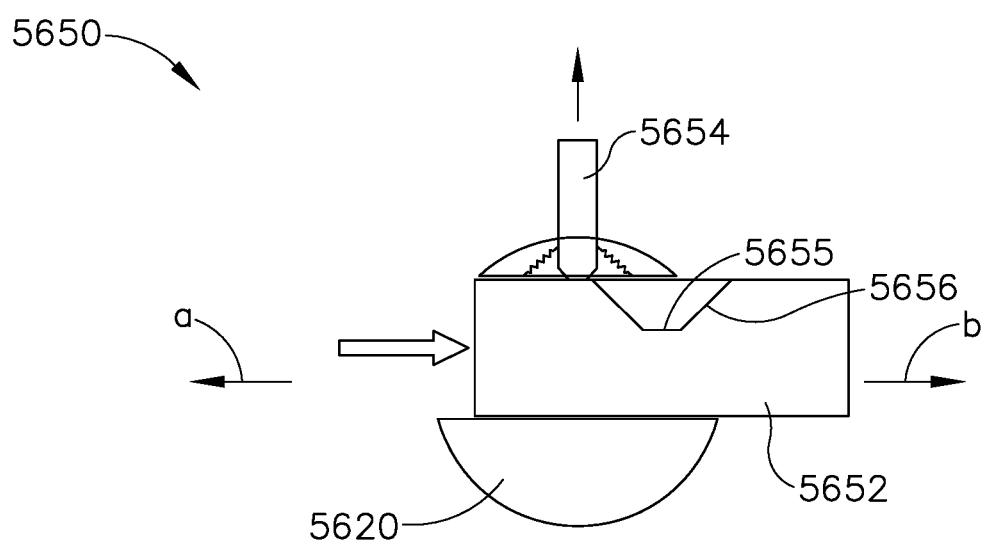
FIG. 32B depicts a cross-sectional view of the surgical instrument of FIG. 31B, taken along line 32B-32B of FIG. 31B.

In the present example, as best seen in FIGS. 32A, switch adjuster (5652) defines a pocket (5655) configured to receive blocker (5654) therein when gap spacer (5650) is in the unactuated position. Pocket (5655) includes a pair of chamfered sidewalls (5656) configured to urge or cam blocker (5654) out from pocket (5655) when switch adjuster (5652) is moved in either lateral direction. Block (5654) may define one or more complementary chamfered surfaces (5657) to facilitate the camming against chamfered sidewalls (5656). As seen in FIG. 32B, switch adjuster (5652) is a switch configured to be laterally repositioned in relation to shaft assembly (5620) to thereby extend blocker (5654) from pocket (5655). With gap spacer (5650) in the unactuated position, blocker (5654) is in a first position within pocket (5655) and substantially level with an upper surface (5622) of shaft assembly (5620), as seen in FIG. 31A. With gap spacer (5650) in the actuated position, switch adjuster (5652) is configured to extend blocker (5654) to a second position extending towards clamp arm actuator (5630), as seen in FIG. 31B. In other words, the repositioning of switch adjuster (5652) in either lateral direction (a, b) is configured to urge blocker (5654) out from pocket (5655) along chamfered sidewalls (5656) until blocker (5654) is positioned along a top surface (5653) of switch adjuster (5652). With gap spacer (5650) in the actuated position, top surface (5653) is configured to maintain blocker (5654) until switch adjuster (5652) is laterally repositioned to urge blocker (5654) back into pocket (5655), as shown in FIG. 32A.

Figure 31C:
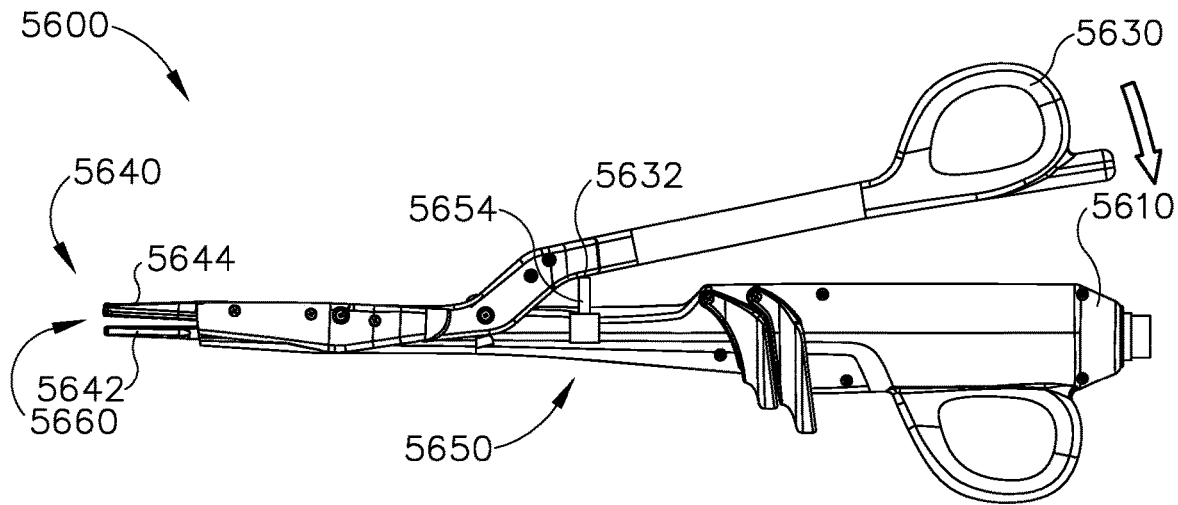
FIG. 31C depicts a side elevational view of the surgical instrument of FIG. 31A, with the gap spacer in the actuated position and the end effector in an intermediate position.
Figure 31D:
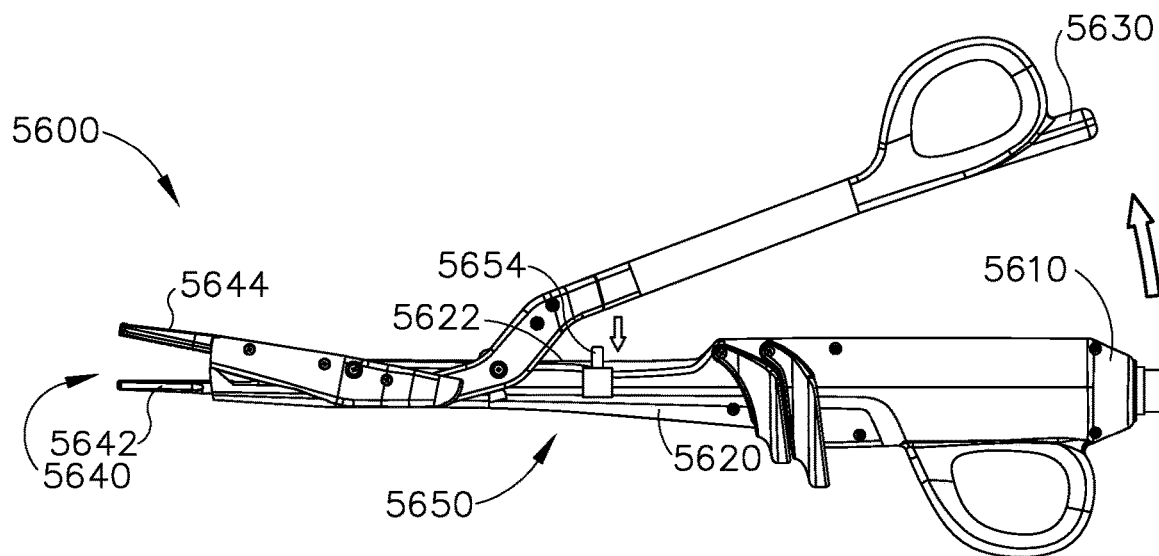
FIG. 31D depicts a side elevational view of the surgical instrument of FIG. 31A, with the gap spacer returned to the unactuated position and the blocker extending away from the clamp arm actuator, with the end effector extended back to the open position.

As seen in FIG. 31C, with gap spacer (5650) in the actuated position, blocker (5654) is configured to inhibit clamp arm actuator (5630) moving relative to handle body (5610) to the closed configuration by wedging against a blocked surface (5632) of clamp arm actuator (5630). In this instance, blocker (5654) is a protrusion extending from shaft assembly (5620) at a transverse length and is configured to impede the downward movement of blocked surface (5632) towards shaft assembly (5620). The transverse length of blocker (5654) is configured to corresponds with a predetermined gap (5660) formed between ultrasonic blade (5642) and clamp arm (5644), as seen in FIG. 31C. FIG. 31D shows clamp arm actuator (5630) away from handle body (5610) to the open configuration and gap spacer (5650) in the unactuated position. As gap spacer (5650) is transitioned from the actuated position to the unactuated position, blocker (5654) is received within pocket (5655) and thus transversely retracted back to the first position with blocker (5654) substantially level with upper surface (5622) of shaft assembly (5620). In this instance, with gap spacer (5650) in the unactuated position, clamp arm actuator (5630) is configured to move towards handle body (5610) to the closed configuration without encountering blocker (5654) to thereby move ultrasonic blade (5642) and clamp arm (5644) to the closed position. Although not shown, it will be apparent to those of ordinary skill in the art that gap spacer (5650) may alternatively be positioned along handle body (5610) or clamp arm actuator (5630).

vi. Rotatable Spacer with Knob Adjuster

Figure 33A:
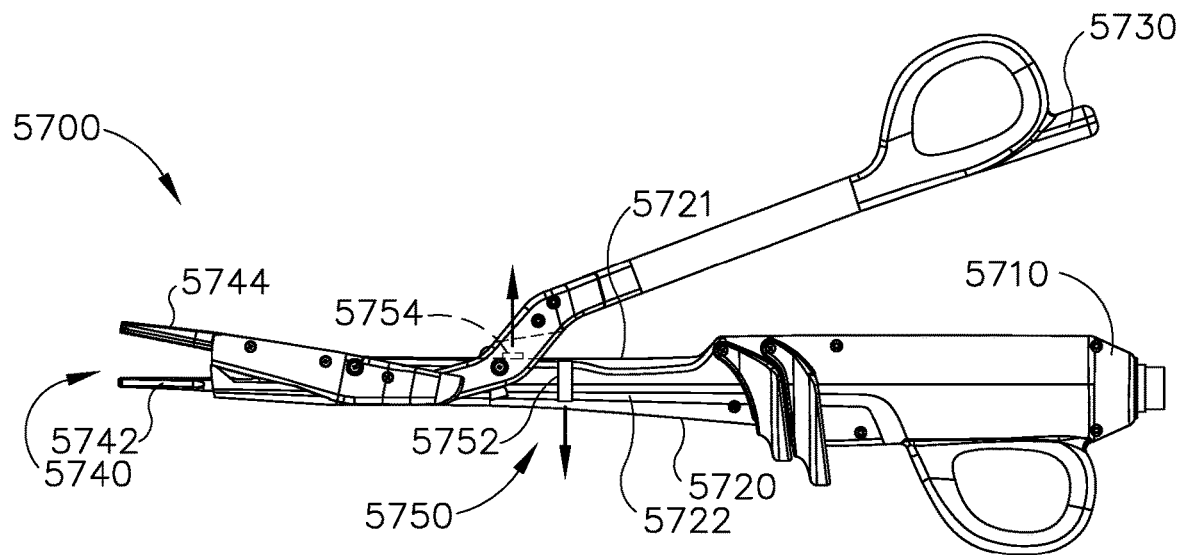
FIG. 33A depicts a side elevational view of a ninth exemplary surgical instrument including an exemplary rotatable spacer and an end effector, with the rotatable spacer in an unactuated position and the end effector in an open position.
Figure 33B:
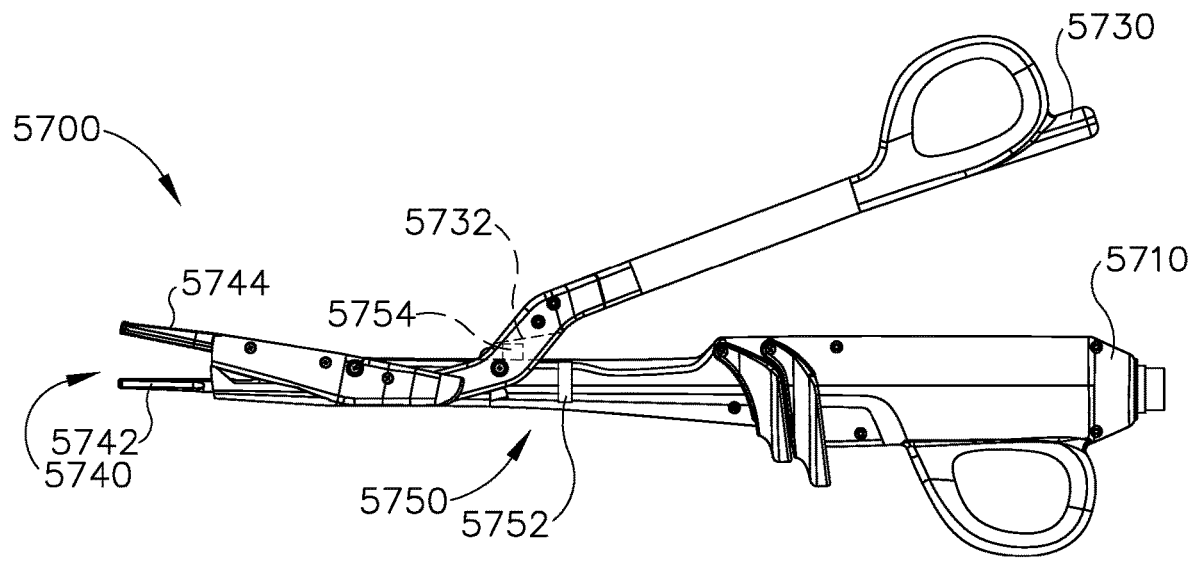
FIG. 33B depicts a side elevational view of the surgical instrument of FIG. 33A, with the rotatable spacer in an actuated position and a blocker extending towards a clamp arm actuator.

FIG. 33A shows an exemplary rotatable spacer (5750) positioned within a shaft assembly (5720) of a ninth exemplary surgical instrument (5700). Rotatable spacer (5750) includes a knob adjuster (5752) positioned along a side (5722) of shaft assembly (5720) and a blocker (5754) extending from a top side (5721) of shaft assembly (5720), as best seen in FIG. 34. Rotatable spacer (5750) is configured to be moved from an unactuated position, as seen in FIG. 33A, to an actuated position as seen in FIG. 33B. With rotatable spacer (5750) in the unactuated position, an end effector (5740) of surgical instrument (5700) is configured to close an ultrasonic blade (5742) and a clamp arm (5744) without interruption from rotatable spacer (5750). As seen in FIG. 33B, however, with rotatable spacer (5750) in the actuated position, blocker (5754) is extended transversely from shaft assembly (5720) towards a clamp arm actuator (5730). In this instance, blocker (5754) is configured to inhibit clamp arm actuator (5730) moving towards handle body (5710) to a closed configuration by blocking the downward movement of clamp arm actuator (5730) relative to handle body (5710).

As best seen in FIGS. 35A-35B, knob adjuster (5752) is a knob connected to a wheel (5755) positioned within shaft assembly (5720). Wheel (5755) has a varying diameter about a center (5756) and is configured to rotate about center (5756) in response to rotation of knob adjuster (5752). Blocker (5754) is movably positioned atop wheel (5755) at a resting point (5757) and is configured to extend from shaft assembly (5720) through an opening (5724). Wheel (5755) includes an end wall (5758) configured to engage blocker (5754) to thereby impede the continued rotation of wheel (5755) once blocker (5754) encounters end wall (5758), thus providing an end point feature for the rotation of knob adjuster (5782). In this instance, end wall (5758) is operable to provide an indication to an operator that blocker (5754) may be urged upwards from shaft assembly (5720) by rotating knob adjuster (5752) in an opposite direction away from end wall (5758). Knob adjuster (5752) is configured to rotate wheel (5755) and thereby extend blocker (5754) from shaft assembly (5720) as the diameter of resting point (5757) increases along wheel (5755). As it will be apparent to those of ordinary skill in the art in view of the teachings herein, blocker (5754) is configured to extend through opening (5724) until resting point (5757) returns to the portion of wheel (5755) that includes the smallest diameter, as seen in FIG. 35A.

Figure 33C:
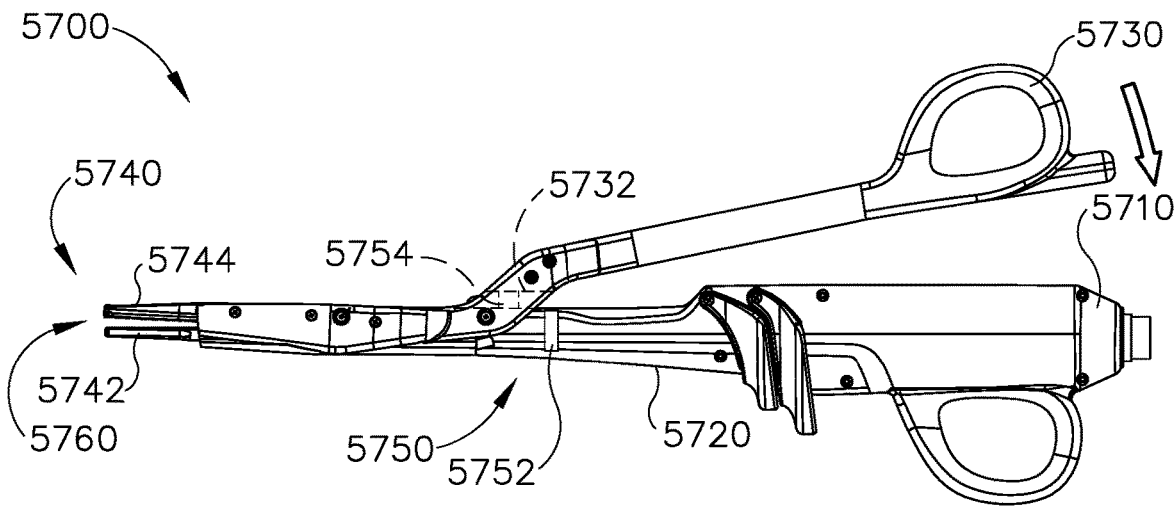
FIG. 33C depicts a side elevational view of the surgical instrument of FIG. 33A, with the rotatable spacer in the actuated position and the end effector in an intermediate position.
Figure 33D:
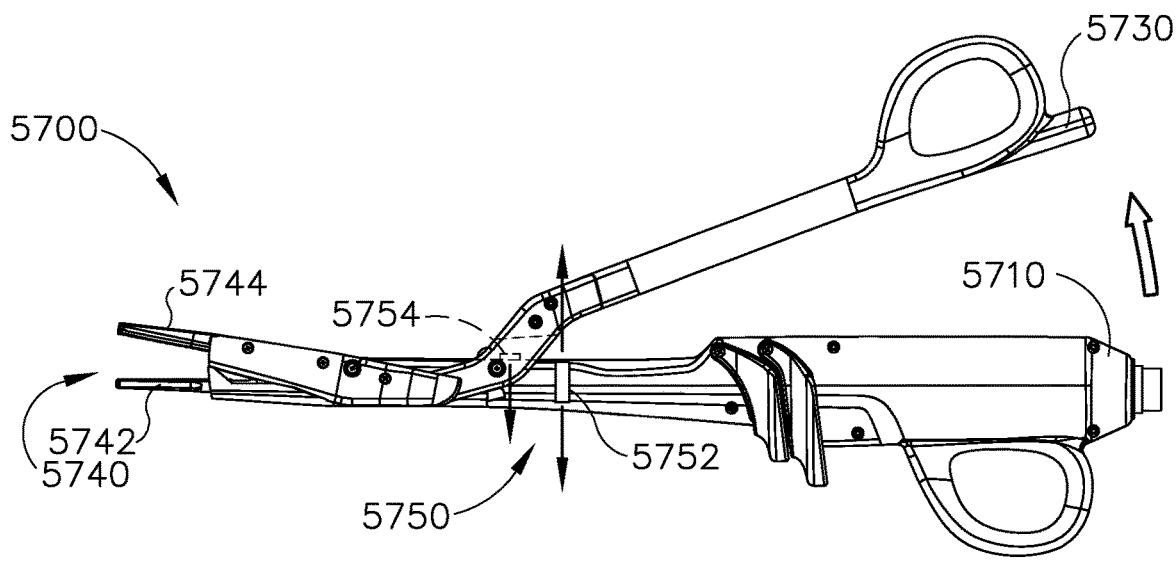
FIG. 33D depicts a side elevational view of the surgical instrument of FIG. 33A, with the rotatable spacer returned to the unactuated position and the blocker extending away from the clamp arm actuator, with the end effector extended back to the open position.

In the present example, as shown in FIG. 35A, with rotatable spacer in the unactuated position, blocker (5754) is substantially within shaft assembly (5720). In this instance, resting point (5757) has the smallest diameter along wheel (5755). As rotatable spacer (5750) is transitioned to the actuated position, through the rotation of knob adjuster (5752), wheel (5755) rotates about center (5756) and the diameter of wheel (5755) at resting point (5757) increases. As it will be apparent, as the diameter of wheel (5755) increases at resting point (5757), blocker (5754) is configured to urge upward through opening (5724). As seen in FIG. 33A, knob adjuster (5752) is configured to be rotated downward in relation to shaft assembly (5720) to thereby rotate wheel (5755) and urge blocker (5754) towards clamp arm actuator (5730). As seen in FIG. 33C, the rotation of knob adjuster (5752) urges blocker (5754) through opening (5724) until blocker (5754) is positioned beneath a blocked surface (5732) of clamp arm actuator (5730). Blocker (5754) is a protrusion configured to transversely extend from shaft assembly (5720) at a length that corresponds with a predetermined gap (5760) formed between ultrasonic blade (5742) and clamp arm (5744). With rotatable spacer (5750) in the actuated position, blocker (5754) is configured to inhibit clamp arm actuator (5730) moving towards handle body (5710) to the closed configuration by wedging blocker (5754) against blocked surface (5732). In this instance, blocker (5754) is configured to impede the downward movement of blocked surface (5732).

With rotatable spacer in the actuated position, resting point (5757) is configured to maintain blocker (5754) at the largest diameter of wheel (5755) until knob adjuster (5752) is further rotated to reposition resting point (5757) at the smallest diameter of wheel (5755). In this instance, as rotatable spacer (5750) is transitioned to the unactuated position, knob adjuster (5752) is configured to allow blocker (5754) to retract downward into shaft assembly (5720), as seen in FIG. 35B. This retraction may be accomplished via gravity or by pressure from clamp arm actuator (5730) or any other element of instrument (5700). FIG. 35D shows clamp arm actuator (5730) moved away from handle body (5710) to the open configuration and rotatable spacer (5750) in the unactuated position. With rotatable spacer (5750) returned to the unactuated position, blocker (5754) is permitted to retract back to the first position due to the absence of upward pressure from wheel (5755). In this instance, clamp arm actuator (5730) is configured to move towards handle body (5710) to the closed configuration without encountering blocker (5754) to thereby move ultrasonic blade (5742) and clamp arm (5744) to the closed position.

vii. Pivotable Spacer with Pivotable Adjuster

Figure 36A:
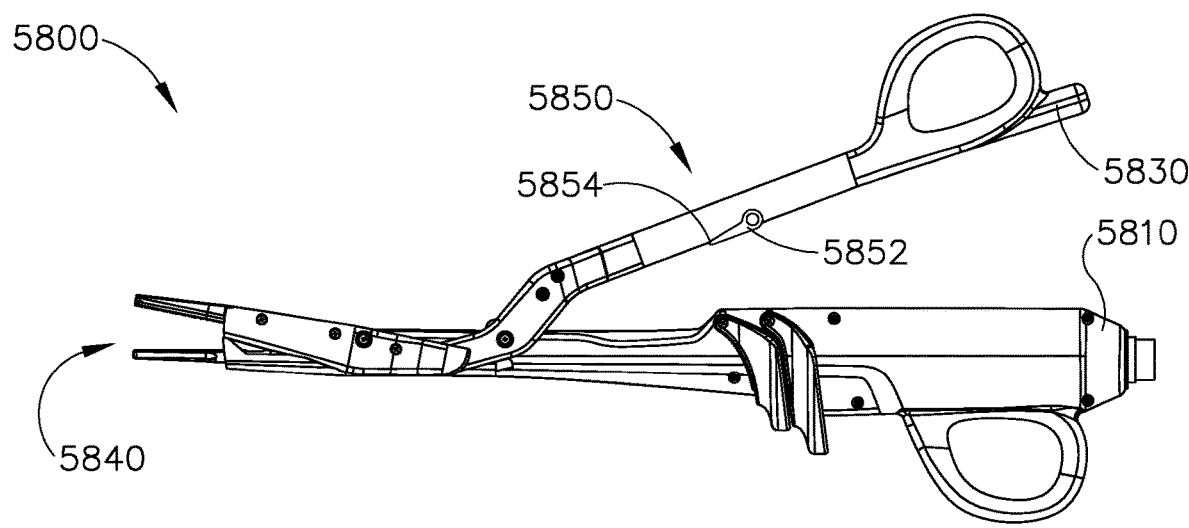
FIG. 36A depicts a side elevational view of a tenth exemplary surgical instrument including an exemplary pivotable spacer and an end effector, with the pivotable spacer in an unactuated position and the end effector in an open position.
Figure 36B:
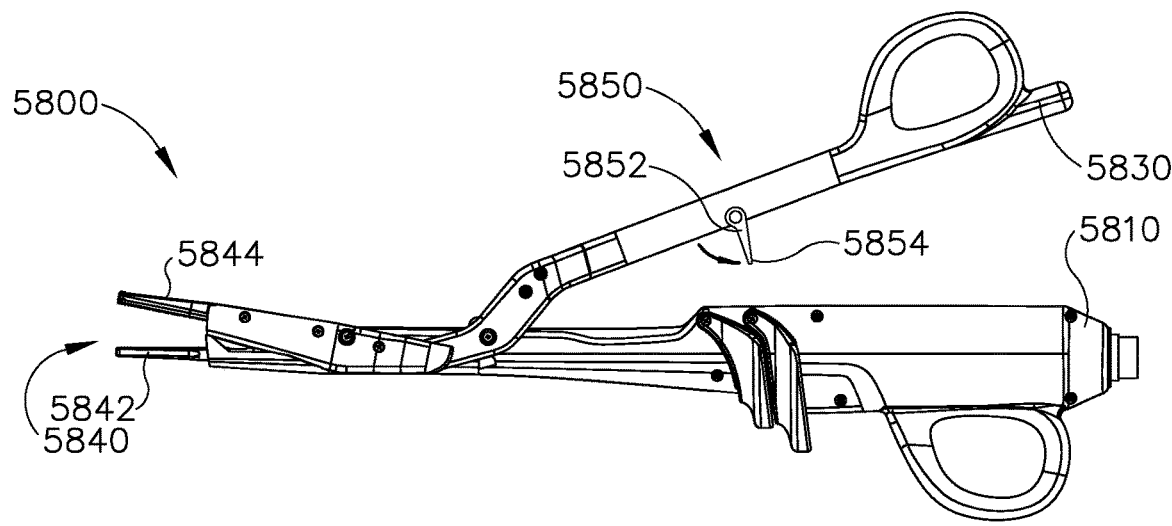
FIG. 36B depicts a side elevational view of the surgical instrument of FIG. 36A, with the pivotable spacer in an actuated position and a blocker extending towards a handle body.

FIGS. 36A-36D show an exemplary pivotable spacer (5850) positioned along a clamp arm actuator (5830) of a tenth exemplary surgical instrument (5800). Pivotable spacer (5850) includes a pivotable adjuster (5852) and a blocker (8854). Pivotable spacer (5850) is configured to move from an unactuated position, as seen in FIG. 36A, to an actuated position as shown in FIG. 36B. With pivotable spacer (5850) in the unactuated position, an end effector (5840) of surgical instrument (5800) is configured to close an ultrasonic blade (5842) and a clamp arm (5844) without interruption from pivotable spacer (5850). However, with pivotable spacer (5850) in the actuated position, blocker (5854) is extended transversely downward from clamp arm actuator (5830) and towards a handle body (5810) of surgical instrument (5800), as seen in FIG. 36B. In this instance, blocker (5854) is configured to inhibit clamp arm actuator (5830) moving toward handle body (5810) by blocking the downward movement of clamp arm actuator (5830) relative to handle body (5810).

Figure 36C:
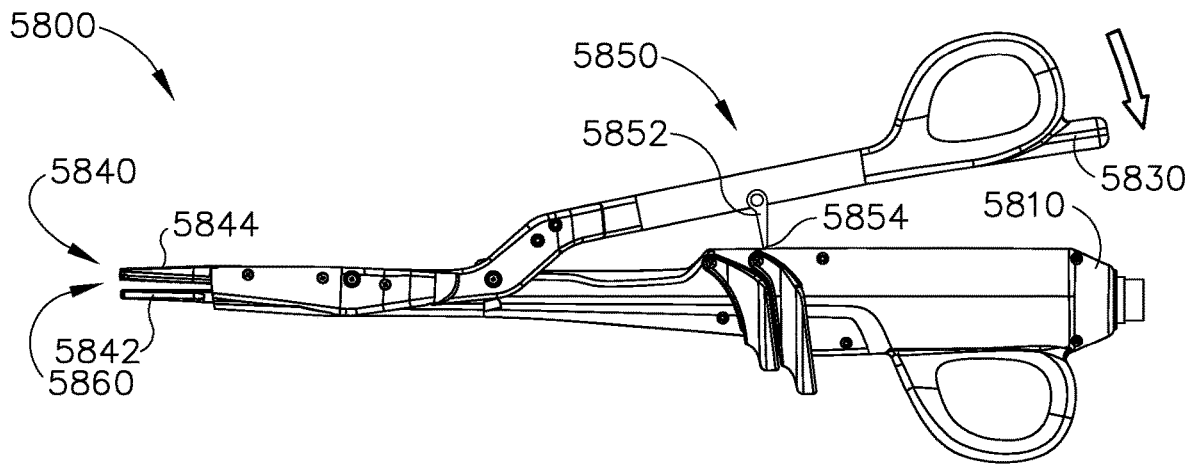
FIG. 36C depicts a side elevational view of the surgical instrument of FIG. 36A, with the pivotable spacer in the actuated position and the end effector in an intermediate position.

In the present example, as seen in FIGS. 36A-36B, pivotable adjuster (5852) is configured to pivot towards handle body (5810) to thereby extend blocker (5854) from a first position, generally parallel with clamp arm actuator (5830), to a second position, generally perpendicular to clamp arm actuator (5830) and extending toward handle body (5810). With pivotable spacer (5850) in the actuated position, as seen in FIG. 36C, blocker (5854) extends towards handle body (5810) and is configured to inhibit clamp arm actuator (5830) from moving towards handle body (5810) to a closed configuration. In this instance, blocker (5854) is a protrusion configured to extend from clamp arm actuator (5830) at a transverse length that corresponds to a predetermined gap (5860) formed between ultrasonic blade (5842) and clamp arm (5844). With pivotable spacer (5850) in the actuated position, blocker (5854) is configured to maintain end effector (5840) at an intermediate position.

Figure 36D:
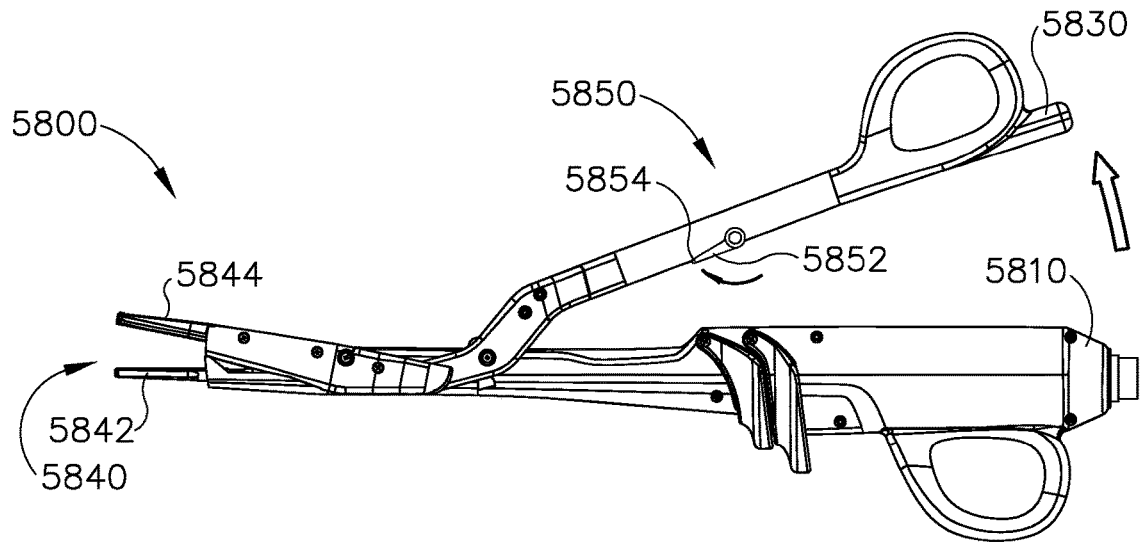
FIG. 36D depicts a side elevational view of the surgical instrument of FIG. 36A, with the pivotable spacer returned to the unactuated position and the blocker extending away from the handle body, with the end effector extended back to the open position.

Pivotable adjuster (5852) is further configured to pivot away from handle body (5810) to thereby retract blocker (5854) from the second position to the first position. FIG. 36D shows clamp arm actuator (5830) moved away from handle body (5810) and pivotable spacer (5850) in the unactuated position. As pivotable spacer (5850) is transitioned from the actuated position to the unactuated position, blocker (5854) is configured to reversibly pivot back to the first position with blocker (5854) being parallel with clamp arm actuator (5830). With pivotable spacer (5850) in the unactuated position, clamp arm actuator (5830) is configured to move towards handle body (5810) to the closed configuration without blocker (5854) encountering handle body (5810) to thereby move ultrasonic blade (5842) and clamp arm (5844) to the closed position.

viii. Biasing Spacer with Pivotable Blocker

Figure 37A:
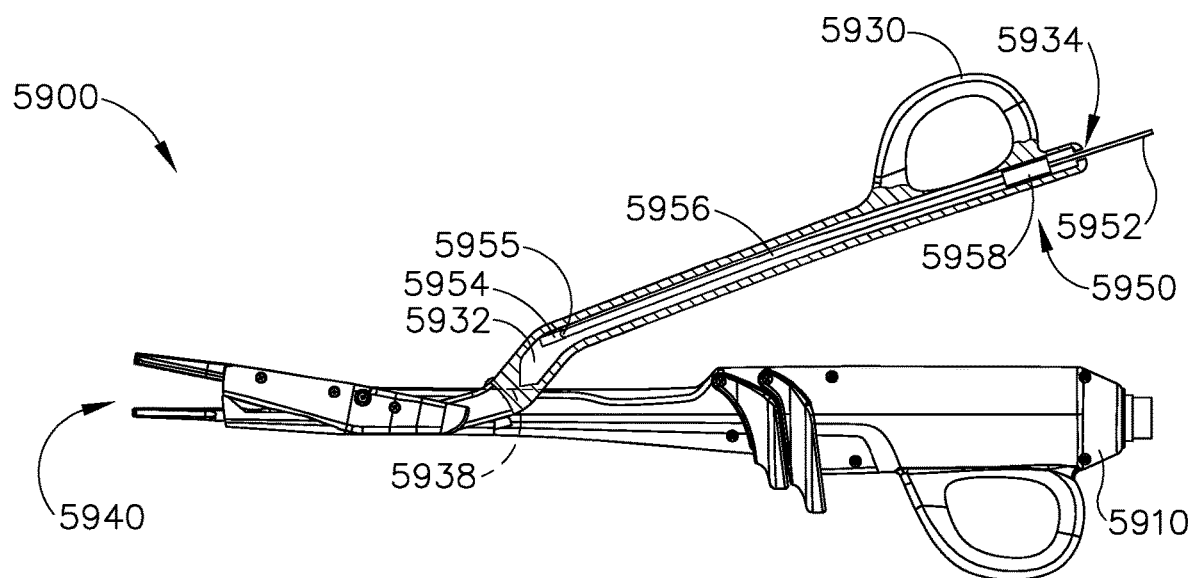
FIG. 37A depicts a side elevational view of an eleventh exemplary surgical instrument including an exemplary biasing spacer contained within a clamp arm actuator and an end effector, with the biasing spacer in an unactuated position and the end effector in an open position.
Figure 37B:
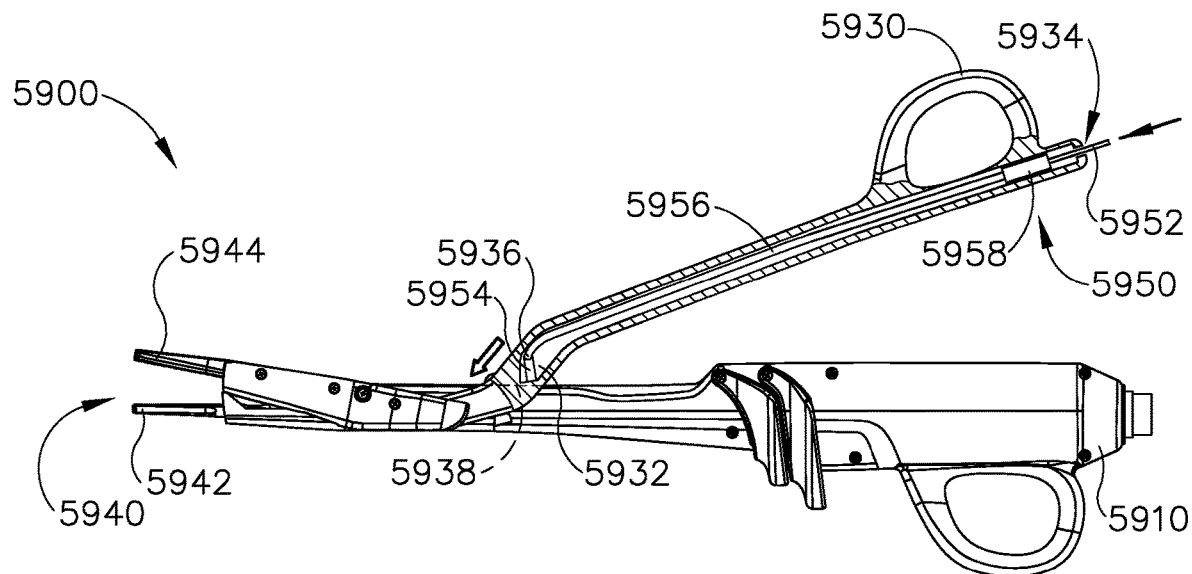
FIG. 37B depicts a side elevational view of the surgical instrument of FIG. 37A, with the biasing spacer in an actuated position and a blocker extending towards a shaft assembly.

FIG. 37A shows an exemplary biasing spacer (5950) positioned within a channel (5932) of a clamp arm actuator (5930) of an eleventh exemplary surgical instrument (5900). Biasing spacer (5950) includes an extension (5956) extending between a toggle adjuster (5952), on a proximal end of extension (5956), and a pivotable blocker (5954), on a distal end of extension (5956). Channel (5932) of clamp arm actuator (5930) includes a proximal opening (5934) and a distal opening (5938). Toggle adjuster (5952) extends proximally from channel (5932) at proximal opening (5934) and is operatively connected to the proximal end of extension (5956) through a biasing mechanism (5958). Biasing spacer (5950) is configured to move from an unactuated position, as seen in FIG. 37A, to an actuated position as shown in FIG. 37B. Pivotable blocker (5954) is contained within channel (5932) and is pivotably connected to the distal end of extension (5956) about a rotation point (5955). With biasing spacer (5950) in the unactuated position, an end effector (5940) of surgical instrument (5900) is configured to close an ultrasonic blade (5942) and a clamp arm (5944) to a closed position without interruption from biasing spacer (5950). However, with biasing spacer (5950) in the actuated position, pivotable blocker (5954) extends distally through distal opening (5938) of channel (5932) towards a blocked surface (5922) of shaft assembly (5920), as seen in FIG. 37B. In this instance, pivotable blocker (5954) is configured to inhibit clamp arm actuator (5930) from moving towards handle body (5910) to the closed configuration by blocking the downward movement of clamp arm actuator (5930) relative to handle body (5910)

In the present example, toggle adjuster (5952) is a button that is configured to be clicked distally towards channel (5932) of clamp arm actuator (5930) to actuate biasing mechanism (5938). Biasing mechanism (5938) is configured to translate extension (5956) and pivotable blocker (5954) through channel (5932). With biasing spacer (5950) in the unactuated position, pivotable blocker (5954) and extension (5956) are in a first position, with pivotable blocker (5954) substantially parallel with extension (5956) as seen in FIG. 37A. With biasing spacer (5950) in the actuated position, pivotable blocker (5954) and extension (5956) are in a second position, with pivotable blocker (5954) pivotably transverse to extension (5956) about rotation point (5955), as shown in FIG. 139B. The distal translation of extension (5956) in channel (5932) is configured to direct pivotable blocker (5954) against an angled wall (5936) of channel (5932). Angled wall (5936) is configured to redirect pivotable blocker (5954) through distal opening (5938) and towards blocked surface (5922). Biasing mechanism (5958) is further configured to bias extension (5956) to thereby maintain pivotable blocker (5954) in the second position until toggle adjuster (5952) is clicked distally towards channel (5932) to thereby retract extension (5956) and pivotable blocker (5954) back to the first position. Biasing mechanism (5956) may include a cam, plunger, stop member, spring mechanism, or other biasing mechanism to provide for the retractable extension of pivotable blocker (5954), as will be apparent to those of ordinary skill in the art in view of the teachings herein.

Figure 37C:
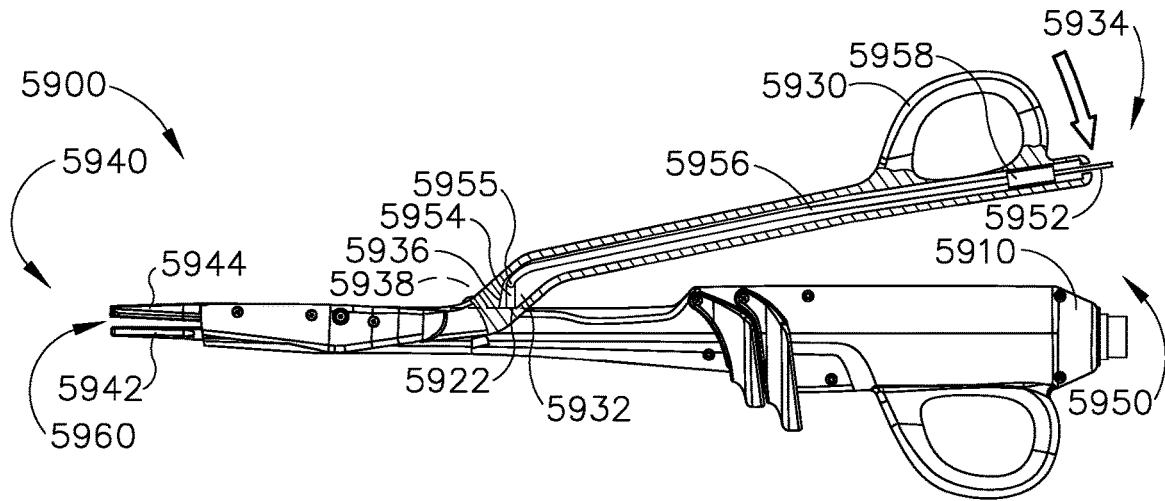
FIG. 37C depicts a side elevational view of the surgical instrument of FIG. 37A, with the biasing spacer in the actuated position and the end effector in an intermediate position.
Figure 37D:
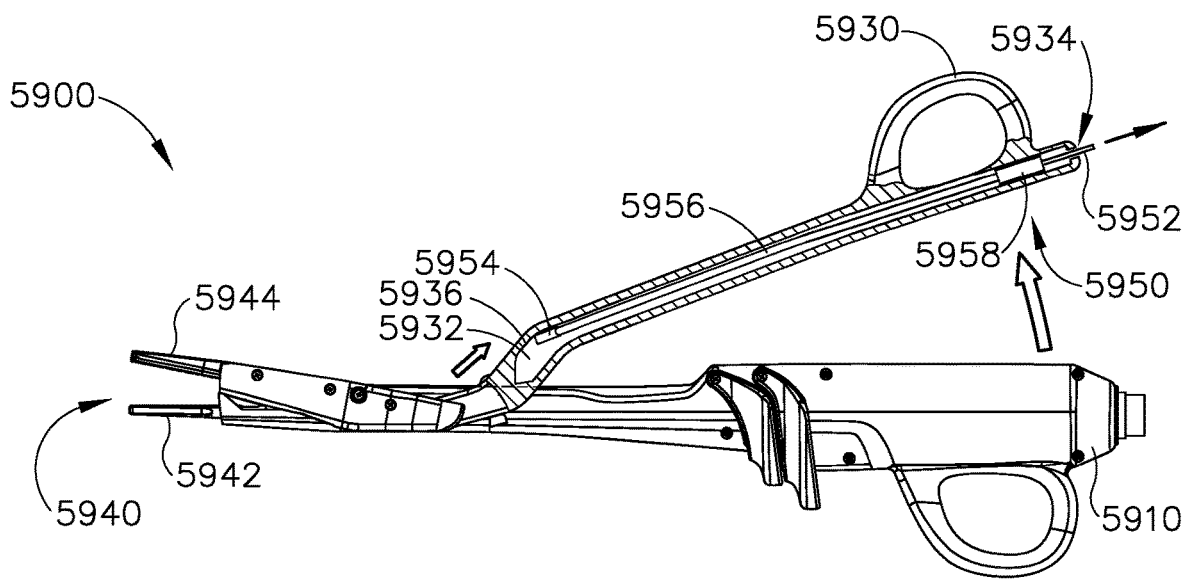
FIG. 37D depicts a side elevational view of the surgical instrument of FIG. 37A, with the biasing spacer returned to the unactuated position and the blocker extending away from the shaft assembly, with the end effector extended back to the open position.

As seen in FIG. 37C, with biasing spacer (5950) in the actuated position, pivotable blocker (5954) is configured to inhibit clamp arm actuator (5930) moving towards handle body (5910) to the closed configuration. In this instance, pivotable blocker (5954) is configured to wedge against blocked surface (5922) of shaft assembly (5920). In this instance, pivotable blocker (5954) is a protrusion configured to transversely extend from extension (5956) at a length that corresponds with a predetermined gap (5960) formed between ultrasonic blade (5942) and clamp arm (5944). FIG. 37D shows clamp arm actuator (5930) moved away from handle body (5910) and biasing spacer (5950) in the unactuated position. Biasing spacer (5950) is transitioned from the actuated position to the unactuated position through the distal actuation of toggle adjuster (5952). In other words, toggle adjuster (5952) is configured to advance and retract pivotable blocker (5954) within channel (5932) by clicking toggle adjuster (5952) in the same distal direction, relative to channel (5932). With biasing spacer (5950) in the unactuated position, pivotable blocker (5954) is pivotably retracted back to the first position with pivotable blocker (5954) being parallel with extension (5956). In this instance, clamp arm actuator (5930) is configured to move toward handle body (5910) to the closed configuration without encountering pivotable blocker (5954) to thereby move ultrasonic blade (5942) and clamp arm (5944) to the closed position. Although not shown, it will be apparent to those of ordinary skill in the art that biasing spacer (5950) may alternatively be positioned along handle body (5910) or clamp arm actuator (5930).

ix. Rotatable Spacer with Receiving Slot

Figure 38A:
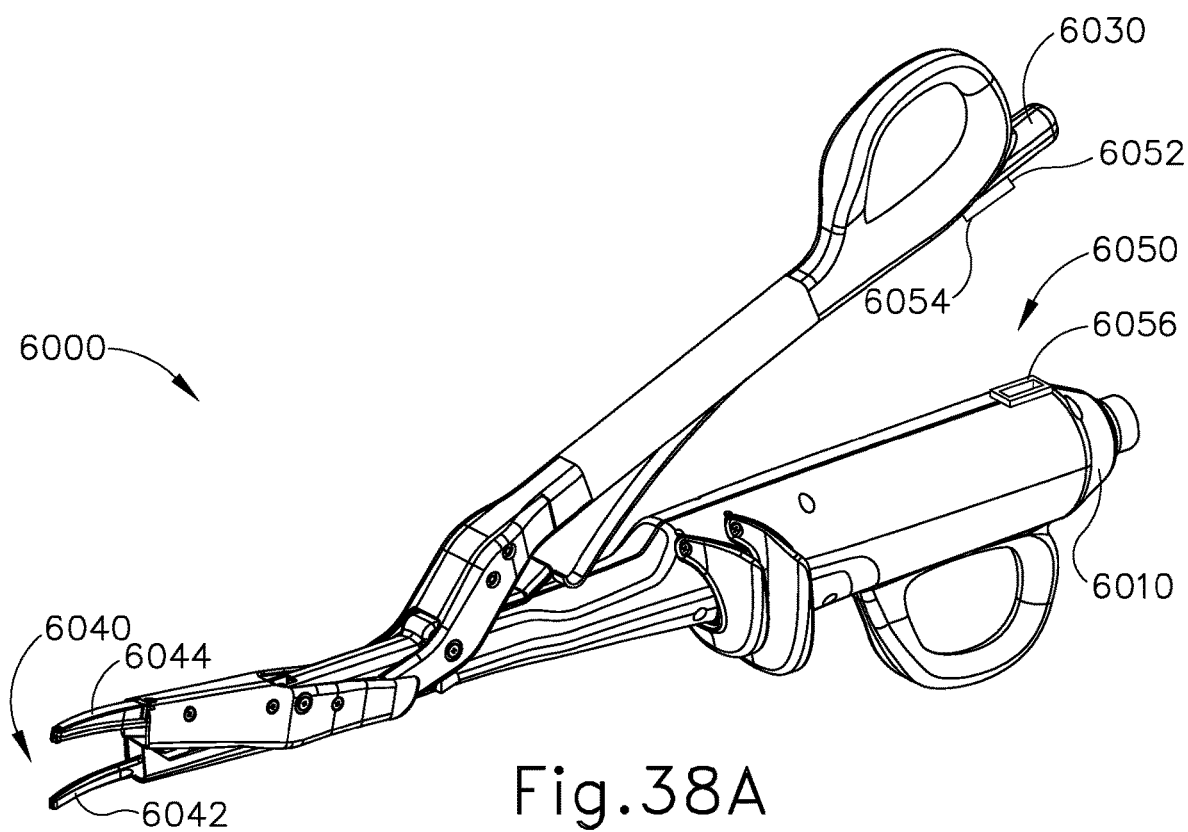
FIG. 38A depicts a side elevational view of a twelfth exemplary surgical instrument including exemplary alternative rotatable spacer and an end effector, with the rotatable spacer in an unactuated position and the end effector in an open position.
Figure 38B:
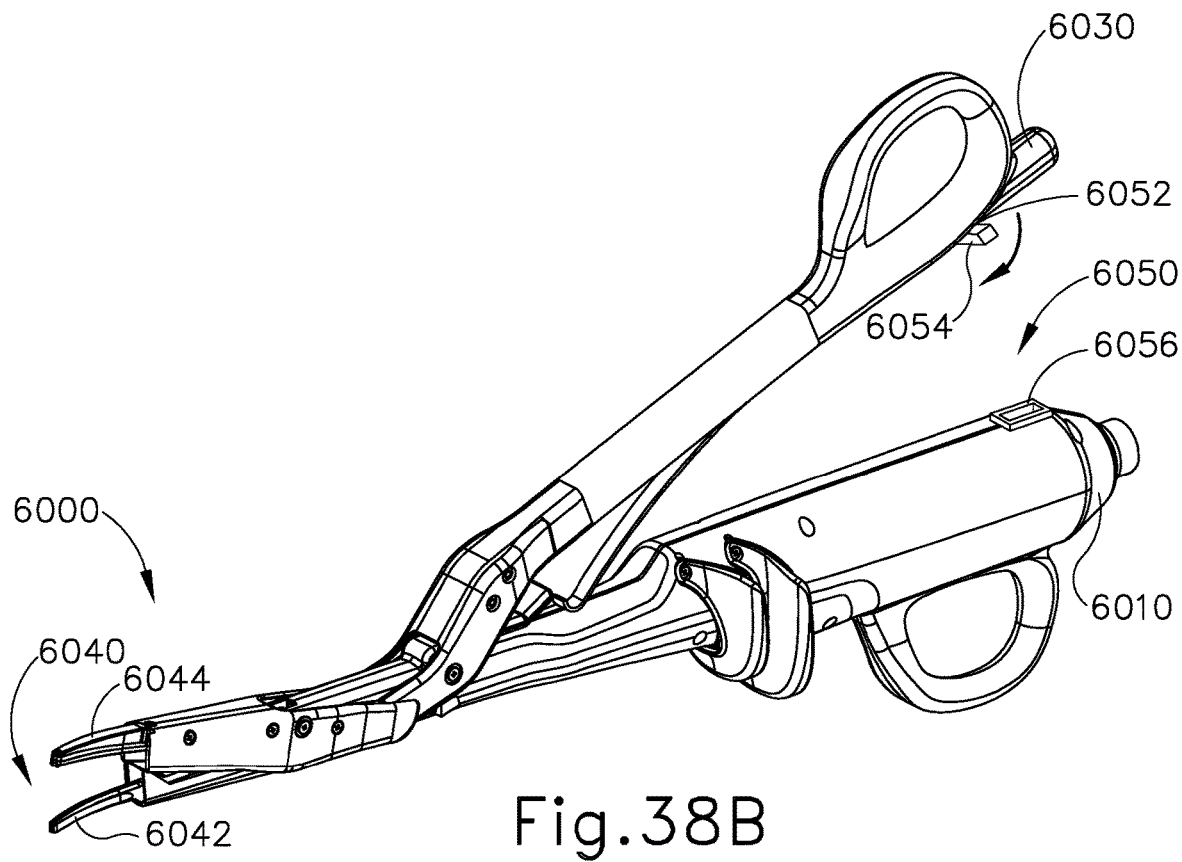
FIG. 38B depicts a side elevational view of the surgical instrument of FIG. 38A, with the rotatable spacer in an actuated position and a blocker extending laterally from a clamp arm actuator.
Figure 40:
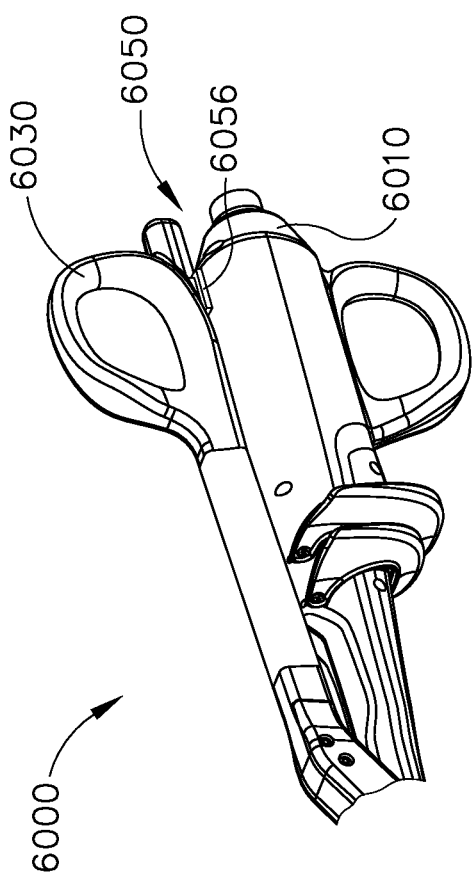
FIG. 40 depicts a partial perspective view of the rotatable spacer of FIG. 38A in the unactuated position.
Figure 42:
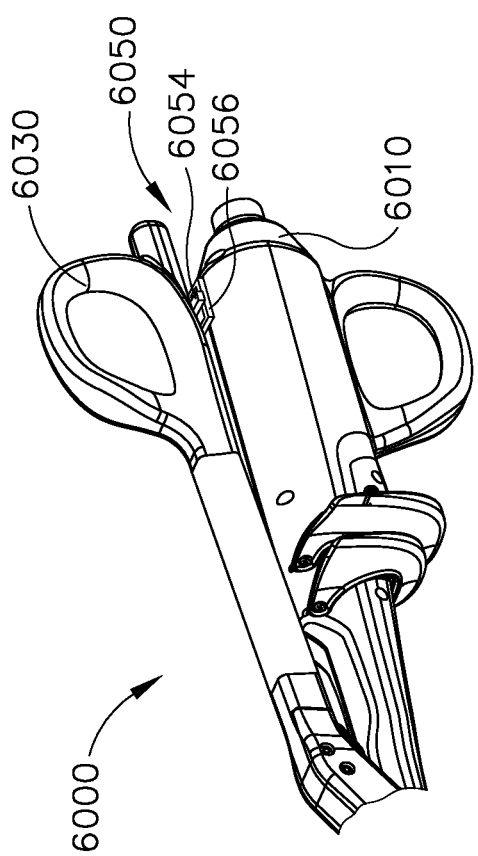
FIG. 42 depicts a partial perspective view of the rotatable spacer of FIG. 38A in the actuated position and the blocker laterally aligned with the clamp arm actuator.
Figure 39:
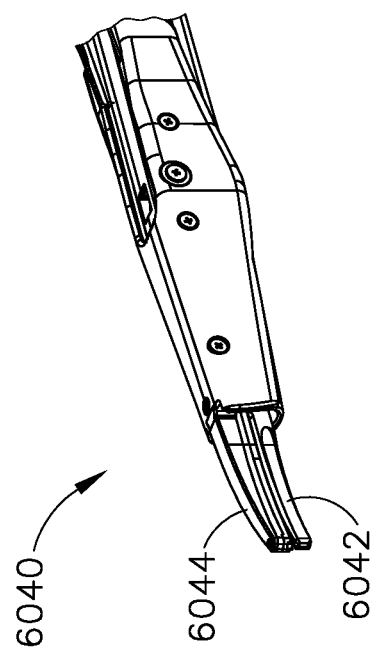
FIG. 39 depicts a partial perspective view of the end effector of FIG. 38A in a closed position.

FIG. 38A shows an exemplary rotatable spacer (6050) positioned along a clamp arm actuator (6030) of a twelfth exemplary surgical instrument (6000). Rotatable spacer (6050) includes a boss adjuster (6052), a blocker (6054) and a receiving slot (6056). Rotatable spacer (6050) is configured to move from an unactuated position, as seen in FIG. 38A, to an actuated position as shown in FIG. 38B. Receiving slot (6056) is positioned along handle body (6010) and is configured to be in parallel alignment with clamp arm actuator (6030). With rotatable spacer (6050) in the unactuated position, receiving slot (6056) is shaped and configured to receive blocker (6054), as best seen in FIG. 40. With rotatable spacer (6050) in the unactuated position, an end effector (6040) of surgical instrument (6000) is configured to close an ultrasonic blade (6042) and a clamp arm (6044) to a closed position without interruption from rotatable spacer (6050). However, with rotatable spacer (6050) in the actuated position, blocker (6054) is extended laterally from clamp arm actuator (6030) thereby being in perpendicular alignment with clamp arm actuator (6030). In this instance, blocker (6054) is prevented from being received within receiving slot (6056), as seen in FIG. 42, and further configured to inhibit clamp arm actuator (6030) from moving towards handle body (6010) to the closed configuration.

Figure 41:
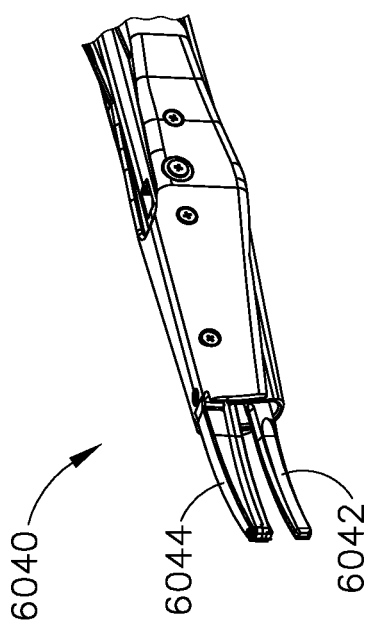
FIG. 41 depicts a partial perspective view of the end effector of FIG. 38A in an intermediate position.

In the present example, as seen in FIGS. 38A-38B, boss adjuster (6052) is configured to laterally pivot blocker (6054) from a first position, with blocker (6054) aligned with clamp arm actuator (6030), to a second position with blocker (6054) extended laterally from clamp arm actuator (6030). With rotatable spacer (6050) in the actuated position, blocker (6054) is realigned in relation to clamp arm actuator (6030) and is unable to be received within receiving slot (6056), as seen in FIG. 42. In this instance, with clamp arm actuator (6030) moved towards handle body (6010) and blocker (6054) engaged against receiving slot (6056), as seen in FIG. 42, blocker (6054) is configured to extend from receiving slot (6056) at a transverse length that corresponds to a predetermined gap (6060) formed at end effector (6040), as seen in FIG. 41. With rotatable spacer (6050) in the actuated position, blocker (6054) is configured to maintain end effector (6040) at an intermediate position.

Boss adjuster (6052) is further configured to laterally pivot blocker (6054) from the second position to the first position. FIG. 40 shows clamp arm actuator (6030) moved away handle body (6010) to the open configuration and rotatable spacer (6050) in the unactuated position. As rotatable spacer (6050) is transitioned from the actuated position to the unactuated position, blocker (6054) is configured to reversibly pivot to the first position with blocker (6054) in parallel alignment with clamp arm actuator (6030). With rotatable spacer (6050) in the unactuated position, clamp arm actuator (6030) is configured to move relative to handle body (6010) to the closed configuration with blocker (6054) configured to fit within receiving slot (6056) to thereby move ultrasonic blade (6042) and clamp arm (6044) to the closed position.

x. Static Spacer with Clamp Arm Adjuster

Figure 43A:
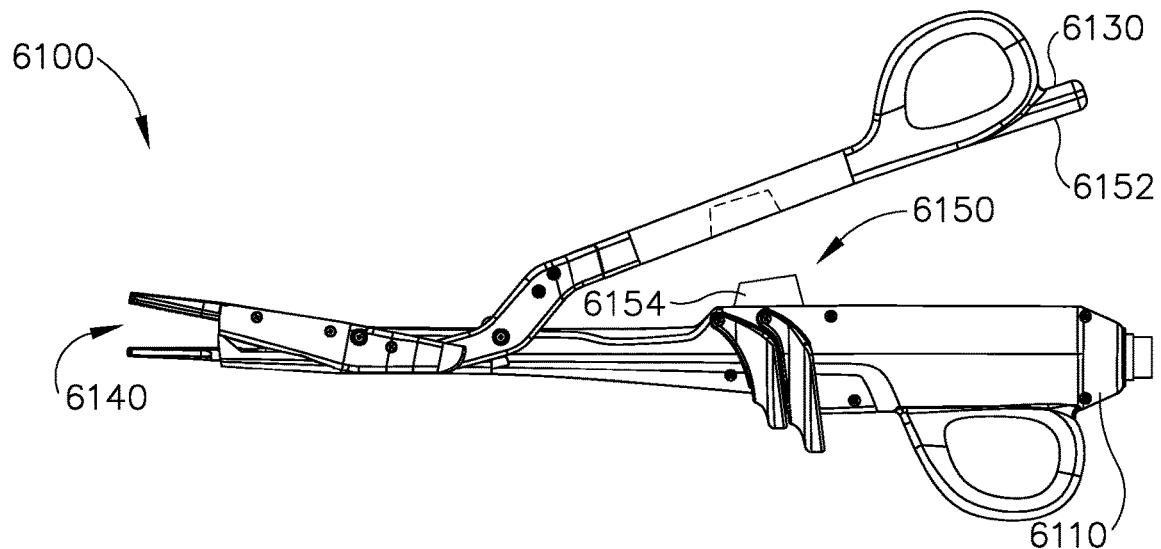
FIG. 43A depicts a side elevational view of a thirteenth exemplary surgical instrument including an exemplary static spacer and an end effector, with the static spacer in an actuated position and the end effector in an open position.
Figure 43B:
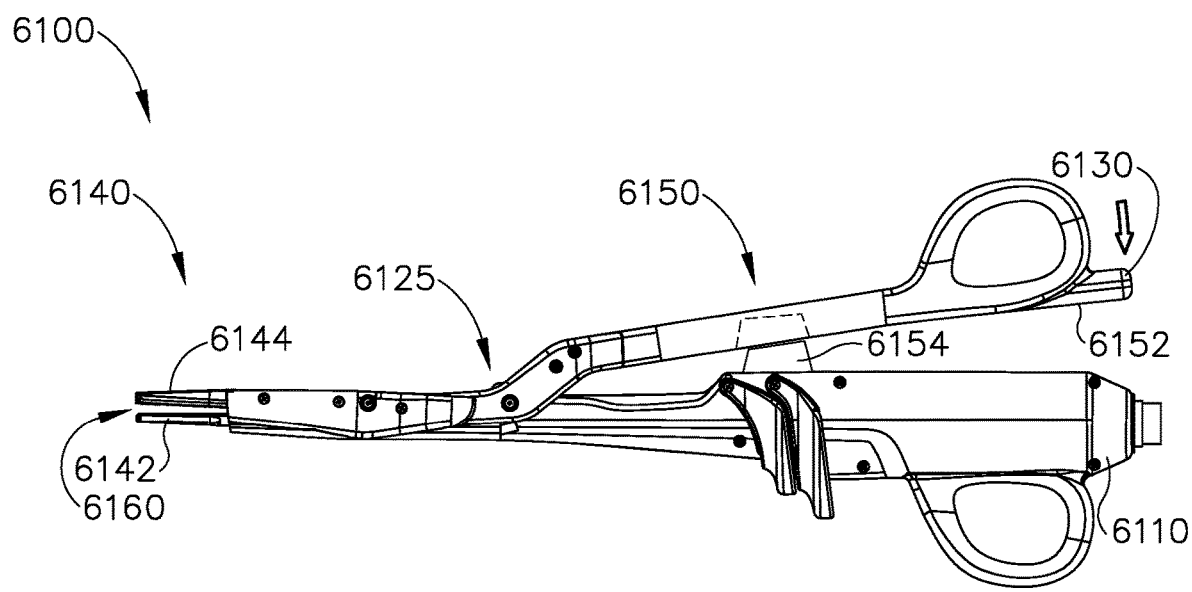
FIG. 43B depicts a side elevational view of the surgical instrument of FIG. 43A, with the static spacer in the actuated position and a blocker engaging a clamp arm actuator, with the end effector in an intermediate position.
Figures 44A, 44B:
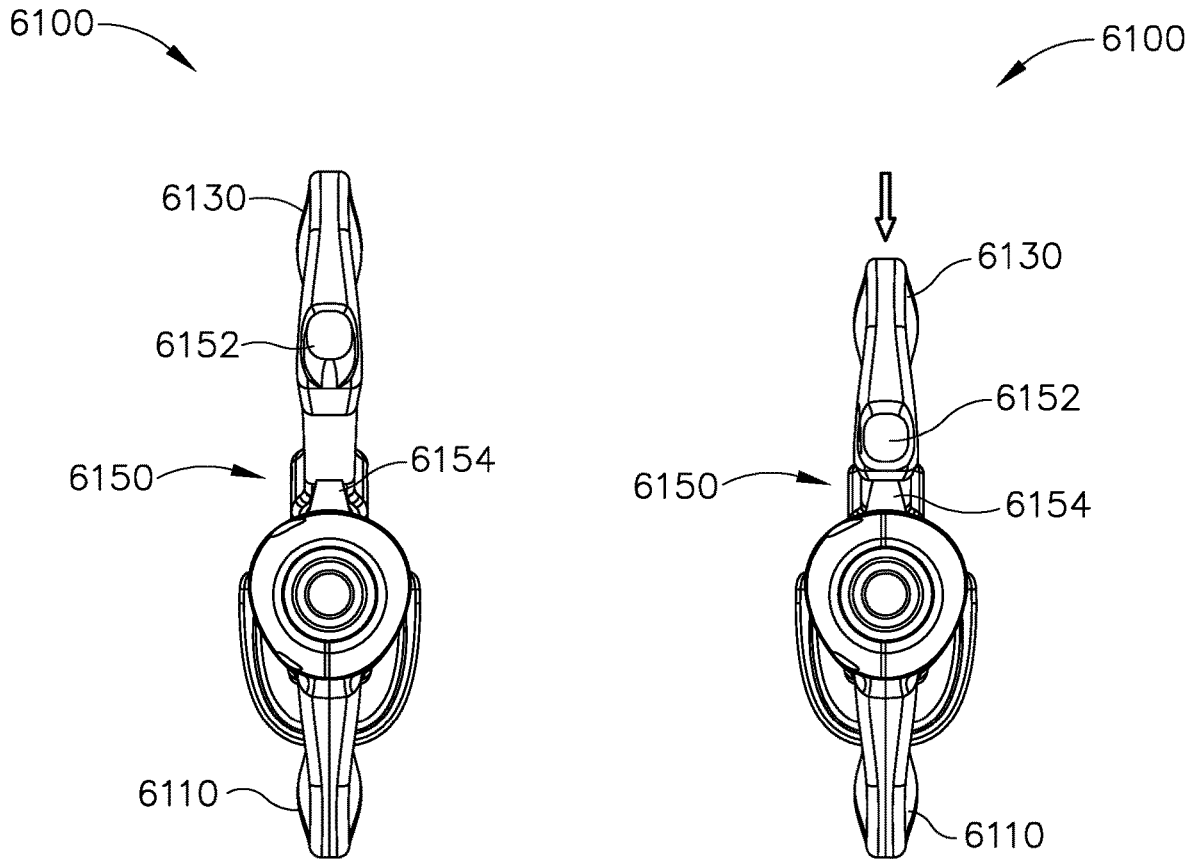
FIG. 44A depicts a rear elevational view of the surgical instrument of FIG. 43A, with the static spacer in the actuated position and the blocker disengaged from the clamp arm actuator.
FIG. 44B depicts a rear elevational view of the surgical instrument of FIG. 43A, with the static spacer in the actuated position and the blocker engaging the clamp arm actuator.
Figure 45:
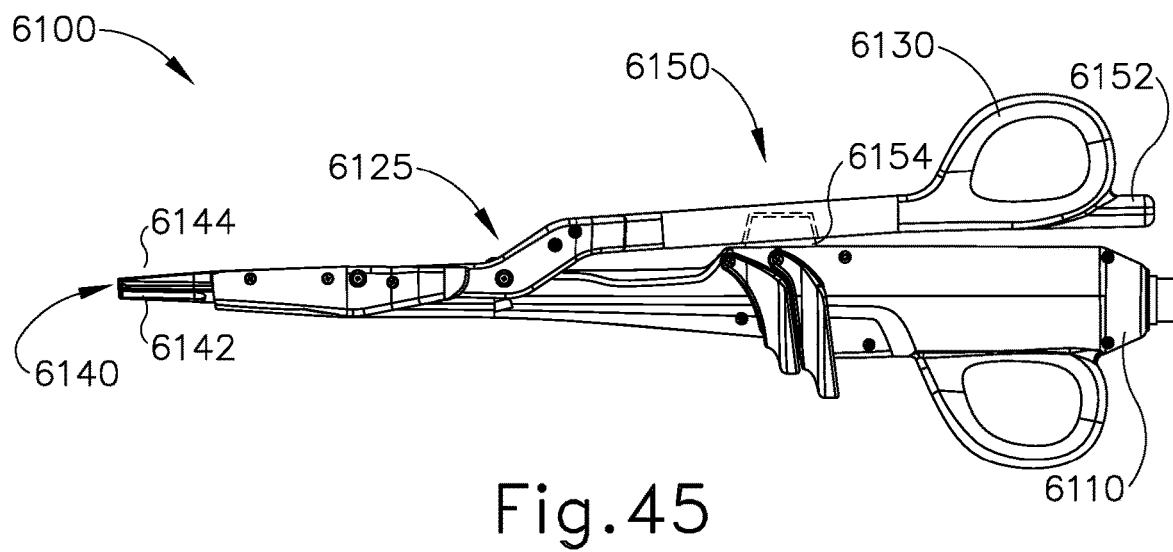
FIG. 45 depicts a side elevational view of the surgical instrument of FIG. 43A, with the static spacer in the actuated position and the blocker disengaged from the clamp arm actuator, with the end effector in an intermediate position.
Figure 46:
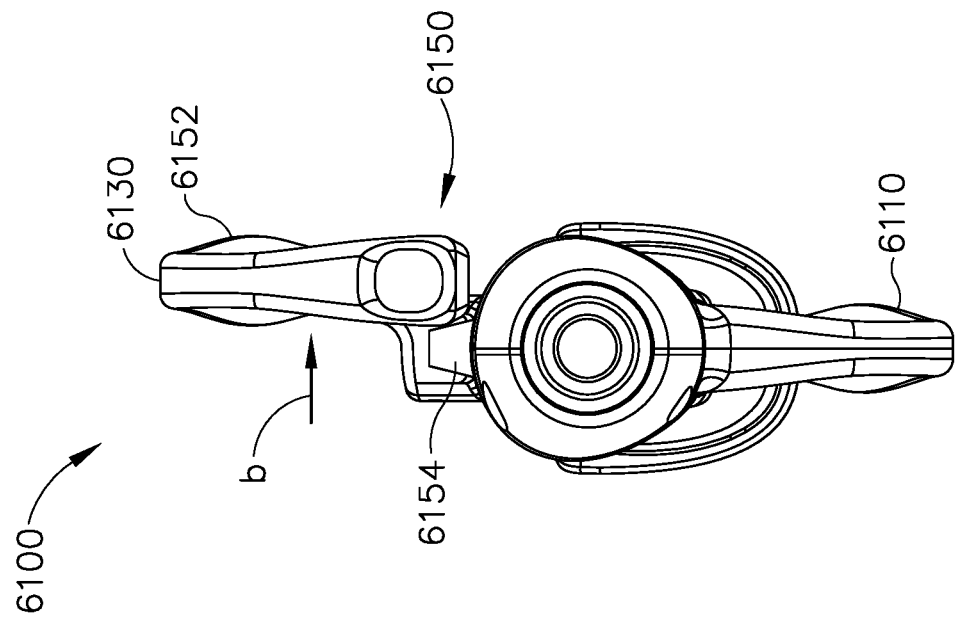
FIG. 46 depicts a rear elevational view of the surgical instrument of FIG. 43A, with the static spacer in the unactuated position and the blocker disengaged from the clamp arm actuator, with the clamp arm actuator pivoted laterally to the a first side.
Figure 47:
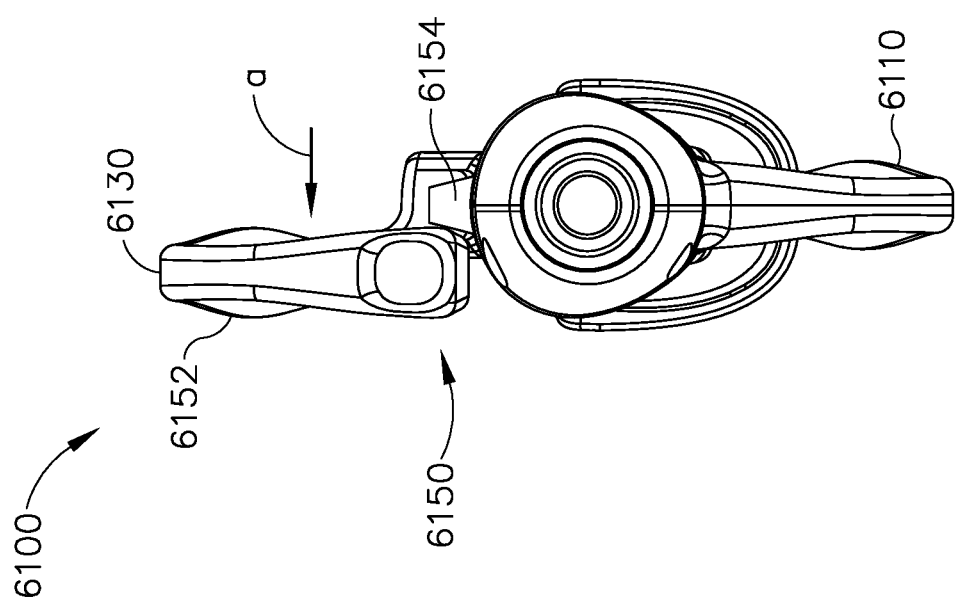
FIG. 47 depicts a rear elevational view of the surgical instrument of FIG. 43A, with the static spacer in the unactuated position and the blocker disengaged from the clamp arm actuator, with the clamp arm actuator pivoted laterally to a second side.

FIG. 43A shows an exemplary static spacer (6150) positioned along a handle body (6110) of a thirteenth exemplary surgical instrument (6100). Static spacer (6150) includes a clamp arm adjuster (6152) and a blocker (6154). Static spacer (6150) is configured to be in an initial actuated position, as seen in FIGS. 43A-43B. In this instance, blocker (6154) is positioned along handle body (6110) and is configured to fixedly protrude from handle body (6110) in a transverse direction towards clamp arm actuator (6130). Clamp arm adjuster (6152) is integral and unitary with clamp arm actuator (6130) and is configured to selectively manipulate clamp arm actuator (6130) toward handle body (6110) to engage blocker (6154), as seen in FIG. 43B. In this instance, blocker (6154) is configured to inhibit clamp arm actuator (6130) moving relative to handle body (6110) to the closed configuration as shown in FIGS. 44A-44B. Clamp arm adjuster (6130) is further configured to pivot clamp arm actuator (6130) in a lateral direction (a, b) relative to handle body (6110), as seen in FIGS. 46-47. With static spacer (6150) in the unactuated position, clamp arm actuator (6130) is configured to move towards handle body (6110) without encountering blocker (6154), as seen in FIG. 45.

In the present example, clamp arm adjuster (6152) is configured to laterally pivot clamp arm actuator (6130) about a coupling portion (6125) from a first position, with clamp arm actuator (6130) in longitudinal alignment with handle body (6110), to a second position with clamp arm actuator (6130) laterally offset from handle body (6110). In this instance, clamp arm adjuster (6152) is unitary with clamp arm actuator (6130). With static spacer (6150) in the actuated position, clamp arm actuator (6130) is in longitudinal alignment with handle body (6110) and handle body (6154), as seen in FIGS. 44A-44B. In this instance, blocker (6154) is configured to inhibit clamp arm actuator (6130) from moving toward handle body (6110) to the closed configuration. Blocker (6154) is a protrusion extending from handle body (6110) at a transverse length that corresponds with a predetermined gap (6160) formed between an ultrasonic blade (6142) and a clamp arm (6144). With static spacer (6150) in the actuated position, clamp arm actuator (6130) is laterally offset from the longitudinal alignment of handle body (6110), as shown in FIGS. 46-47. In this instance, clamp arm actuator (6130) is configured to move towards handle body (6110) to the closed configuration without encountering blocker (6154), as seen in FIG. 45, thereby allowing ultrasonic blade (6142) and clamp arm (6144) to move to the closed position.

Clamp arm adjuster (6152) is further configured to pivot clamp arm actuator (6130) from the second position to the first position, back in lateral alignment with handle body (6110). As static spacer (6150) is transitioned from the unactuated position to the actuated position, clamp arm actuator (6130) is configured to laterally pivot relative to coupling portion (6125) to the first position with clamp arm actuator (6130) in alignment with handle body (6110) and blocker (6154). With static spacer (6150) in the actuated position, blocker (6154) is configured to maintain end effector (6140) at an intermediate position with predetermined gap (6160) formed between ultrasonic blade (6152) and clamp arm (6144).

FIG. 48 shows an exemplary alternative static spacer (6250) positioned along a handle body (6210) of a fourteenth exemplary surgical instrument (6200). Static spacer (6250) includes a clamp arm adjuster (6252) and a blocker (6254). Static spacer (6250) is configured to be in an initial unactuated position, as seen in FIGS. 48-50. In this instance, blocker (6254) is positioned along handle body (6210) and is configured to fixedly protrude from handle body (6210) in the transverse direction towards clamp arm actuator (6230). Blocker (6254) includes a gap (6256) centrally positioned in blocker (6254) and is configured to receive clamp arm actuator (6230) when moved towards handle body (6210). Similar to clamp arm adjuster (6152), clamp arm adjuster (6252) is integral and unitary with clamp arm actuator (6230) and is configured to selectively manipulate clamp arm actuator (6230) towards handle body (6210). In this instance, clamp arm actuator (6230) is moved towards handle body (6210) to the closed configuration and received within gap (6256) without encountering blocker (6254), as seen in FIGS. 153A-153B. Clamp arm adjuster (6230) is further configured to pivot clamp arm actuator (6230) in a lateral direction (a, b) relative to handle body (6210), as seen in FIG. 54A. With static spacer (6250) in the actuated position, clamp arm adjuster (6252) is configured to laterally pivot clamp arm actuator (6230) about a coupling portion (6225), relative to handle body (6210), to engage blocker (6254), as seen in FIG. 54A. In this instance, blocker (6254) is configured to inhibit clamp arm actuator (6230) moving relative to handle body (6210) to the closed configuration as shown in FIG. 53.

Figure 51A:
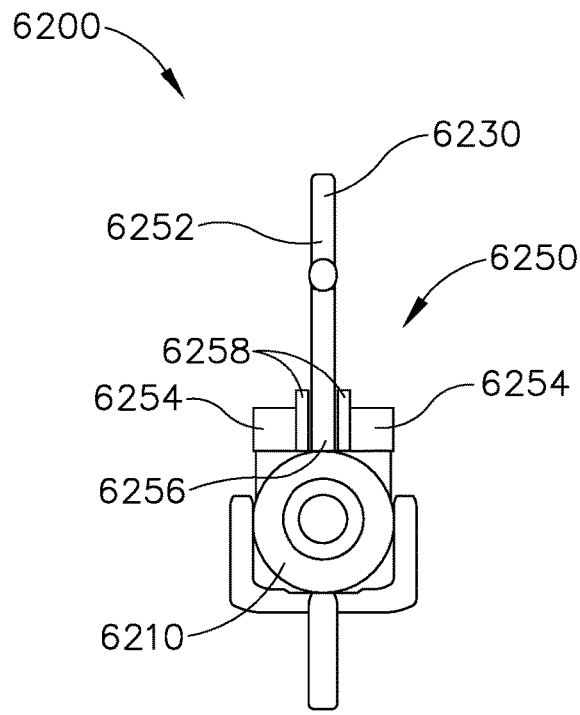
FIG. 51A depicts a rear elevational view of the surgical instrument of FIG. 48, with the static spacer in the unactuated position and the clamp arm actuator aligned with a gap of the blocker, with the gap including interior sidewalls.
Figure 51B:
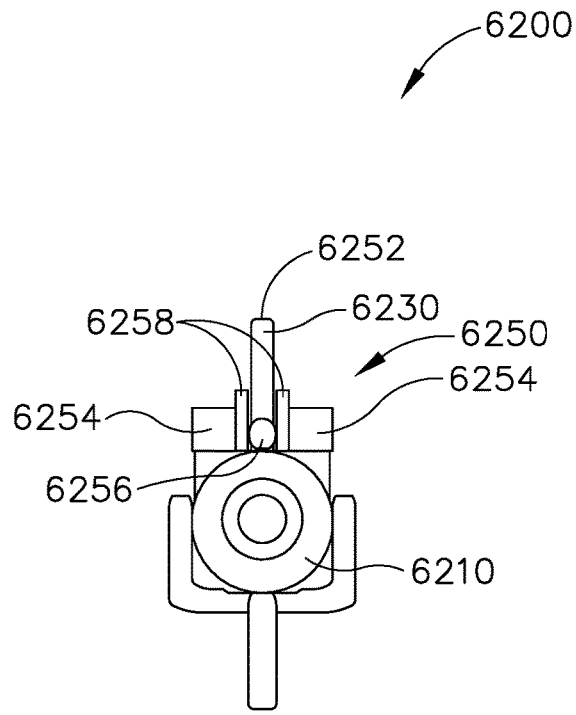
FIG. 51B depicts a rear elevational view of the surgical instrument of FIG. 48, with the static spacer in the unactuated position and the clamp arm actuator received within the gap of the blocker and between the interior sidewalls.
Figure 52:
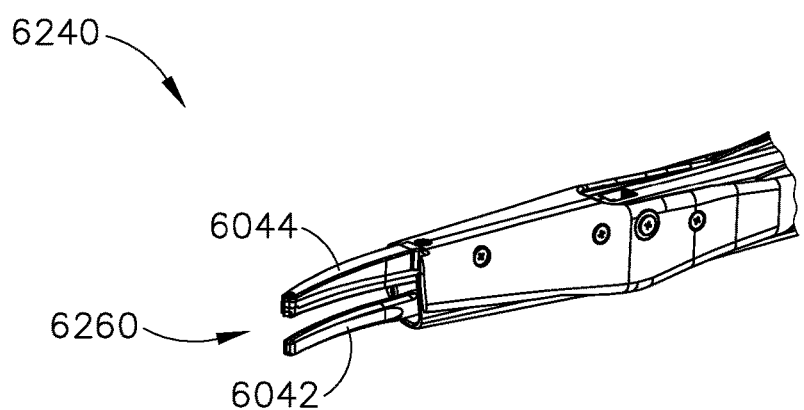
FIG. 52 depicts a partial perspective view of the surgical instrument of FIG. 48, with the end effector in an intermediate position.
Figure 53:
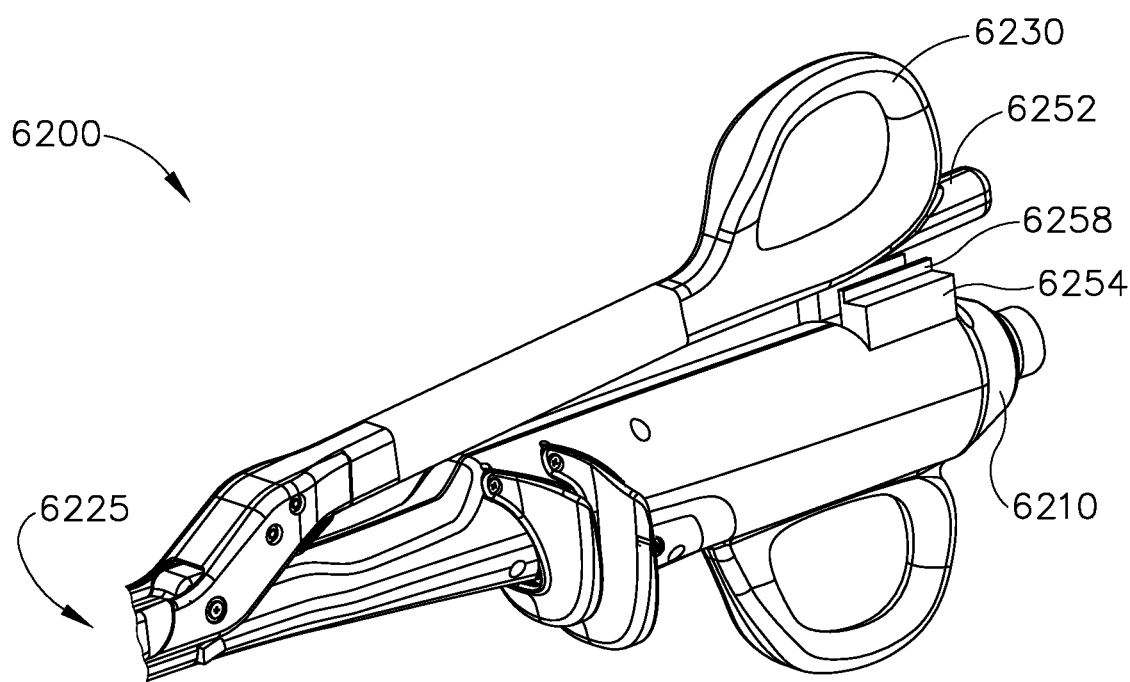
FIG. 53 depicts a partial perspective view of the surgical instrument of FIG. 48, with the static spacer in an actuated position and the clamp arm actuator engaged with the blocker.
Figure 54A:
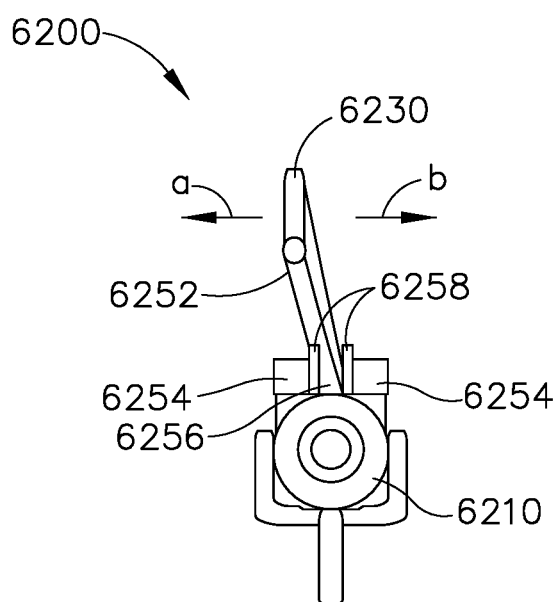
FIG. 54A depicts a rear elevational view of the surgical instrument of FIG. 48, with the static spacer in the actuated position and the clamp arm actuator pivoted laterally to a first side.
Figure 54B:
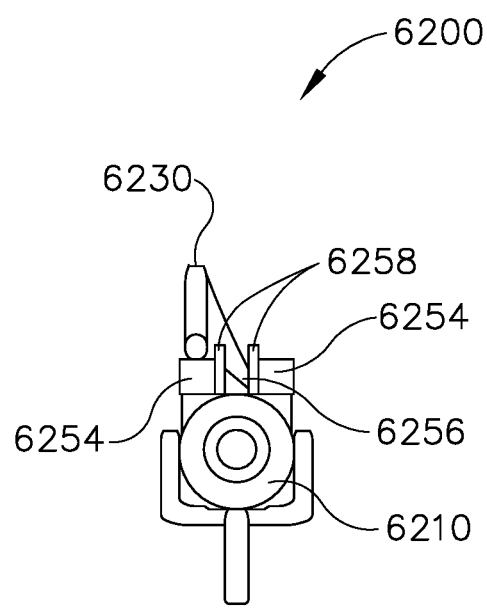
FIG. 54B depicts a rear elevational view of the surgical instrument of FIG. 48, with the static spacer in the actuated position and the clamp arm actuator engaged against the blocker, with the interior sidewall inhibiting the gap from receiving the clamp arm actuator.
Figure 55A:
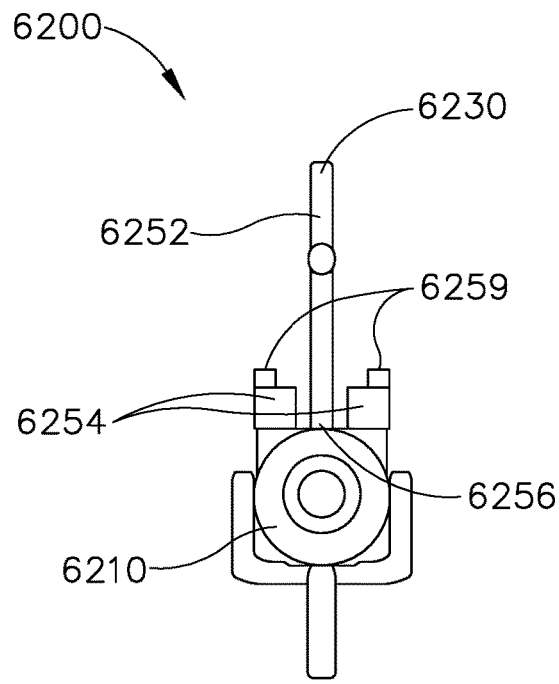
FIG. 55A depicts a rear elevational view of the surgical instrument of FIG. 48 including another exemplary alternative static spacer, with the static spacer in the unactuated position and the clamp arm actuator aligned with a gap of the blocker, with the gap including exterior sidewalls.
Figure 55B:
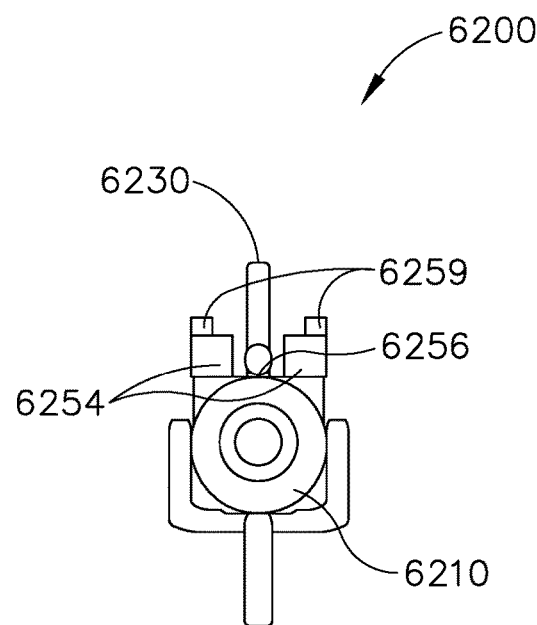
FIG. 55B depicts a rear elevational view of the surgical instrument of FIG. 55A, with the static spacer in the unactuated position and the clamp arm actuator received within the gap of the blocker and between the exterior sidewalls.
Figure 55C:
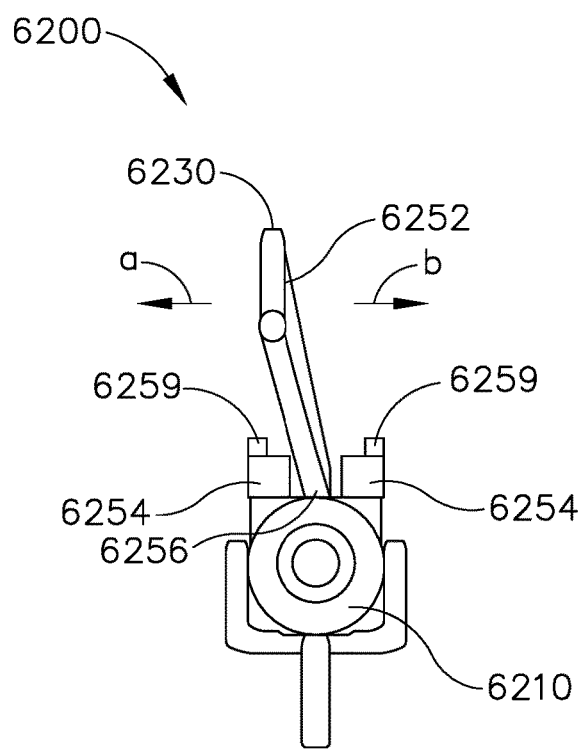
FIG. 55C depicts a rear elevational view of the surgical instrument of FIG. 55A, with the static spacer in the actuated position and the clamp arm actuator pivoted laterally to a second side.
Figure 55D:
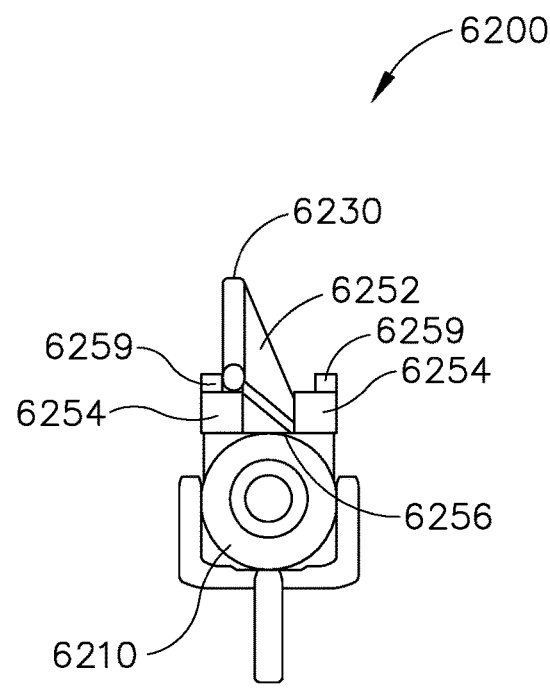
FIG. 55D depicts a rear elevational view of the surgical instrument of FIG. 55A, with the static spacer in the actuated position and the clamp arm actuator engaged against the blocker, with the exterior sidewall inhibiting the clamp arm actuator from disengaging with the blocker.

In the present example, as seen in FIG. 53, clamp arm adjuster (6252) is configured to laterally pivot clamp arm actuator (6230) about coupling portion (6225) from a first position, with clamp arm actuator (6230) in longitudinal alignment with gap (6256), to a second position with clamp arm actuator (6230) laterally offset from gap (6256). In this instance, clamp arm adjuster (6252) is unitary with clamp arm actuator (6230). With static spacer (6250) in the actuated position, clamp arm actuator (6230) is in longitudinal alignment with gap (6256), as seen in FIG. 50. In this instance, clamp arm actuator (6230) is configured to move towards handle body (6210) to the closed configuration without encountering blocker (6254), as seen in FIGS. 51A-51B, thereby allowing ultrasonic blade (6242) and clamp arm (6244) to move to the closed position as shown in FIG. 15l. With static spacer (6250) in the actuated position, clamp arm actuator (6230) is laterally offset from the longitudinal alignment of gap (6256), as shown in FIGS. 54A-54B. In this instance, blocker (6254) is configured to inhibit clamp arm actuator (6230) from moving toward handle body (6210) to the closed configuration. Blocker (6254) is a protrusion extending from handle body (6210) at a transverse length that corresponds with a predetermined gap (6260) formed between an ultrasonic blade (6242) and a clamp arm (6244), as seen in FIG. 52. Blocker (6254) further includes at least one sidewall (6258) positioned adjacent gap (6256). As seen in FIGS. 54A-54B, sidewalls (6258) are configured to hold clamp arm actuator (6230) against blocker (6254) to maintain static spacer (6250) in the actuated position. In this instance, blocker (6254) includes interior sidewalls (6258) along gap (6256), as seen in FIGS. 156A-156B. In some other versions, blocker (6254) includes exterior sidewalls (6259) along the outer perimeter of blocker (6254), as seen in FIGS. 55A-55D. It will be apparent to those of ordinary skill in the art in view of the teachings herein that interior sidewalls (6258) and exterior sidewalls (6259) are similarly sized and configured to maintain static spacer (6250) in the actuated position.

Clamp arm adjuster (6252) is further configured to pivot clamp arm actuator (6230) from the second position to the first position, back in lateral alignment with gap (6256). As static spacer (6250) is transitioned from the unactuated position to the actuated position, clamp arm actuator (6230) is configured to laterally pivot relative to coupling portion (6225) to the first position with clamp arm actuator (6230) in alignment with handle body (6210) and gap (6256). With static spacer (6250) in the actuated position, clamp arm actuator (6230) is configured to move relative to handle body (6210) to the closed configuration without encountering blocker (6254) to thereby move ultrasonic blade (6252) and clamp arm (6244) to the closed position.

Figure 56A:
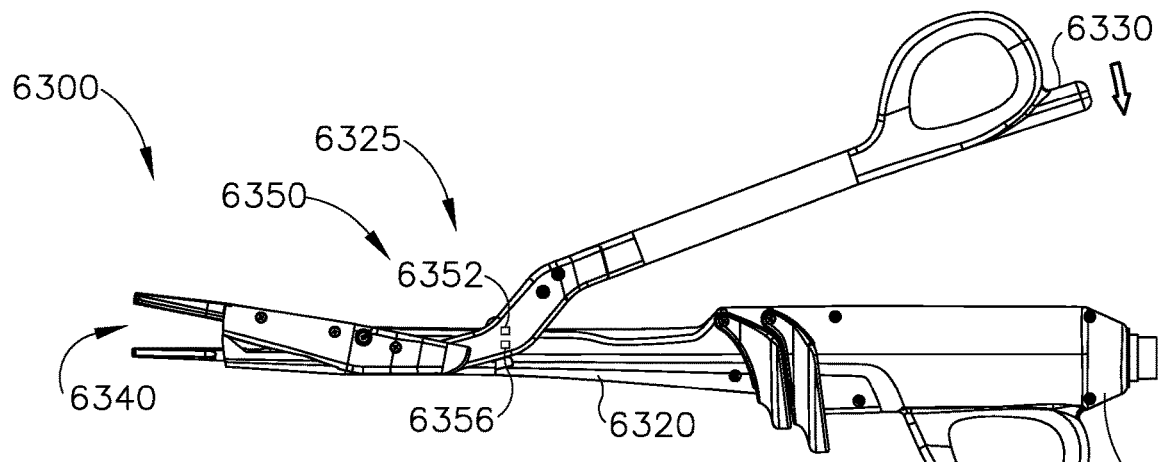
FIG. 56A depicts a side elevational view of a fifteenth exemplary surgical instrument including an exemplary magnetic urging mechanism and an end effector, with the magnetic urging mechanism outside a magnetic field and the end effector in an open position.
Figure 56B:
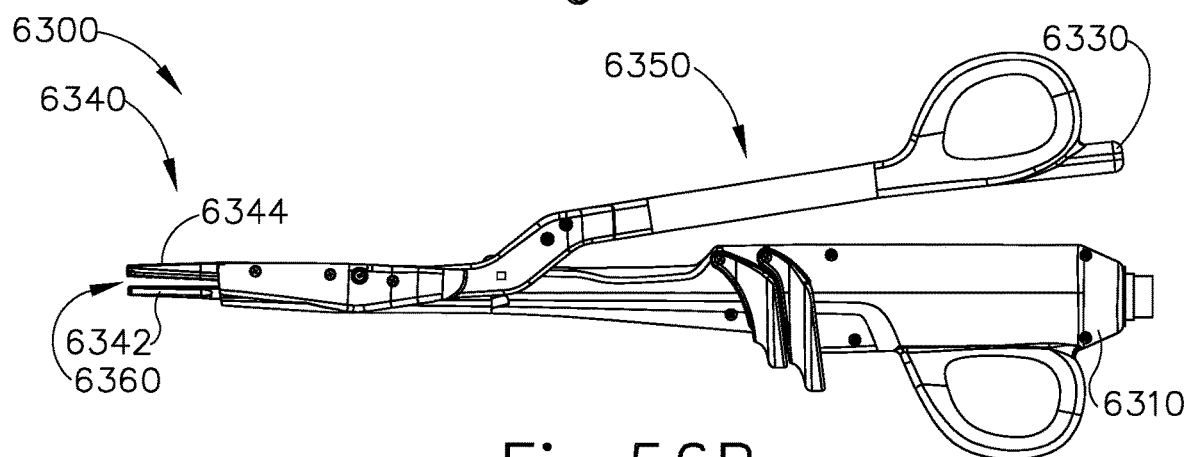
FIG. 56B depicts a side elevational view of the surgical instrument of FIG. 56A, with the magnetic urging mechanism within the magnetic field and the end effector in an intermediate position.
Figure 56C:
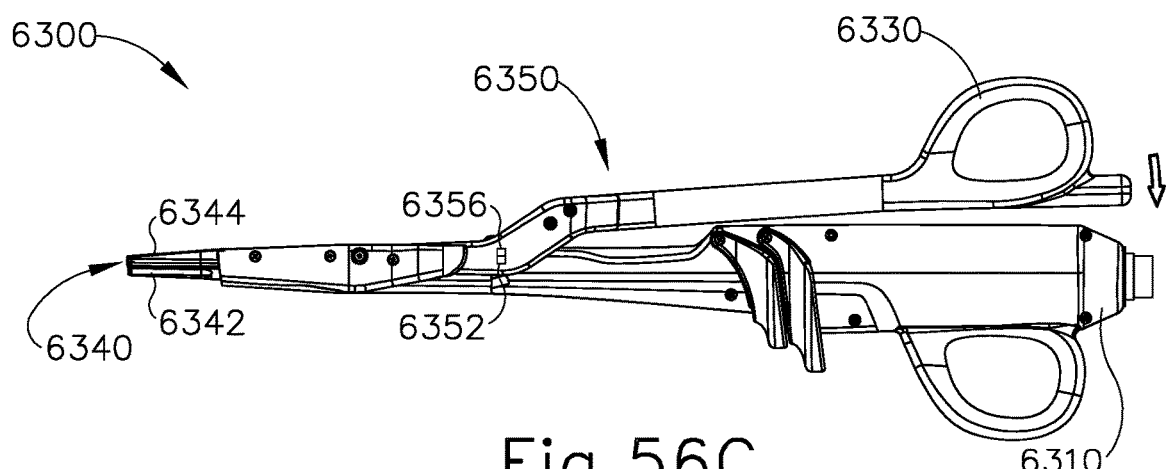
FIG. 56C depicts a side elevational view of the surgical instrument of FIG. 56A, with the magnetic urging mechanism outside the magnetic field and the end effector in a closed position.

B. Exemplary Surgical Instrument with Urging Mechanism i. Magnetic Urging Mechanism FIGS. 56A-56C show an exemplary magnetic urging mechanism (6350) positioned along a shaft assembly (6320) and a clamp arm actuator (6330) of a fifteenth exemplary surgical instrument (6300). Magnetic urging mechanism (6350) includes a first magnet (6352) and a second magnet (6356). First magnet (6352) is within clamp arm actuator (6330) proximal to a coupling portion (6325) and is configured to have a first positive pole (6353) and a first negative pole (6354). Second magnet (6356) is within shaft assembly (6320) proximal to coupling portion (6325) and is configured to have a second positive pole (6357) and a second negative pole (6358). As it will be apparent to those of ordinary skill in the art, a positive pole is configured to have an electric charge, or polarity, opposite to a negative pole. First magnet (6352) is configured to exhibit a first magnetic field (not shown) and second magnet (6356) is configured to exhibit a second magnetic field (not shown). With clamp arm actuator (6330) in an open configuration relative to handle body (6310), first magnetic field of first magnet (6352) does not overlap with second magnetic field of second magnet (6356). As seen in FIG. 56A, first negative pole (6354) is positioned within clamp arm actuator (6330) proximal to second positive pole (6357) in shaft assembly (6320). In this instance, first negative pole (6354) and second positive pole (6357) are configured to establish a mutual force of attraction, or magnetism, between clamp arm actuator (6330) and shaft assembly (6320). Accordingly, as further seen in FIG. 56A, first positive pole (6353) is positioned within clamp arm actuator (6330) distal to second negative pole (6358) in shaft assembly (6320).

First magnet (6352) and second magnet (6356) are configured to be positioned within clamp arm actuator (6330) and shaft assembly (6320), respectively, to magnetically attract to each other as clamp arm actuator (6330) is moved towards handle body (6310). Magnets (6352, 6356) are further configured to laterally align and magnetically attract to each other with a predetermined gap (6360) formed between an ultrasonic blade (6342) and a clamp arm (6344) of an end effector (6340) of surgical instrument (6300). In other words, first magnet (6352) and second magnet (6356) are configured to be in lateral alignment at a point corresponding to predetermined gap (6360) being formed at end effector (6340). Although not shown, it should be understood that additional magnets (6352, 6356) may be included in surgical instrument (6300) than that depicted. The geometry of magnets (6352, 6356) may be selectively sized and shaped to govern the respective magnitudes, strengths, and magnetic field size of magnets (6352, 6356).

In the present example, as seen in FIG. 56A, first magnet (6352) is configured to enter second magnetic field of second magnet (6356) with clamp arm actuator (6330) and handle body (6310) moved towards the closed configuration. Similarly, in this instance, second magnet (6356) is configured to enter first magnetic field of first magnet (6352). As clamp arm actuator (6330) is moved towards handle body (6310), magnetic urging mechanism (6350) is configured to magnetically urge clamp arm actuator (6330) towards handle body (6310) through the magnetic attraction of first negative pole (6353) and second positive pole (6357). In the present example, magnetic urging mechanism (6350) urges clamp arm actuator (6330) and handle body (6310) until magnets (6352, 6356) are magnetically coupled with magnets (6352, 6356) in lateral alignment with each other, as seen in FIG. 56B. With magnets (6352, 6356) magnetically coupled, ultrasonic blade (6342) and clamp arm (6344) are configured to be in an intermediate position with predetermined gap (6360) formed at end effector (6340), as seen in FIG. 56B. The magnetic coupling of magnets (6352, 6356) is configured to provide a tactile feedback to the operator that predetermined gap (6360) is formed at end effector (6340). However, the magnetism created by magnetic urging mechanism (6350) may be with the application of excessive force on clamp arm actuator (6330) towards handle body (6310) to thereby overcome the magnetic coupling of magnets (6352, 6356).

ii. Biasing Urging Mechanism

FIGS. 57-58 respectively show exemplary biasing urging mechanisms (6450) positioned along a sixteenth exemplary surgical instrument (6400). Biasing urging mechanism (6450) includes a spring (6452) configured to generate resistance against clamp arm actuator (6430) moving towards handle body (6410). Biasing urging mechanism (6450) is further configured to provide a tactile feedback that a predetermined gap (6460) is formed between an ultrasonic blade (6442) and a clamp arm (6444) of an end effector (6440). The resistance created by biasing urging mechanism (6450) as clamp arm actuator (6430) moves relative to handle body (6410) is configured to assist an operator in maintaining predetermined gap (6460) at end effector (6440). However, the resistance generated by biasing urging mechanism (6450) is further configured to be overcome when an excessive force is exerted on clamp arm actuator (6430) towards handle body (6310) to exceed the resistance created by spring (6452). In this instance, end effector (6440) of surgical instrument (6400) is configured to close ultrasonic blade (6442) and clamp arm (6444) to the closed position without interruption from biasing urging mechanism (6450).

It will be apparent to those of ordinary skill in the art that biasing urging mechanism (6450) may take varying shapes and sizes that may be suitable in generating resistance against clamp arm actuator (6430) moving towards handle body (6410) to the closed configuration. In the present example, as seen in FIG. 57, spring (6452) is a leaf spring fixedly attached to shaft assembly (6420) at a first end (6453) and to clamp arm actuator (6430) at a second end (6454). In this instance, clamp arm actuator (6430) is configured to move towards handle body (6410) to compress spring (6452) by urging second end (6454) towards first end (6453). Spring (6452) is configured to create resistance between shaft assembly (6420) and clamp arm actuator (6430) with the compression of ends (6453, 6454).

In other versions, as seen in FIG. 58, another biasing urging mechanism (6550) has a spring (6552), which is a torsion spring positioned along a coupling portion (6525) of surgical instrument (6400). In this instance, first end (6553) is fixedly attached to a first pin (6570) and second end (6554) is fixedly attached to a second pin (6572). In this instance, clamp arm actuator (6530) is configured to move towards handle body (6510) to compress spring (6552) by urging first end (6553) towards second end (6554). Spring (6552) is configured to create resistance between first pin (6570) and second pin (6572) at end effector (6540) with the compression of ends (6553, 6554). Although not shown, it should be understood that leaf spring (6452) and torsion spring (6552) may be separately or mutually included on surgical instrument (6400).

In some other versions, as seen in FIG. 59, spring (6652) is a compression spring positioned proximal to a coupling portion (6625) of a seventeenth exemplary surgical instrument (6600). Spring (6652) includes a first end (6653) fixedly attached to shaft assembly (6620) and a second end (6654) fixedly attached to clamp arm actuator (6630). In this instance, clamp arm actuator (6630) is configured to move towards handle body (6610) to compress spring (6652) by urging second end (6654) towards first end (6653). Spring (6652) is configured to create resistance between shaft assembly (6620) and clamp arm actuator (6630) with the compression of ends (6653, 6654).

By default, springs (6452, 6552, 6652) are configured to fully extend clamp arm actuator (6430, 6530, 6630) away from handle body (6410, 6510, 6610) to the greatest extent with clamp arm actuator (6430, 6530, 6630) and handle body (6410, 6510, 6610) in the open configuration. Springs (6452, 6552, 6652) are further configured to provide tactile feedback to an operator as clamp arm actuator (6430, 6530, 6630) moves towards handle body (6410, 6510, 6610) to indicate a predetermined gap (6460, 6560, 6660) is formed between ultrasonic blade (6442, 6542, 6642) and clamp arm (6444, 6544, 6644) with end effector (6440, 6540, 6640) in the intermediate position.

iii. Anchored Urging Mechanism

Figure 60A:
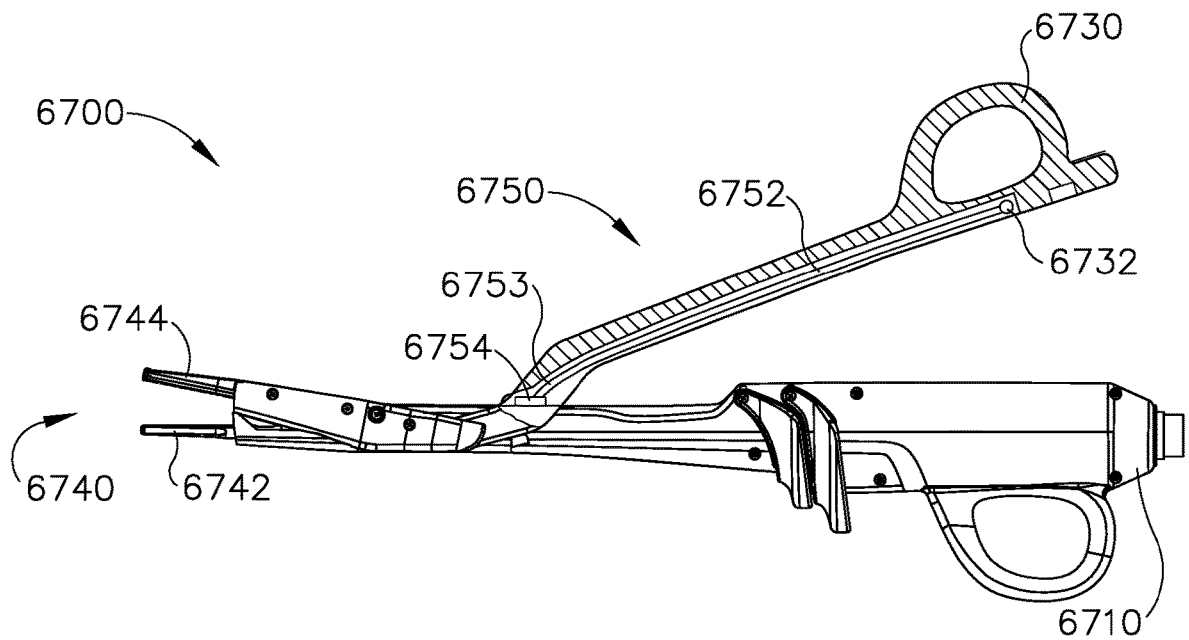
FIG. 60A depicts a side elevational view of an eighteenth exemplary surgical instrument including an exemplary anchored urging mechanism contained within a clamp arm actuator and an end effector, with an anchor between the anchored urging mechanism and a shaft assembly, with the anchored urging mechanism in an unactuated position and the end effector in an open position.
Figure 60B:
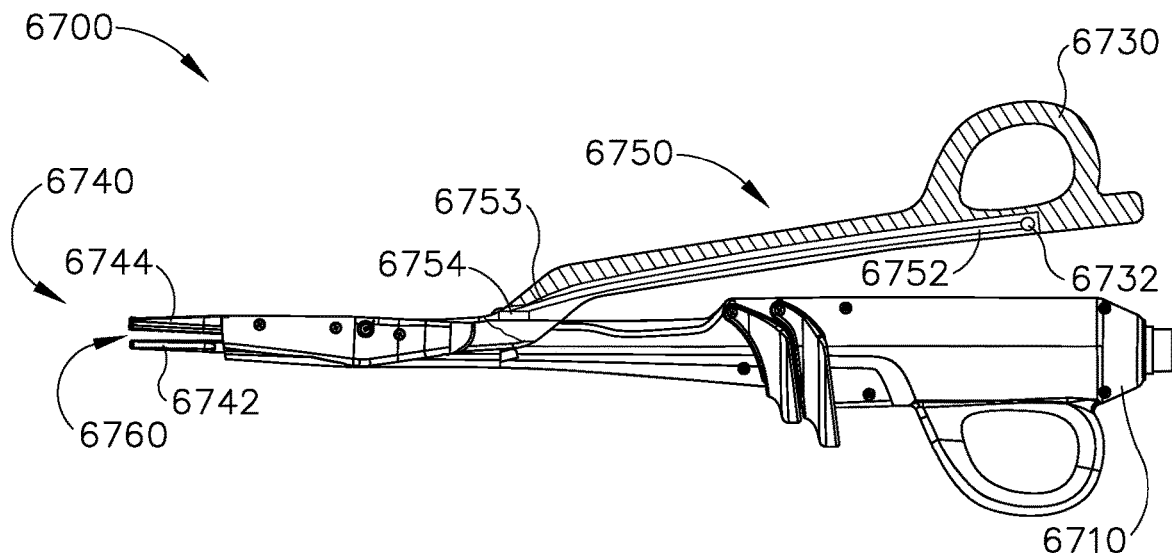
FIG. 60B depicts a side elevational view of the surgical instrument of FIG. 60A, with the anchored urging mechanism in an actuated position and a blocker engaging the anchor, with the end effector in an intermediate position.

FIGS. 60A-60B show an exemplary anchored urging mechanism (6750) positioned within a channel (6732) of a clamp arm actuator (6730) of an eighteenth exemplary surgical instrument (6700). Anchored urging mechanism (6750) includes a spring (6752) configured to generate resistance against clamp arm actuator (6730) moving towards handle body (6710). Anchored urging mechanism (6750) is further configured to provide a tactile feedback that a predetermined gap (6760) is formed between an ultrasonic blade (6742) and a clamp arm (6744) of an end effector (6740). The resistance created by anchored urging mechanism (6750) as clamp arm actuator (6730) moves towards handle body (6710) is configured to assist an operator in maintaining predetermined gap (6760) at end effector (6740). However, the resistance generated by anchored urging mechanism (6750) is further configured to be overcome when an excessive force is exerted on clamp arm actuator (6730) towards handle body (6710) to exceed the resistance created by spring (6752). In this instance, end effector (6740) of surgical instrument (6700) is configured to close ultrasonic blade (6742) and clamp arm (6744) to the closed position without interruption from anchored urging mechanism (6750).

Figure 61A:
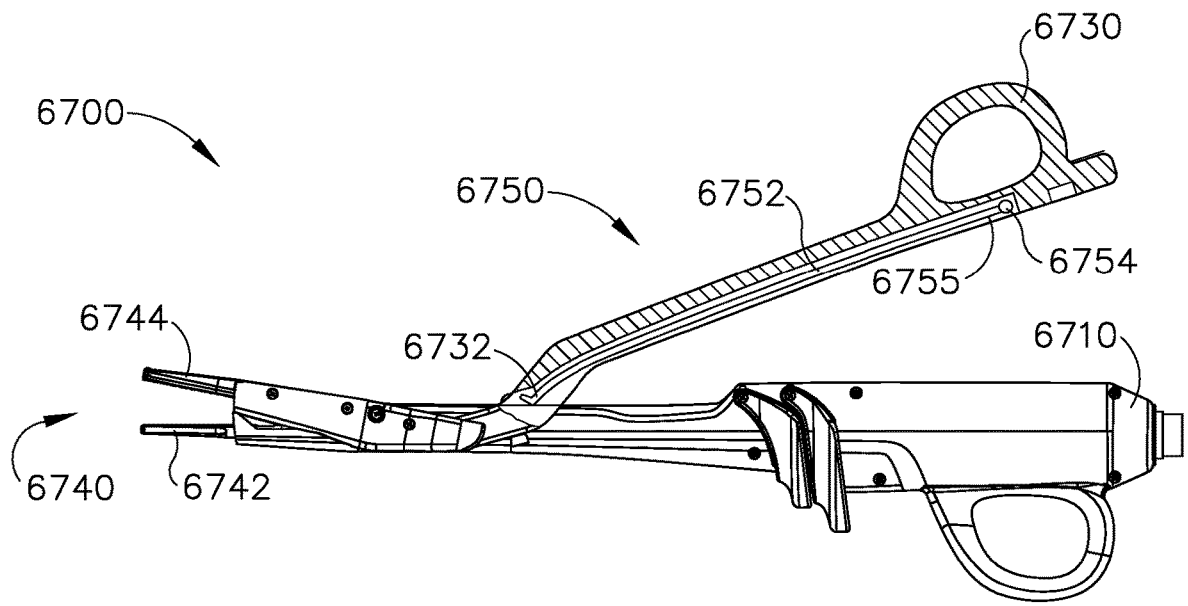
FIG. 61A depicts a side elevational view of the surgical instrument of FIG. 60A, with the anchor between the anchored urging mechanism and the shaft assembly, with the anchored urging mechanism in the unactuated position and the end effector in an open position.
Figure 61B:
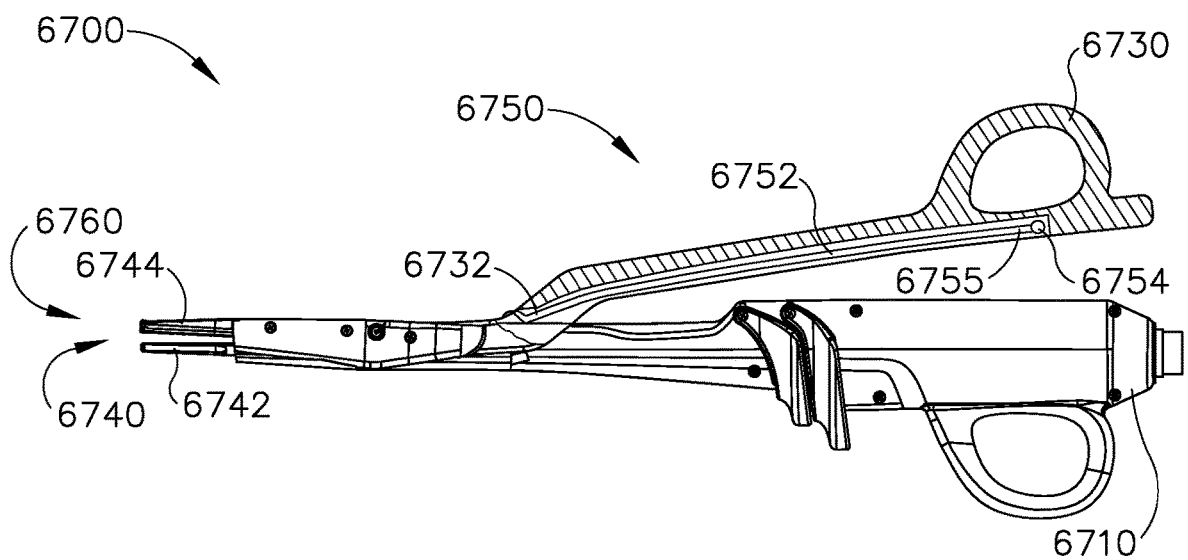
FIG. 61B depicts a side elevational view of the surgical instrument of FIG. 60A, with the anchored urging mechanism in an actuated position and the blocker engaging the shaft assembly, with the end effector in an intermediate position.

In the present example, as seen in FIG. 60A, spring (6752) of anchored urging mechanism (6750) is within channel (6732) of clamp arm actuator (6730). Channel (6732) has a longitudinal length greater than spring (6752) such that spring (6752) is configured to slidably translate within channel (6732) with clamp arm actuator (6730) moving towards or away from handle body (6710). Spring (6752) engages an anchor (6754) at a distal end (6753) of spring (6752) such that spring (6752) is configured to bias against anchor (6754) with clamp arm actuator (6730) moving relative to handle body (6710) to the closed configuration. In some other versions, as seen in FIGS. 61A-61B, anchor (6754) is at a proximal end (6755) of spring (6752) such that spring (6752) is configured to bias against channel (6732) at distal end (6753). Clamp arm actuator (6730) is configured to move towards handle body (6710) and compresses spring (6752) within channel (6732) at distal end (6753) to thereby generate resistance against clamp arm actuator (6730) and handle body (6710) moving to the closed configuration. Spring (6752) is further configured to provide a tactile feedback in forming predetermined gap (6760) between ultrasonic blade (6742) and clamp arm (6744) of end effector (6740).

iv. Dual Urging Mechanism

FIG. 62A shows an exemplary dual urging mechanism (6850) positioned along a nineteenth exemplary surgical instrument (6800). Dual urging mechanism (6850) includes an opening spring (6852) and a closing spring (6856). Opening spring (6852) is fixedly attached at a proximal end (6853) to handle body (6810) and at a distal end (6854) to clamp arm actuator (6830), proximal to a coupling portion (6825). Opening spring (6852) extends between handle body (6810) and clamp arm actuator (6830) in parallel alignment with a longitudinal axis (6822) of shaft assembly (6820). Closing spring (6856) is fixedly attached at a first end (6857) to handle body (6810) and at a second end (6858) to clamp arm actuator (6830). Closing spring (6856) extends between handle body (6810) and clamp arm actuator (6830) in perpendicular alignment with longitudinal axis (6822) of shaft assembly (6820).

Opening spring (6852) is configured to urge clamp arm actuator (6830) away from handle body (6810) to thereby create an opening resistance against clamp arm actuator (6830) moving towards handle body (6810) to the closed configuration. Closing spring (6856) is configured to urge clamp arm actuator (6830) towards handle body (6810) to thereby create a closing resistance against clamp arm actuator (6830) moving away from handle body (6810) to the open configuration. The opening resistance created by opening spring (6852), to urge clamp arm actuator (6830) away from handle body (6810), is greater than the simultaneous, closing resistance created by closing spring (6856) to urge clamp arm actuator (6830) towards handle body (6810), seen in FIGS. 63-64. Through the opposing forces created by springs (6852, 6856), dual urging mechanism (6850) is configured to assist a predetermined gap (6860) to be formed between an ultrasonic blade (6842) and a clamp arm (6844) of an end effector (6840).

Figure 65:
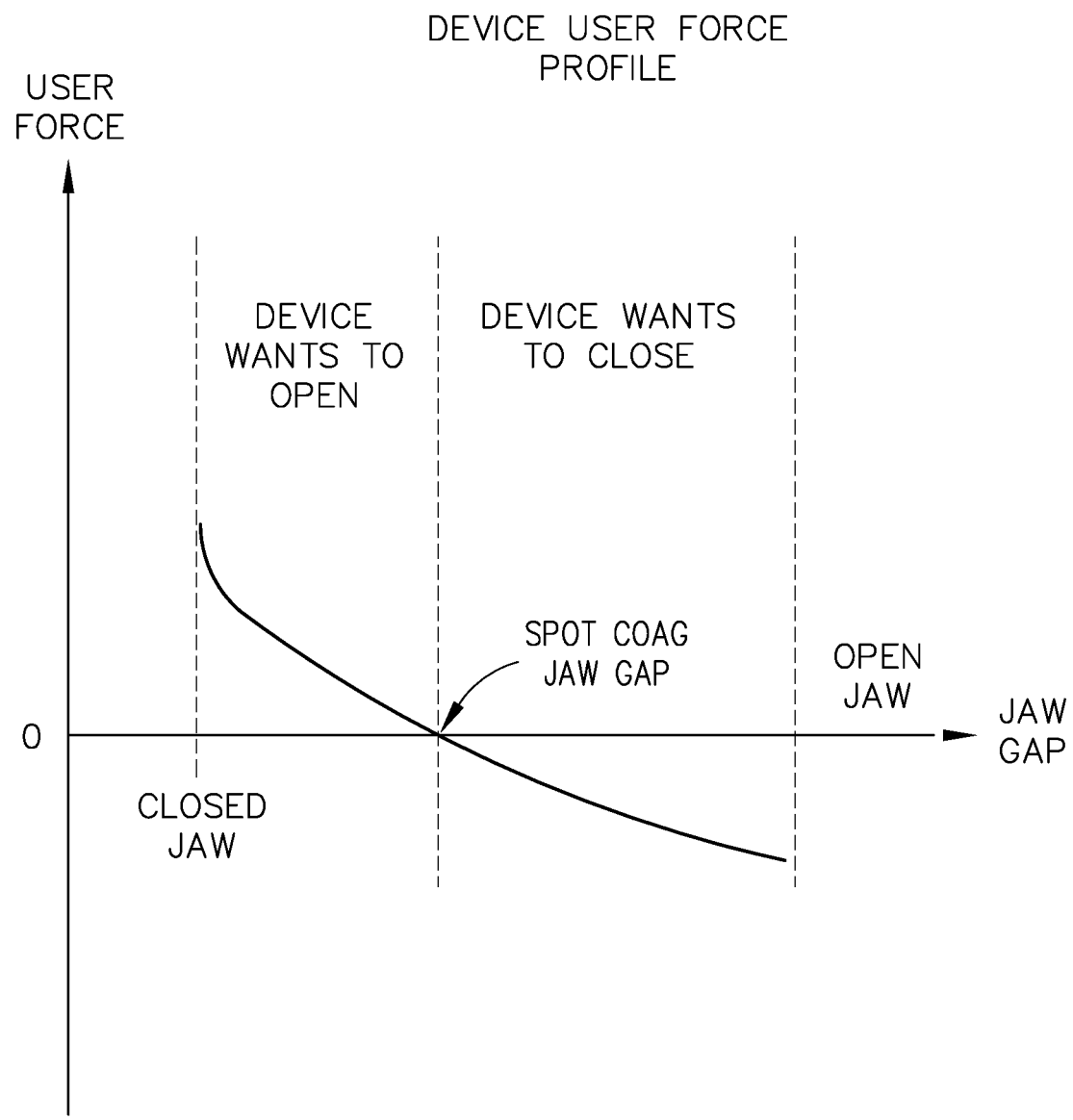
FIG. 65 is a diagrammatical view of the relationship between both springs of the dual urging mechanism of FIG. 60A and the end effector.

In the present example, as seen in FIG. 62B, clamp arm actuator (6830) is configured to move towards handle body (6810) to thereby overcome the opening resistance created by opening spring (6852). In this instance, as clamp arm actuator (6830) is moved relative to handle body (6810), closing spring (6856) is configured to guide ultrasonic blade (6842) and clamp arm (6844) to an intermediate position to thereby form predetermined gap (6860) at end effector (6840). Dual urging mechanism (6850) is further configured to assist an operator in maintaining predetermined gap (6860) at end effector (6840). However, dual urging mechanism (6850) is configured to be overcome when an excessive force exerted on clamp arm actuator (6830) towards handle body (6810) exceeds the corresponding biases of springs (6852, 6856), as illustrated in FIGS. 63-65. In this instance, as seen in FIG. 62C, end effector (6840) of surgical instrument (6800) is configured to close ultrasonic blade (6842) and clamp arm (6844) to the closed position.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector, including: (i) an ultrasonic blade, and (ii) a clamp arm configured to move relative to the ultrasonic blade from an opened position toward an intermediate position and a closed position, wherein the ultrasonic blade and the clamp arm are configured to receive tissue in the opened position, wherein the clamp arm is configured to clamp tissue against the ultrasonic blade in the closed position, and wherein the clamp arm is offset from the ultrasonic blade to define a predetermined gap in the intermediate position between the opened position and the closed position; (b) a shaft assembly projecting proximally from the end effector and including an acoustic waveguide operatively connected to the ultrasonic blade, wherein the acoustic waveguide is configured to connect to an ultrasonic transducer; (c) a body projecting proximally from the shaft assembly; (d) a clamp arm actuator operatively connected to the clamp arm and configured to selectively move relative to the body from an opened configuration to a closed configuration to thereby direct the clamp arm respectively from the opened position toward the intermediate position and the closed position; (e) a spacer operatively connected to the clamp arm and configured to inhibit movement of the clamp arm from the intermediate position toward the closed position for maintaining at least the predetermined gap between the clamp arm and the ultrasonic blade.

Example 2

The surgical instrument of Example 1, wherein the spacer includes an adjuster configured to be manipulated from an unactuated position to an actuated position, wherein the spacer further includes a blocker configured to inhibit movement of the clamp arm actuator towards the body with the spacer in the actuated position.

Example 3

The surgical instrument of Example 2, wherein the blocker is configured to distally translate along the shaft assembly to wedge against the clamp arm actuator with the adjuster actuated in a distal direction.

Example 4

The surgical instrument of Example 3, wherein the clamp arm actuator is configured to slidably receive the blocker such that the blocker is configured to impede movement of the clamp arm actuator in the closed configuration with the spacer in the actuated position.

Example 5

The surgical instrument of Example 3, wherein the blocker is connected to an extension, wherein the extension is configured to position the blocker between the clamp arm actuator and the shaft assembly to impede the movement of the clamp arm actuator in the closed configuration with the spacer in the actuated position.

Example 6

The surgical instrument of Example 3, wherein the blocker is configured to distally translate along the end effector to wedge the blocker against the clamp arm with the adjuster actuated in the distal direction.

Example 7

The surgical instrument of Example 2, wherein the adjuster is configured to urge the blocker through the shaft assembly and toward the clamp arm actuator with the spacer in the actuated position, wherein the adjuster is configured to retract the blocker into the shaft assembly and away from the clamp arm actuator with the spacer in the unactuated position.

Example 8

The surgical instrument of Example 2, wherein the adjuster includes a gap configured to receive the blocker with the spacer in the unactuated position.

Example 9

The surgical instrument of claim 8, wherein the adjuster is laterally manipulatable in relation to the shaft assembly to transversely extend the blocker in relation to the shaft assembly.

Example 10

The surgical instrument of Example 2, wherein the spacer is connected to the shaft assembly and includes a rotatable knob with a varying diameter, wherein the blocker is movably positioned along the rotatable knob, wherein the adjuster is configured to rotate the rotatable knob such that the blocker movably extends along the varying diameter with the spacer in the actuated position.

Example 11

The surgical instrument of Example 2, wherein the spacer is connected to the clamp arm actuator, wherein the adjuster is configured to pivot the blocker toward the body with the spacer in the actuated position.

Example 12

The surgical instrument of Example 2, wherein the spacer is connected to the clamp arm actuator, wherein the adjuster is configured to pivot the blocker to extend laterally in relation to the body with the spacer in the actuated position.

Example 13

The surgical instrument of Example 2, wherein the spacer includes an extension configured to slidably translate within the clamp arm actuator, wherein the blocker is pivotably connected to the extension such that the blocker engages the shaft assembly with the spacer in the actuated position.

Example 14

The surgical instrument of Example 13, wherein the adjuster is configured to distally translate the extension within the clamp arm actuator with the spacer in the actuated position and proximally translate the extension within the clamp arm actuator with the spacer in the unactuated position.

Example 15

The surgical instrument of Example 2, wherein the blocker is fixedly connected to the body, wherein the adjuster is configured to laterally pivot the clamp arm actuator relative to the blocker such that the clamp arm actuator is disengaged from the blocker in the closed configuration with the spacer in the unactuated position.

Example 16

The surgical instrument of Example 15, wherein the blocker includes a gap configured to receive the clamp arm actuator such that the gap receives the clamp arm actuator in the closed configuration with the spacer in the unactuated position.

Example 17

The surgical instrument of Example 15, wherein the blocker includes at least one sidewall configured to inhibit the clamp arm actuator from entering the gap in the closed configuration with the spacer in the actuated position.

Example 18

A surgical instrument, comprising: (a) an end effector, including: (i) an ultrasonic blade, and (ii) a clamp arm configured to move relative to the ultrasonic blade from an opened position toward an intermediate position and a closed position, wherein the ultrasonic blade and the clamp arm are configured to receive tissue in the opened position, wherein the clamp arm is configured to clamp tissue against the ultrasonic blade in the closed position, and wherein the clamp arm is offset from the ultrasonic blade to define a predetermined gap in the intermediate position between the opened position and the closed position; (b) a shaft assembly projecting proximally from the end effector and including an acoustic waveguide operatively connected to the ultrasonic blade, wherein the acoustic waveguide is configured to connect to an ultrasonic transducer; (c) a body projecting proximally from the shaft assembly; (d) a clamp arm actuator operatively connected to the clamp arm and configured to selectively move relative to the body from an opened configuration to a closed configuration to thereby direct the clamp arm respectively from the opened position toward the intermediate position and the closed position; (e) an urging mechanism operatively connected to the clamp arm and configured to provide tactile feedback when the clamp arm is in the intermediate position and a predetermined gap is formed between the clamp arm and the ultrasonic blade.

Example 19

The surgical instrument of Example 18, wherein the urging mechanism includes at least two magnets with opposing polarities such that the at least two magnets are configured to magnetically attract, wherein the at least two magnets are respectively contained in the clamp arm actuator and the shaft assembly such that the at least two magnets are configured to urge the clamp arm actuator and the shaft assembly together to form the at least predetermined gap.

Example 20

The surgical instrument of Example 18, wherein the urging mechanism comprises a biasing member configured to bias the clamp arm actuator relative to the body.

Example 21

The surgical instrument of Example 20, wherein the biasing member is operatively attached to the shaft assembly and the clamp arm actuator such that the biasing member is configured to bias the clamp arm actuator away from the body with the clamp arm actuator in the closed configuration.

Example 22

The surgical instrument of Example 21, wherein the biasing member comprises a leaf spring.

Example 23

The surgical instrument of Example 20, wherein the biasing member is operatively attached to the ultrasonic blade and the clamp arm such that the biasing member is configured to bias the ultrasonic blade away from the clamp arm with the clamp arm actuator in the closed configuration.

Example 24

The surgical instrument of Example 23, wherein the biasing member comprises a torsion spring.

Example 25

The surgical instrument of Example 20, wherein the biasing member is fixedly attached to the shaft assembly and the clamp arm actuator such that the biasing member is configured to bias the shaft assembly away from the clamp arm actuator with the clamp arm actuator in the closed configuration.

Example 26

The surgical instrument of Example 25, wherein the biasing member comprises a compression spring.

Example 27

The surgical instrument of Example 20, wherein the urging mechanism further includes an anchor, wherein the biasing member is configured to slidably translate within the clamp arm actuator to wedge against the anchor and bias the clamp arm actuator away from the body with the clamp arm actuator in the closed configuration.

Example 28

The surgical instrument of Example 27, wherein the anchor is positioned at a distal end of the biasing member.

Example 29

The surgical instrument of Example 27, wherein the anchor is positioned at a proximal end of the biasing member.

Example 30

The surgical instrument of Example 18, wherein the urging mechanism includes a first biasing member and a second biasing member, wherein the first biasing member is attached to the shaft assembly and the clamp arm actuator, wherein the second biasing member is attached to the body and the clamp arm actuator.

Example 31

The surgical instrument of Example 30, wherein the first biasing member has a first resiliency configured to bias the clamp arm actuator away from the shaft assembly, wherein the second biasing member has a second resiliency configured to bias the clamp arm actuator towards the body with a second resiliency, wherein the first resiliency is greater than the second resiliency.

Example 32

A surgical instrument comprising: (a) an end effector, including: (i) an ultrasonic blade, and (ii) a clamp arm configured to move relative to the ultrasonic blade from an opened position toward an intermediate position and a closed position, wherein the ultrasonic blade and the clamp arm are configured to receive tissue in the opened position, wherein the clamp arm is configured to clamp tissue against the ultrasonic blade in the closed position, and wherein the clamp arm is offset from the ultrasonic blade to define a predetermined gap in the intermediate position between the opened position and the closed position; (b) a shaft assembly projecting proximally from the end effector and including an acoustic waveguide operatively connected to the ultrasonic blade, wherein the acoustic waveguide is configured to connect to an ultrasonic transducer; (c) a body projecting proximally from the shaft assembly; (d) a clamp arm actuator operatively connected to the clamp arm and configured to selectively move relative to the body from an opened configuration to a closed configuration to thereby direct the clamp arm respectively from the opened position toward the intermediate position and the closed position; and (e) a first biasing member and a second biasing member, wherein the first biasing member is attached to the shaft assembly and the clamp arm actuator, wherein the second biasing member is attached to the body and the clamp arm actuator, and wherein the first and second biasing members are configured to provide tactile feedback when the clamp arm is in the intermediate position and the predetermined gap is formed between the clamp arm and the ultrasonic blade.

V. Miscellaneous

While various examples herein describe two or more modular components being releasably coupled together, it should be understood that some variations may eliminate such modularity and releasable couplings. For instance, some versions of instrument (10) may provide first modular assembly (100) and second modular assembly (200) as a single combined unit that does not permit second modular assembly (200) to be removed form first modular assembly (100). In some such versions, coupling member (300) would either me omitted (with some other feature being used to provide permanent coupling between first modular assembly (100) and second modular assembly (200)); or coupling member (300) may be modified such that coupling member (300) may not be manipulated to decouple second modular assembly (200) from first modular assembly (100). Similarly, some versions of instrument (301) may prevent clamp arm assembly (400) from being removed from shaft assembly (330). For instance, latch member (412) may be omitted and clamp arm assembly (400) may be permanently coupled with shaft assembly (330).

It should be understood that the various teachings herein may be readily combined with the various teachings of U.S. Pub. No. 2017/0105754, entitled "Surgical Instrument with Dual Mode End Effector and Side-Loaded Clamp Arm Assembly," published on Apr. 20, 2017, issued as U.S. Pat. No. 11,045,275 on Jun. 29, 2021, the disclosure of which is incorporated by reference herein. Various suitable ways in which the teachings herein may be combined with the teachings of U.S. Pub. No. 2017/0105754, issued as U.S. Pat. No. 11,045,275 on Jun. 29, 2021, will be apparent to those of ordinary skill in the art.

It should be understood that the various teachings herein may be readily combined with the various teachings of U.S. Pub. No. 2017/0105755, entitled "Surgical Instrument with Dual Mode End Effector and Compound Lever with Detents," published Apr. 20, 2017, issued as U.S. Pat. No. 11,020,200 on Jun. 1, 2021, the disclosure of which is incorporated by reference herein. Various suitable ways in which the teachings herein may be combined with the teachings of U.S. Pub. No. 2017/0105755, issued as U.S. Pat. No. 11,020,200 on Jun. 1, 2021, will be apparent to those of ordinary skill in the art.

It should be understood that the various teachings herein may be readily combined with the various teachings of U.S. Pub. No. 2017/0105788, entitled "Surgical Instrument with Dual Mode End Effector and Modular Clamp Arm Assembly," published Apr. 20, 2017, issued as U.S. Pat. No. 10,893,914 on Jan. 19, 2021, the disclosure of which is incorporated by reference herein. Various suitable ways in which the teachings herein may be combined with the teachings of U.S. Pub. No. 2017/0105788, issued as U.S. Pat. No. 10,893,914 on Jan. 19, 2021, will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/798,680, entitled "Surgical Instrument with Removable Clamp Arm Assembly," filed Oct. 31, 2017, published as U.S. Pat. Pub. No. 2018/0132883 on May 17, 2018, issued as U.S. Pat. No. 11,116,531 on Sep. 14, 2021, the disclosure of which is incorporated by reference herein. Various suitable ways in which the teachings herein may be combined with the teachings of U.S. patent application Ser. No. 15/798,680, issued as U.S. Pat. No. 11,116,531 on Sep. 14, 2021, will be apparent to those of ordinary skill in the art in view of the teachings herein.

In addition to the foregoing, the teachings herein may be readily combined with the teachings of U.S. patent application Ser. No. 15/798,703, entitled "Surgical Instrument with Removable End Effector Components," filed Oct. 31, 2017, published as U.S. Pat. Pub. No. 2018/0132887 on May 17, 2018, issued as U.S. Pat. No. 11,602,364 on Mar. 14, 2023, the disclosure of which is incorporated by reference herein. Various suitable ways in which the teachings herein may be combined with the teachings of U.S. patent application Ser. No. 15/798,703, issued as U.S. Pat. No. 11,602,364 on Mar. 14, 2023, will be apparent to those of ordinary skill in the art in view of the teachings herein.

In addition to the foregoing, the teachings herein may be readily combined with the teachings of U.S. patent application Ser. No. 15/798,835, entitled "Surgical Instrument with Spot Coagulation Control Algorithm," filed Oct. 31, 2017, published as U.S. Pat. Pub. No. 2018/0132926 on May 17, 2018, issued as U.S. Pat. No. 11,039,848 on Jun. 22, 2021, the disclosure of which is incorporated by reference herein. Various suitable ways in which the teachings herein may be combined with the teachings of U.S. patent application Ser. No. 15/798,835, issued as U.S. Pat. No. 11,039,848 on Jun. 22, 2021, will be apparent to those of ordinary skill in the art in view of the teachings herein.

In addition to the foregoing, the teachings herein may be readily combined with the teachings of U.S. patent application Ser. No. 15/798,902, entitled "Surgical Instrument with Removable Portion to Facilitate Cleaning," filed Oct. 31, 2017, published as U.S. Pat. Pub. No. 2018/0132884 on May 17, 2018, issued as U.S. Pat. No. 10,736,648 on Aug. 11, 2020, the disclosure of which is incorporated by reference herein. Various suitable ways in which the teachings herein may be combined with the teachings of U.S. patent application Ser. No. 15/798,902, issued as U.S. Pat. No. 10,736,648 on Aug. 11, 2020, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an end effector, including:
      (i) an ultrasonic blade, and
      (ii) a clamp arm configured to move relative to the ultrasonic blade from an opened position toward an intermediate position and a closed position, wherein the ultrasonic blade and the clamp arm are configured to receive tissue in the opened position, wherein the clamp arm is configured to clamp tissue against the ultrasonic blade in the closed position, and wherein the clamp arm is offset from the ultrasonic blade to define a predetermined gap in the intermediate position between the opened position and the closed position;
   (b) a shaft assembly projecting proximally from the end effector and including an acoustic waveguide operatively connected to the ultrasonic blade, wherein the acoustic waveguide is configured to connect to an ultrasonic transducer;
   (c) a body projecting proximally from the shaft assembly;
   (d) a clamp arm actuator operatively connected to the clamp arm and configured to selectively move relative to the body through a longitudinal plane from an opened configuration to a closed configuration to thereby direct the clamp arm respectively from the opened position toward the intermediate position and the closed position, and wherein the clamp arm actuator has a distal actuator portion further configured to move in a first lateral direction away from the longitudinal plane; and (e) a blocker operatively connected to the body and configured to inhibit movement of the clamp arm actuator from the open configuration toward the closed configuration for maintaining at least the predetermined gap between the clamp arm and the ultrasonic blade.

2. The surgical instrument of claim 1, wherein the blocker is connected to the body.

3. The surgical instrument of claim 2, wherein the blocker extends from the body along the longitudinal plane.

4. The surgical instrument of claim 3, wherein the blocker defines a gap on the longitudinal plane, and wherein the gap is configured to receive the distal actuator portion in the closed configuration.

5. The surgical instrument of claim 1, wherein the clamp arm actuator is connected to the shaft assembly at a coupling portion, and wherein the distal actuator portion is configured to selectively laterally pivot at the coupling portion.

6. The surgical instrument of claim 1, wherein the blocker is configured to inhibit movement of the clamp arm actuator from the open configuration toward the closed configuration with the clamp arm actuator selectively positioned along the longitudinal plane for maintaining at least the predetermined gap between the clamp arm and the ultrasonic blade.

7. The surgical instrument of claim 6, wherein the blocker is connected to the body.

8. The surgical instrument of claim 7, wherein the blocker extends from the body along the longitudinal plane and is configured to engage the distal actuator portion of the clamp arm actuator.

9. The surgical instrument of claim 1, wherein the blocker is configured to inhibit movement of the clamp arm actuator from the open configuration toward the closed configuration with the clamp arm actuator selectively moved from away from the longitudinal plane for maintaining at least the predetermined gap between the clamp arm and the ultrasonic blade.

10. The surgical instrument of claim 9, wherein the blocker is connected to the body.

11. The surgical instrument of claim 10, wherein the blocker extends from the body along the longitudinal plane.

12. The surgical instrument of claim 11, wherein the blocker defines a gap on the longitudinal plane, and wherein the gap is configured to receive the distal actuator portion in the closed configuration.

13. The surgical instrument of claim 1, wherein the clamp arm actuator is further configured to move toward the closed configuration without encountering the blocker with the distal actuator portion laterally directed in the first lateral direction away from the longitudinal plane.

14. The surgical instrument of claim 1, wherein the clamp arm actuator is further configured to move toward the closed configuration without encountering the blocker with the distal actuator portion in the longitudinal plane.

15. The surgical instrument of claim 1, wherein the distal actuator portion is further configured to move in a second lateral direction away from the longitudinal plane, wherein the second lateral direction is opposite from the first lateral direction.

16. A surgical instrument, comprising:
(a) an end effector, including:
   (i) an ultrasonic blade, and
   (ii) a clamp arm configured to move relative to the ultrasonic blade from an opened position toward an intermediate position and a closed position, wherein the ultrasonic blade and the clamp arm are configured to receive tissue in the opened position, wherein the clamp arm is configured to clamp tissue against the ultrasonic blade in the closed position, and wherein the clamp arm is offset from the ultrasonic blade to define a predetermined gap in the intermediate position between the opened position and the closed position;
(b) a shaft assembly projecting proximally from the end effector and including an acoustic waveguide operatively connected to the ultrasonic blade, wherein the acoustic waveguide is configured to connect to an ultrasonic transducer;
(c) a body projecting proximally from the shaft assembly;
(d) a clamp arm actuator operatively connected to the clamp arm and configured to selectively move relative to the body through a longitudinal plane from an opened configuration to a closed configuration to thereby direct the clamp arm respectively from the opened position toward the intermediate position and the closed position, wherein the clamp arm actuator has a distal actuator portion further configured to move in a first lateral direction away from the longitudinal plane, and wherein the distal actuator portion is further configured to move in a second lateral direction away from the longitudinal plane, wherein the second lateral direction is opposite from the first lateral direction; and
(e) a blocker connected to the body and configured to inhibit movement of the clamp arm actuator from the open configuration toward the closed configuration for maintaining at least the predetermined gap between the clamp arm and the ultrasonic blade,
wherein the clamp arm actuator is connected to the shaft assembly at a coupling portion, and wherein the distal actuator portion is configured to selectively laterally pivot at the coupling portion.

17. The surgical instrument of claim 16, wherein the clamp arm actuator is further configured to move toward the closed configuration without encountering the blocker with the distal actuator portion laterally directed in the first lateral direction away from the longitudinal plane.

18. The surgical instrument of claim 16, wherein the clamp arm actuator is further configured to move toward the closed configuration without encountering the blocker with the distal actuator portion in the longitudinal plane.

* * * * *